US011156612B2

(12) United States Patent
Sexton et al.

(10) Patent No.: US 11,156,612 B2
(45) Date of Patent: *Oct. 26, 2021

(54) METHODS OF DETERMINING LEVELS OF CLEAVED AND/OR INTACT KININOGEN

(71) Applicant: Takeda Pharmaceutical company Limited, Osaka (JP)

(72) Inventors: Daniel J. Sexton, Melrose, MA (US); Ryan Faucette, Melrose, MA (US); Jon A. Kenniston, Hingham, MA (US); Gregory P. Conley, Arlington, MA (US); Andrew Nixon, Hanover, MA (US); Christopher TenHoor, Hopkinton, MA (US); Burt Adelman, Concord, MA (US); Yung Chyung, Lexington, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 503 days.

This patent is subject to a terminal disclaimer.

(21) Appl. No.: 14/761,690

(22) PCT Filed: Jan. 17, 2014

(86) PCT No.: PCT/US2014/012107
§ 371 (c)(1),
(2) Date: Jul. 17, 2015

(87) PCT Pub. No.: WO2014/113712
PCT Pub. Date: Jul. 24, 2014

(65) Prior Publication Data
US 2015/0362493 A1  Dec. 17, 2015

Related U.S. Application Data

(60) Provisional application No. 61/754,607, filed on Jan. 20, 2013.

(51) Int. Cl.
| | |
|---|---|
| *G01N 33/573* | (2006.01) |
| *C07K 16/40* | (2006.01) |
| *A61K 39/395* | (2006.01) |
| *C07K 7/06* | (2006.01) |
| *C07K 16/36* | (2006.01) |

(52) U.S. Cl.
CPC ..... *G01N 33/5735* (2013.01); *A61K 39/3955* (2013.01); *C07K 7/06* (2013.01); *C07K 16/36* (2013.01); *C07K 16/40* (2013.01); *C07K 2317/21* (2013.01); *C07K 2317/76* (2013.01); *G01N 2333/745* (2013.01); *G01N 2800/065* (2013.01); *G01N 2800/102* (2013.01); *G01N 2800/52* (2013.01); *G01N 2800/70* (2013.01)

(58) Field of Classification Search
None
See application file for complete search history.

(56) References Cited

U.S. PATENT DOCUMENTS

| | | | |
|---|---|---|---|
| 4,882,272 A | 11/1989 | Scott et al. | |
| 4,908,431 A * | 3/1990 | Colman | C07K 16/18 435/337 |
| 4,985,354 A | 1/1991 | Toyomaki et al. | |
| 5,025,796 A | 6/1991 | Hargreaves et al. | |
| 5,047,323 A | 9/1991 | Colman et al. | |
| 5,472,945 A * | 12/1995 | Schmaier | C07K 14/4703 514/20.1 |
| 6,242,210 B1 | 6/2001 | Bjoerck et al. | |
| 6,913,900 B2 | 7/2005 | Kaplan et al. | |
| 10,101,344 B2 * | 10/2018 | Sexton | G01N 33/86 |
| 10,648,990 B2 | 5/2020 | Sexton et al. | |
| 10,914,747 B2 | 2/2021 | Sexton et al. | |
| 2005/0223416 A1 | 10/2005 | Nuijens et al. | |
| 2006/0069020 A1 | 3/2006 | Blair et al. | |
| 2006/0115471 A1 | 6/2006 | Colman et al. | |
| 2007/0192882 A1 | 8/2007 | Dewald | |
| 2008/0038276 A1 | 2/2008 | Sinha et al. | |
| 2008/0299549 A1 | 12/2008 | Sorge et al. | |
| 2009/0075887 A1 | 3/2009 | McPherson | |
| 2011/0154517 A1 | 6/2011 | Dewald | |
| 2011/0200611 A1 | 8/2011 | Sexton | |

(Continued)

FOREIGN PATENT DOCUMENTS

| | | |
|---|---|---|
| CN | 102405228 A | 4/2012 |
| CN | 102762203 A2 | 10/2012 |

(Continued)

OTHER PUBLICATIONS

Dobo et al, PLoS ONE, 2011; vol. 6, No. 5, 1-8.*
Reddigari, S. R. & Kaplan, A. P., Blood, 1989, 74:695-702.*
Buhler R. et al. Blood Coagulation & Fibrinolysis, 1995, 6(3):223-232.*
Schmaier et al, (The Journal of Biological Chemistry, 1987; vol. 262, No. 25 pp. 1405-1411.*
Buhler R. et al. Blood Coagulation & Fibrinolysis, 1995, vol. 6. No. 3, pp. 223-232.*
Faucette et al, Blood, Oct. 2013, vol. 122, 2347.*
Chyung et al, Ann Allergy Asthma Immunology, 2014, vol. 113, pp. 460-466.*

(Continued)

*Primary Examiner* — Bridget E Bunner
*Assistant Examiner* — Fozia M Hamud
(74) *Attorney, Agent, or Firm* — Wolf, Greenfield & Sacks, P.C.

(57) ABSTRACT

The present disclosure provides methods of evaluating a subject, e.g., a subject at risk for or suffering from a pKal-mediated or bradykinin-mediated disorder, based on values (e.g., percentages) of intact and/or cleaved kininogen in a sample of the subject. Provided methods permit analysis of patients with plasma kallikrein-mediated angioedema (KMA), or other diseases mediated by pKal useful in the evaluation and treatment. Such methods can involve the use of a detection agent that preferentially binds cleaved kininogen or intact kininogen.

15 Claims, 7 Drawing Sheets

Specification includes a Sequence Listing.

(56) References Cited

U.S. PATENT DOCUMENTS

| | | | |
|---|---|---|---|
| 2011/0212104 | A1 | 9/2011 | Beaumont et al. |
| 2011/0318359 | A1 | 12/2011 | Feener et al. |
| 2012/0201756 | A1 | 8/2012 | Sexton |
| 2013/0156753 | A1 | 6/2013 | Jin |
| 2014/0128436 | A1 | 5/2014 | Sinha et al. |
| 2016/0252527 | A1 | 9/2016 | Sexton et al. |
| 2016/0252533 | A1 | 9/2016 | Sexton et al. |
| 2018/0306807 | A1 | 10/2018 | Sexton et al. |
| 2019/0120862 | A1 | 4/2019 | Sexton et al. |
| 2020/0371120 | A1 | 11/2020 | Sexton et al. |

FOREIGN PATENT DOCUMENTS

| | | |
|---|---|---|
| EP | 0 210 029 A2 | 1/1987 |
| JP | S63-185398 A | 7/1988 |
| JP | H10-84995 A | 4/1998 |
| JP | 2001-503861 A | 5/1998 |
| JP | 2001-124779 A | 5/2001 |
| JP | 2002-221519 A | 8/2002 |
| JP | 2003-159053 A | 6/2003 |
| JP | 2009-521926 A | 6/2009 |
| JP | 2014-506319 A | 3/2014 |
| JP | 2016-505159 A | 2/2016 |
| JP | 2016-511823 A | 4/2016 |
| JP | 2016-536012 A | 11/2016 |
| JP | 2017-500584 A | 1/2017 |
| JP | 2017-503820 A | 2/2017 |
| WO | WO 2006/101387 A2 | 9/2006 |
| WO | WO 2007/079096 A2 | 7/2007 |
| WO | WO 2011/075684 A1 | 6/2011 |
| WO | WO 2012/094587 A1 | 7/2012 |
| WO | WO 2012/170945 A2 | 12/2012 |
| WO | WO 2012/170947 A2 | 12/2012 |
| WO | WO 2014/113712 A1 | 7/2014 |
| WO | WO 2015/061182 A1 | 4/2015 |
| WO | WO 2015/061183 A1 | 4/2015 |

OTHER PUBLICATIONS

Merlo et al, Atherosclerosis, 2002, vol. 161, pp. 261-261.*
Berrettini et al, Blood, 1987; vol. 68, No. 2, pp. 455-462.*
Williams et al, Transfusion and Apheresis Science, 2003, vol. 29, pp. 255-258.*
Chyung et al, Ann Allergy Asthma Immunology 113; 2014, pp. 460-466.*
Chaudhuri et al, Indian Journal of Rheumatology 2008, vol. 3, No. 1; pp. 21-28.*
Rheumatoid Arthritis, Merck Manual Professional Version, Dec. 2018.*
Alzheimer disease, Merck Manual Professional Version, Dec. 2019.*
Septic shock, Merck Manual Professional Version, Jan. 2020.*
Diabetic retinopathy, Merck Manual Professional Version, Jan. 2019.*
Blais et al., The kallikrein-kininogen-kinin system: lessons from the quantification of endogenous kinins. Peptides. Dec. 2000;21(12):1903-40. Review.
Bühler et al., Improved detection of proteolytically cleaved high molecular weight kininogen by immunoblotting using an antiserum against its reduced 47 kDa light chain. Blood Coagul Fibrinolysis. May 1995;6(3):223-32.
Colman et al., Studies on the prekallikrein (kallikreinogen)—kallikrein enzyme system of human plasma. I. Isolation and purification of plasma kallikreins. J Clin Invest. Jan. 1969;48(1):11-22.
Gallimore et al., Plasma levels of factor XII, prekallikrein and high molecular weight kininogen in normal blood donors and patients having suffered venous thrombosis. Thromb Res. 2004;114(2):91-6.
Isordia-Salas et al., The mutation Ser511Asn leads to N-glycosylation and increases the cleavage of high molecular weight kininogen in rats genetically susceptible to inflammation. Blood. Oct. 15, 2003;102(8):2835-42.

Katori et al., Evidence for the involvement of a plasma kallikrein-kinin system in the immediate hypotension produced by endotoxin in anaesthetized rats. Br J Pharmacol. Dec. 1989;98(4):1383-91.
Kerbiriou-Nabias et al., Radioimmunoassays of human high and low molecular weight kininogens in plasmas and platelets. Br J Haematol. Feb. 1984;56(2):273-86.
Ladner et al., Discovery of Ecallantide: A Potent and Selective Inhibitor of Plasma Kallikrein. J Allergy and Clinical Immuno. Jan. 1, 2007;119(1):S312.
Nguyen et al., The Simple Western™: a gel-free, blot-free, hands-free Western blotting reinvention. Nature Methods. Oct. 28, 2011;8:5-6.
Phipps et al., Plasma kallikrein mediates angiotensin II type 1 receptor-stimulated retinal vascular permeability. Hypertension. Feb. 2009;53(2):175-81. doi: 10.1161/HYPERTENSIONAHA.108.117663.
Raymond et al., Quantification of des-Arg9-bradykinin using a chemiluminescence enzyme immunoassay: application to its kinetic profile during plasma activation. J Immunol Methods. Mar. 27, 1995;180(2):247-57.
Reddigari et al., Monoclonal antibody to human high-molecular-weight kininogen recognizes its prekallikrein binding site and inhibits its coagulant activity. Blood. Aug. 1, 1989;74(2):695-702.
Scott et al., A new assay for high molecular weight kininogen in human plasma using a chromogenic substrate. Thromb Res. Dec. 15, 1987;48(6):685-700.
U.S. Appl. No. 15/030,790, filed Apr. 20, 2016, Published, 2016-0252533.
U.S. Appl. No. 15/030,811, filed Apr. 20, 2016, Published, 2016-0252527.
PCT/US2014/061242, Feb. 3, 2015, International Search Report and Written Opinion.
PCT/US2014/061242, May 6, 2016, International Preliminary Report on Patentability.
EP 14740444.6, Jun. 17, 2016, Extended European Search Report.
PCT/US2014/012107, Apr. 14, 2014, International Search Report and Written Opinion.
PCT/US2014/012107, Jun. 30, 2015, International Preliminary Report on Patentability.
PCT/US2014/061247, Feb. 4, 2015, International Search Report and Written Opinion.
PCT/US2014/06124, May 6, 2016, International Preliminary Report on Patentability.
[No Author Listed], Image Studio Software Compatible with Mac® Systems Now Available from LI-COR!. BioB Blog. May 8, 2012:1-3.
Cugno et al., Activation of the coagulation cascade in C1-inhibitor deficiencies. Blood. May 1, 1997;89(9):3213-8.
Cugno et al., Activation of the contact system and fibronolysis in autoimmune acquired angioedema: A rationale for prophylactic use of tranexamic acid. J Allergy Clin Immunol. 1994;93(5):870-876.
Defendi et al., Enzymatic assays for the diagnosis of bradykinin-dependent angioedema. PLoS One. Aug. 5, 2013;8(8):e70140. doi:10.1371/journal.pone.0070140. Print 2013. Erratum in: PLoS One. 2014;9(6):e100345.
Isordia-Salas et al., The role of plasma high molecular weight kininogen in experimental intestinal and systemic inflammation. Arch Med Res. Jan.-Feb. 2005;36(1):87-95.
Joseph et al., Studies of the mechanisms of bradykinin generation in hereditary angioedema plasma. Ann Allergy Asthma Immunol. Sep. 2008;101(3):279-86. doi: 10.1016/S1081-1206(10)60493-0.
Khan et al., High-molecular-weight kininogen fragments stimulate the secretion of cytokines and chemokines through uPAR, Mac-1, and gC1qR in monocytes. Arterioscler Thromb Vasc Biol. Oct. 2006;26(10):2260-6. Epub Aug. 10, 2006. Erratum in: Arterioscler Thromb Vasc Biol. Nov. 2006;26(11):e146.
Reddigari et al., Quantification of human high molecular weight kininogen by immunoblotting with a monoclonal anti-light chain antibody. J Immunol Methods. Apr. 21, 1982;119(1):19-25.
Schousboe et al., High molecular wieht kininogen binds to laminin—characterization and kinetic analyis. FEBS Journal. 2009;276:5228-5238.

(56) References Cited

OTHER PUBLICATIONS

Torzewski et al., Animal Models of c-Reactive Protein. Hindawi Publishing Corpl, Mediators of Inflammation. 2014:1-7.

Van Der Vekens et al., Human and equine cardiovascular endrocrinology: beware to compare. Cardivosacular Endicronology. 2013;2(4):67-76.

Zhang et al., Two-chain high molecular weight kininogen induces endothelial cell apoptosis and inhibits angiogenesis: partial activity within domain 5. FASEB J. Dec. 2000;14(15):2589-600.

[No Author Listed], Mouse High Molecular Weight Kinnogen (HMWK) ELISA Kit (Cat. No. BMS089195). MyBiosource Datasheet. Jan. 2, 1984. Revtrieved from <https://www.mybiosource.com/prods/ELIS-A-Kit/Mouse/High-Molecular-Weight-Kinogen/HMWK/datasheet.php?products_id=89195> on Dec. 13, 2018. 4 pages.

Ishiguro et al., Mapping of functional domains of human high molecular weight and low molecular weight kininogens using murine monoclonal antibodies. Biochemistry. Nov. 3, 1987;26(22):7021-9.

Nielsen et al., Hereditary angio-oedema: new clinical observations and autoimmune screening, complement and kallikrein-kinin analyses. J Intern Med. Feb. 1996;239(2):119-30.

Reddigari et al., Cleavage of human high-molecular weight kininogen by purified kallikreins and upon contact activation of plasma. Blood. May 1988;71(5):1334-40.

Scott et al., Sensitive antigenic determinations of high molecular weight kininogen performed by covalent coupling of capture antibody. J Lab Clin Med. Jan. 1992;119(1):77-86. Abstract only.

Syvänen et al., A radioimmunoassay for the detection of molecular forms of human plasma kininogen. FEBS Lett. Jul. 6, 1981;129(2):241-5.

Uchida et al., Differential assay method for high molecular weight and low molecular weight kininogens. Thromb Res. 1979;15(1-2):127-34.

Cugno et al., Activation of factor XII and cleavage of high molecular weight kininogen during acute attacks in hereditary and acquired C1-inhibitor deficiencies. Immunopharmacology. Jun. 1996;33(1-3):361-4.

Devani et al., Kallikrein-kinin system activation in Crohn's disease: differences in intestinal and systemic markers. Am J Gastroenterol. Aug. 2002;97(8):2026-32.

Veloso et al., A monoclonal anti-human plasma prekallikrein antibody that inhibits activation of prekallikrein by factor XIIa on a surface. Blood. Oct. 1987;70(4):1053-62.

Cugno et al., C1-inhibitor deficiency and angioedema: molecular mechanisms and clinical progress. Trends Mol Med. Feb. 2009;15(2):69-78. doi: 10.1016/j.molmed.2008.12.001. Epub Jan. 21, 2009.

Kenniston et al., Inhibition of plasma kallikrein by a highly specific active site blocking antibody. J Biol Chem. Aug. 22, 2014;289(34):23596-608. doi: 10.1074/jbc.M114.569061. Epub Jun. 26, 2014.

Sexton et al., Discovery and Characterization of a Fully Human Monoclonal Antibody Inhibitor of Plasma Kallikrein for the Treatment of Plasma Kallikrein-Mediated Edema. J. Allergy Clin. Immunol. Feb. 2013;131(2):AB32.

U.S. Appl. No. 16/849,492, filed Apr. 14, 2020, Sexton et al.

U.S. Appl. No. 17/141,690, filed Jan. 5, 2021, Sexton et al.

Bennett R., BioCryst Announces Initiation of a Phase 1 Clinical Trial of BCX4161 for the Treatment of Hereditary Angioedema. BioCryst Pharmaceuticals, Inc. Mar. 25, 2013. 2 pages.

Mutch et al., Immobilized transition metals stimulate contact activation and drive factor XII-mediated coagulation. J Thromb Haemost. Oct. 2012;10(10):2108-15. doi: 10.1111/j.1538-7836.2012.04890.x.

Page et al., An autoantibody to human plasma prekallikrein blocks activation of the contact system. Br J Haematol. May 1994;87(1):81-6.

Sexton et al., Inhibition of the plasma kallikrein-kinin system activation by DX-2930, a fully human monoclonal antibody inhibitor of plasma kallikrein. Journal of Angioedema. May 2013;1(1):45.

Zuraw et al., New promise and hope for treating hereditary angioedema. Expert Opin Investig Drugs. May 2008;17(5):697-706. doi: 10.1517/13543784.17.5.697.

\* cited by examiner

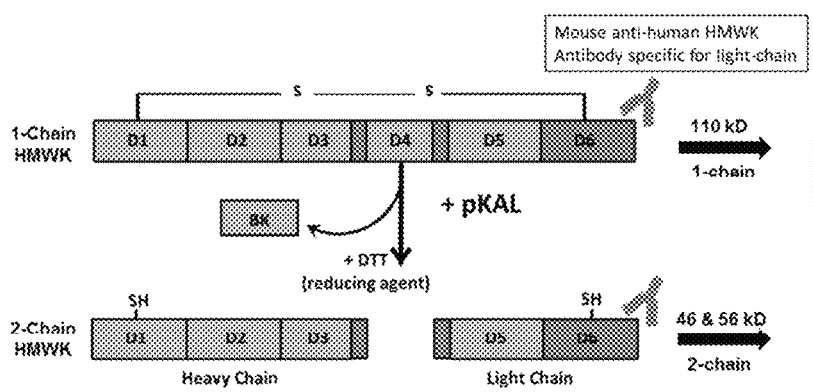
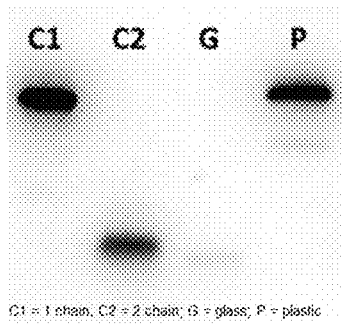
FIG. 4A
FIG. 4B
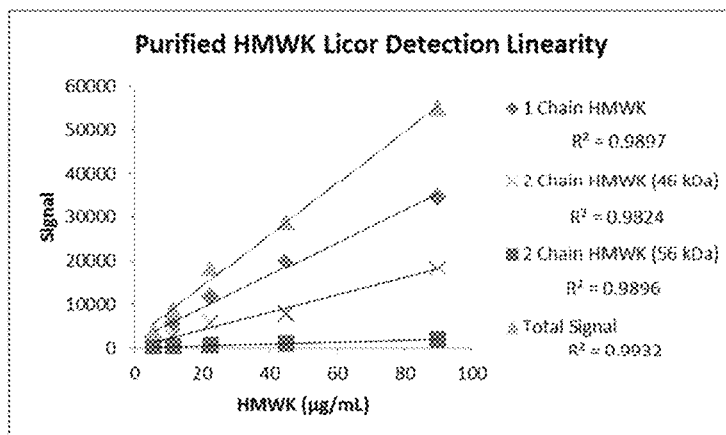
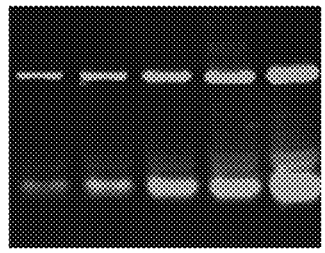
FIG. 5A
FIG. 5B
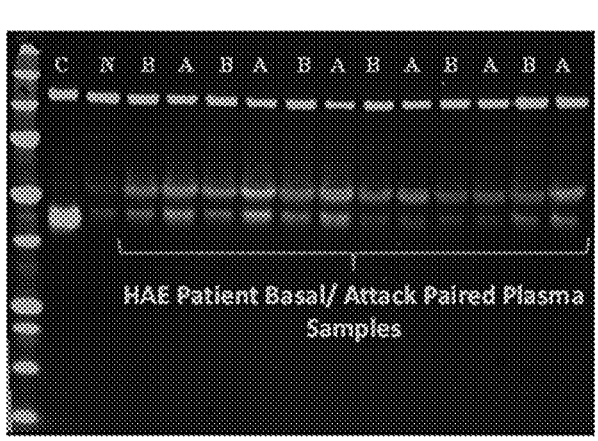
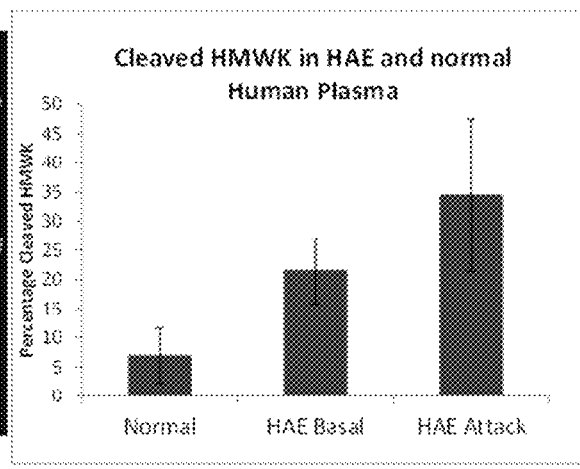
FIG. 6A
FIG. 6B

SEQUENCE LISTING

<160> NUMBER OF SEQ ID NOS: 9

<210> SEQ ID NO 1
<211> LENGTH: 644
<212> TYPE: PRT
<213> ORGANISM: Homo sapiens

<400> SEQUENCE: 1

Met Lys Leu Ile Thr Ile Leu Phe Leu Cys Ser Arg Leu Leu Leu Ser

-continued

```
1               5                   10                  15
Leu Thr Gln Glu Ser Gln Ser Glu Glu Ile Asp Cys Asn Asp Lys Asp
                20                  25                  30

Leu Phe Lys Ala Val Asp Ala Ala Leu Lys Lys Tyr Asn Ser Gln Asn
                35                  40                  45

Gln Ser Asn Asn Gln Phe Val Leu Tyr Arg Ile Thr Glu Ala Thr Lys
            50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
                100                 105                 110

Lys Arg Ser Ser Thr Lys Phe Ser Val Ala Thr Gln Thr Cys Gln Ile
            115                 120                 125

Thr Pro Ala Glu Gly Pro Val Val Thr Ala Gln Tyr Asp Cys Leu Gly
            130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Asn Thr Gln His Ser Ser Leu
                165                 170                 175

Phe Met Leu Asn Glu Val Lys Arg Ala Gln Arg Gln Val Val Ala Gly
                180                 185                 190

Leu Asn Phe Arg Ile Thr Tyr Ser Ile Val Gln Thr Asn Cys Ser Lys
            195                 200                 205

Glu Asn Phe Leu Phe Leu Thr Pro Asp Cys Lys Ser Leu Trp Asn Gly
            210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
                260                 265                 270

Thr Asn Ser Pro Glu Leu Glu Glu Thr Leu Thr His Thr Ile Thr Lys
            275                 280                 285

Leu Asn Ala Glu Asn Asn Ala Thr Phe Tyr Phe Lys Ile Asp Asn Val
            290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
                340                 345                 350

Ala Glu Val Tyr Val Val Pro Trp Glu Lys Lys Ile Tyr Pro Thr Val
            355                 360                 365

Asn Cys Gln Pro Leu Gly Met Ile Ser Leu Met Lys Arg Pro Pro Gly
            370                 375                 380

Phe Ser Pro Phe Arg Ser Arg Ile Gly Glu Ile Lys Glu Glu Thr
385                 390                 395                 400

Thr Val Ser Pro Pro His Thr Ser Met Ala Pro Ala Gln Asp Glu Glu
                405                 410                 415

Arg Asp Ser Gly Lys Glu Gln Gly His Thr Arg Arg His Asp Trp Gly
            420                 425                 430
```

```
His Glu Lys Gln Arg Lys His Asn Leu Gly His Gly His Lys His Glu
            435                 440                 445

Arg Asp Gln Gly His Gly Gln Arg Gly His Gly Leu Gly His Gly
    450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
                485                 490                 495

His Lys His Gly His Gly His Gly Lys His Lys Asn Lys Gly Lys Lys
                500                 505                 510

Asn Gly Lys His Asn Gly Trp Lys Thr Glu His Leu Ala Ser Ser Ser
            515                 520                 525

Glu Asp Ser Thr Thr Pro Ser Ala Gln Thr Gln Glu Lys Thr Glu Gly
530                 535                 540

Pro Thr Pro Ile Pro Ser Leu Ala Lys Pro Gly Val Thr Val Thr Phe
545                 550                 555                 560

Ser Asp Phe Gln Asp Ser Asp Leu Ile Ala Thr Met Met Pro Pro Ile
                565                 570                 575

Ser Pro Ala Pro Ile Gln Ser Asp Asp Asp Trp Ile Pro Asp Ile Gln
            580                 585                 590

Ile Asp Pro Asn Gly Leu Ser Phe Asn Pro Ile Ser Asp Phe Pro Asp
            595                 600                 605

Thr Thr Ser Pro Lys Cys Pro Gly Arg Pro Trp Lys Ser Val Ser Glu
            610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 2
<211> LENGTH: 362
<212> TYPE: PRT
<213> ORGANISM: Homo sapiens

<400> SEQUENCE: 2

Gln Glu Ser Gln Ser Glu Glu Ile Asp Cys Asn Asp Lys Asp Leu Phe
1               5                   10                  15

Lys Ala Val Asp Ala Ala Leu Lys Lys Tyr Asn Ser Gln Asn Gln Ser
            20                  25                  30

Asn Asn Gln Phe Val Leu Tyr Arg Ile Thr Glu Ala Thr Lys Thr Val
        35                  40                  45

Gly Ser Asp Thr Phe Tyr Ser Phe Lys Tyr Glu Ile Lys Glu Gly Asp
    50                  55                  60

Cys Pro Val Gln Ser Gly Lys Thr Trp Gln Asp Cys Glu Tyr Lys Asp
65                  70                  75                  80

Ala Ala Lys Ala Ala Thr Gly Glu Cys Thr Ala Thr Val Gly Lys Arg
                85                  90                  95

Ser Ser Thr Lys Phe Ser Val Ala Thr Gln Thr Cys Gln Ile Thr Pro
            100                 105                 110

Ala Glu Gly Pro Val Val Thr Ala Gln Tyr Asp Cys Leu Gly Cys Val
        115                 120                 125

His Pro Ile Ser Thr Gln Ser Pro Asp Leu Glu Pro Ile Leu Arg His
    130                 135                 140

Gly Ile Gln Tyr Phe Asn Asn Asn Thr Gln His Ser Ser Leu Phe Met
145                 150                 155                 160
```

```
Leu Asn Glu Val Lys Arg Ala Gln Arg Gln Val Ala Gly Leu Asn
                165                 170                 175

Phe Arg Ile Thr Tyr Ser Ile Val Gln Thr Asn Cys Ser Lys Glu Asn
            180                 185                 190

Phe Leu Phe Leu Thr Pro Asp Cys Lys Ser Leu Trp Asn Gly Asp Thr
        195                 200                 205

Gly Glu Cys Thr Asp Asn Ala Tyr Ile Asp Ile Gln Leu Arg Ile Ala
    210                 215                 220

Ser Phe Ser Gln Asn Cys Asp Ile Tyr Pro Gly Lys Asp Phe Val Gln
225                 230                 235                 240

Pro Pro Thr Lys Ile Cys Val Gly Cys Pro Arg Asp Ile Pro Thr Asn
                245                 250                 255

Ser Pro Glu Leu Glu Glu Thr Leu Thr His Thr Ile Thr Lys Leu Asn
            260                 265                 270

Ala Glu Asn Asn Ala Thr Phe Tyr Phe Lys Ile Asp Asn Val Lys Lys
        275                 280                 285

Ala Arg Val Gln Val Val Ala Gly Lys Lys Tyr Phe Ile Asp Phe Val
    290                 295                 300

Ala Arg Glu Thr Thr Cys Ser Lys Glu Ser Asn Glu Glu Leu Thr Glu
305                 310                 315                 320

Ser Cys Glu Thr Lys Lys Leu Gly Gln Ser Leu Asp Cys Asn Ala Glu
                325                 330                 335

Val Tyr Val Val Pro Trp Glu Lys Lys Ile Tyr Pro Thr Val Asn Cys
            340                 345                 350

Gln Pro Leu Gly Met Ile Ser Leu Met Lys
        355                 360

<210> SEQ ID NO 3
<211> LENGTH: 255
<212> TYPE: PRT
<213> ORGANISM: Homo sapiens

<400> SEQUENCE: 3

Ser Ser Arg Ile Gly Glu Ile Lys Glu Thr Thr Val Ser Pro Pro
1               5                   10                  15

His Thr Ser Met Ala Pro Ala Gln Asp Glu Glu Arg Asp Ser Gly Lys
                20                  25                  30

Glu Gln Gly His Thr Arg Arg His Asp Trp Gly His Glu Lys Gln Arg
            35                  40                  45

Lys His Asn Leu Gly His Gly His Lys His Glu Arg Asp Gln Gly His
        50                  55                  60

Gly His Gln Arg Gly His Gly Leu Gly His Gly His Glu Gln Gln His
65                  70                  75                  80

Gly Leu Gly His Gly His Lys Phe Lys Leu Asp Asp Leu His
                85                  90                  95

Gln Gly Gly His Val Leu Asp His Gly His Lys His Lys His Gly His
            100                 105                 110

Gly His Gly Lys His Lys Asn Lys Gly Lys Lys Asn Gly Lys His Asn
        115                 120                 125

Gly Trp Lys Thr Glu His Leu Ala Ser Ser Glu Asp Ser Thr Thr
    130                 135                 140

Pro Ser Ala Gln Thr Gln Glu Lys Thr Glu Gly Pro Thr Pro Ile Pro
145                 150                 155                 160

Ser Leu Ala Lys Pro Gly Val Thr Val Thr Phe Ser Asp Phe Gln Asp
```

```
                165                 170                 175
Ser Asp Leu Ile Ala Thr Met Met Pro Pro Ile Ser Pro Ala Pro Ile
            180                 185                 190

Gln Ser Asp Asp Asp Trp Ile Pro Asp Ile Gln Ile Asp Pro Asn Gly
            195                 200                 205

Leu Ser Phe Asn Pro Ile Ser Asp Phe Pro Asp Thr Thr Ser Pro Lys
            210                 215                 220

Cys Pro Gly Arg Pro Trp Lys Ser Val Ser Glu Ile Asn Pro Thr Thr
225                 230                 235                 240

Gln Met Lys Glu Ser Tyr Tyr Phe Asp Leu Thr Asp Gly Leu Ser
            245                 250                 255

<210> SEQ ID NO 4
<211> LENGTH: 304
<212> TYPE: PRT
<213> ORGANISM: Artificial Sequence
<220> FEATURE:
<223> OTHER INFORMATION: Synthetic polypeptide

<400> SEQUENCE: 4

Met Ile Tyr Thr Met Lys Lys Val His Ala Leu Trp Ala Ser Val Cys
1               5                   10                  15

Leu Leu Leu Asn Leu Ala Pro Ala Pro Leu Asn Ala Asp Ser Glu Glu
            20                  25                  30

Asp Glu Glu His Thr Ile Ile Thr Asp Thr Glu Leu Pro Pro Leu Lys
        35                  40                  45

Leu Met His Ser Phe Cys Ala Phe Lys Ala Asp Asp Gly Pro Cys Lys
    50                  55                  60

Ala Ile Met Lys Arg Phe Phe Phe Asn Ile Phe Thr Arg Gln Cys Glu
65                  70                  75                  80

Glu Phe Ile Tyr Gly Gly Cys Glu Gly Asn Gln Asn Arg Phe Glu Ser
                85                  90                  95

Leu Glu Glu Cys Lys Lys Met Cys Thr Arg Asp Asn Ala Asn Arg Ile
            100                 105                 110

Ile Lys Thr Thr Leu Gln Gln Glu Lys Pro Asp Phe Cys Phe Leu Glu
        115                 120                 125

Glu Asp Pro Gly Ile Cys Arg Gly Tyr Ile Thr Arg Tyr Phe Tyr Asn
130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
    210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
            260                 265                 270

Gln Arg Ile Ser Lys Gly Gly Leu Ile Lys Thr Lys Arg Lys Arg Lys
```

```
                275                 280                 285
Lys Gln Arg Val Lys Ile Ala Tyr Glu Glu Ile Phe Val Lys Asn Met
            290                 295                 300

<210> SEQ ID NO 5
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 5

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 6
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ile Met Met Trp Val Arg Gln Ala Pro Gly Lys Gly Leu Glu Trp Val
        35                  40                  45

Ser Gly Ile Tyr Ser Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Arg Arg Ile Gly Val Pro Arg Arg Asp Glu Phe Asp Ile Trp
            100                 105                 110

Gly Gln Gly Thr Met Val Thr Val Ser Ser
        115                 120

<210> SEQ ID NO 7
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 7

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45
```

```
Tyr Lys Ala Ser Thr Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65              70                  75                  80

Asp Asp Phe Ala Thr Tyr Tyr Cys Gln Gln Tyr Asn Thr Tyr Trp Thr
                 85                  90                  95

Phe Gly Gln Gly Thr Lys Val Glu Ile
                100             105

<210> SEQ ID NO 8
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 8

Glu Ala Met His Ser Phe Cys Ala Phe Lys Ala Asp Asp Gly Pro Cys
 1               5                  10                  15

Arg Ala Ala His Pro Arg Trp Phe Phe Asn Ile Phe Thr Arg Gln Cys
                 20                  25                  30

Glu Glu Phe Ile Tyr Gly Gly Cys Glu Gly Asn Gln Asn Arg Phe Glu
             35                  40                  45

Ser Leu Glu Glu Cys Lys Lys Met Cys Thr Arg Asp
     50                  55                  60

<210> SEQ ID NO 9
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 9

Met His Ser Phe Cys Ala Phe Lys Ala Asp Asp Gly Pro Cys Arg Ala
 1               5                  10                  15

Ala His Pro Arg Trp Phe Phe Asn Ile Phe Thr Arg Gln Cys Glu Glu
                 20                  25                  30

Phe Ser Tyr Gly Gly Cys Gly Gly Asn Gln Asn Arg Phe Glu Ser Leu
             35                  40                  45

Glu Glu Cys Lys Lys Met Cys Thr Arg Asp
     50                  55
```

METHODS OF DETERMINING LEVELS OF CLEAVED AND/OR INTACT KININOGEN

CROSS-REFERENCE TO RELATED APPLICATIONS

This application is a national stage filing under 35 U.S.C. § 371 of international PCT application PCT/US2014/012107, filed Jan. 17, 2014, which claims the benefit of U.S. Provisional Application No. 61/754,607, filed Jan. 20, 2013, each of which is incorporated by reference herein in its entirety.

BACKGROUND

Plasma kallikrein (pKal) is the primary bradykinin-generating enzyme in the circulation. The activation of pKal occurs via the contact system which has been linked to disease pathology associated with hereditary angioedema (HAE). Bradykinin is a key mediator of pain, inflammation, edema and angiogenesis.

Kininogens are precursors of kinin, such as bradykinin and kallikrein. There are two types of human kininogens, high molecular-weight kininogen (HMWK) and low molecular-weight kininogen (LMWK), which are splicing variants. HMWK acts mainly as a cofactor on coagulation and inflammation and is the preferred substrate for pKal-mediated bradykinin generation. Both HMWKs and LMWKs are cysteine protease inhibitors.

SUMMARY OF THE INVENTION

Plasma kallikrein (pKal) is a serine protease component of the contact system and is the primary bradykinin-generating enzyme in the circulation. The contact system is activated by either factor XIIa upon exposure to foreign or negatively charged surfaces or on endothelial cell surfaces by prolylcarboxypeptidases (Sainz I. M. et al., Thromb Haemost 98, 77-83, 2007). Activation of the plasma kallikrein amplifies intrinsic coagulation via its feedback activation of factor XII and enhances inflammation via the production of the proinflammatory nonapeptide bradykinin. As the primary kininogenase in the circulation, pKal is largely responsible for the generation of bradykinin in the vasculature. A genetic deficiency in the C1-inhibitor protein (C1-INH), the major natural inhibitor of plasma kallikrein, leads to hereditary angioedema (HAE). Patients with HAE suffer from acute attacks of painful edema often precipitated by unknown triggers (Zuraw B. L. et al., N Engl J Med 359, 1027-1036, 2008). Through the use of pharmacological agents or genetic studies in animal models, the plasma kallikrein-kinin system (plasma KKS) has been implicated in various diseases.

As described herein, a Westernblot assay was developed for detection of intact (1-chain) and cleaved (2-chain) high molecular weight kininogen (HMWK), using a detection reagent (e.g., an antibody) that specifically (e.g., preferentially) binds either the intact kininogen or the cleaved kininogen, and optionally, does not bind LMWK. Such a detection reagent can be used to monitor relative amounts of 1-chain and 2-chain HMWK in patient plasma. By applying this method, it was found that the level (e.g., the percentage) of cleaved kininogen in a patient sample is elevated in disease states that are known to be mediated by excess pKal activation, such as edematous HAE attacks. The percent cleaved kininogen in the plasma of patients with other diseases can subsequently be tested to determine whether active pKal is associated with the disease. Other diseases that have been tested and shown to have cleaved kininogen elevations, relative to healthy plasma, include rheumatoid arthritis (RA), ulcerative colitis (UC), and Crohn's disease.

Accordingly, one aspect of the present disclosure relates to a method for identifying a subject at risk for or having a pKal-mediated disorder, the method comprising: (a) measuring a level of a cleaved kininogen (e.g., HMWK) and a level of an intact kininogen (e.g., HMWK) in a sample of a subject (e.g., a blood sample or a plasma sample) via, e.g., a Western blot assay; (b) determining a value (e.g., percentage) of the cleaved kininogen, a value of intact kininogen (e.g., percentage), or both, in the sample; and (c) identifying the subject as being at risk for or having a pKal-mediated disorder if the value of the cleaved kininogen, the value of the intact kininogen, or both, deviates from a reference value. In some examples, the percentage of cleaved kininogen is determined and the subject is identified as at risk for or having the target disease if the percentage of cleaved kininogen in the sample is at or above a reference value.

In some embodiments, the levels of the cleaved kininogen and intact kininogen are measured by a detection agent (e.g., an antibody) that specifically (e.g., preferentially) binds either the cleaved or the intact kininogen. Such a detection agent (e.g., an antibody) can bind both the intact and cleaved kininogen but does not bind LMWK. In other embodiments, the levels of the cleaved kininogen and intact kininogen are measured by a detection agent (e.g., an antibody), which specifically binds cleaved kininogen as compared to intact kininogen, or specifically binds intact kininogen as compared to cleaved kininogen. In one example, the detection reagent is an antibody that specifically binds cleaved kininogen as compared to intact kininogen. In another example, the detection agent is an antibody that binds to the C-terminus of the light chain of cleaved kininogen, which is not present in LMWK.

The pKal-mediated disorder can be hereditary angioedema (HAE), rheumatoid arthritis, ulcerative colitis, or Crohn's disease. If the subject is identified as being at risk for or having a pKal-mediated disorder, the method as described herein can further comprise administering an effective amount of a pKal inhibitor to the subject. In some examples, the pKal inhibitor is DX-88, EPIKAL-2 or DX-2930.

In some embodiments, the sample is from a subject having a symptom of a pKal-mediated disorder, including, but not limited to, edema, recurrent attacks of swelling, swelling wherein said swelling is completely or predominantly peripheral, hives, redness, pain, and swelling in the absence of evidence of infection; or non-histamine-mediated edema. In other embodiments, the sample is from a subject having no symptom of a pKal-mediated disorder at the time the sample is collected, has no history of a symptom of a pKal-mediated disorder, or no history of a pKal-mediated disorder. Alternatively or in addition, the subject is resistant to an anti-histamine therapy, a corticosteroid therapy, or both.

In another aspect, the present disclosure provides a method for determining if a disorder is susceptible to treatment with a pKal inhibitor, the method comprising: (a) measuring a level of a cleaved kininogen (e.g., HMWK) and a level of an intact kininogen (e.g., HMWK) in a sample of a subject (e.g., a blood sample or a plasma sample) having the disorder; (b) determining a value (e.g., percentage) of the cleaved kininogen, a value (e.g., percentage) of intact kininogen, or both, in the sample; and (c) identifying the disorder as being susceptible to treatment with a pKal inhibitor if the value of cleaved kininogen, the value of intact kininogen, or both, deviates from a reference value. In one example, the percentage of cleaved kininogen is determined and the disease is identified as being susceptible to the treatment if the percentage of cleaved kininogen is at or above a reference value.

In some embodiments, the levels of the cleaved kininogen and intact kininogen are measured by a detection agent (e.g., an antibody), which specifically binds cleaved kininogen as compared to intact kininogen, or specifically binds intact kininogen as compared to cleaved kininogen. In some examples, the detection reagent is an antibody that specifically binds cleaved kininogen as compared to intact kininogen. In other examples, the detection reagent is an antibody that binds to the C-terminus of the light chain of cleaved kininogen. In any of the methods described herein, the levels of the intact kininogen and cleaved kininogen can be measured by Western blot assay.

If the disorder is identified as susceptible to treatment of a pKal inhibitor, the method can further comprise administering to the subject an effective amount of a pKal inhibitor, which includes, but is not limited to, DX-88, EPIKAL-2, or DX-2930.

In yet another aspect, the present disclosure provides a method for evaluating a treatment of a pKal-mediated disorder in a subject, the method comprising: (a) measuring levels of a cleaved kininogen (e.g., HMWK) and levels of an intact kininogen (e.g., HMWK) in samples (e.g., blood samples or plasma samples) collected from the subject before and after the treatment or during the course of the treatment; (b) determining a value (e.g., percentage) of cleaved kininogen, a value (e.g., percentage) of intact kininogen, or both, in each sample based on the levels of cleaved and intact kininogen in the same sample; and (c) evaluating effectiveness of the treatment based on changes in the value of cleaved and/or intact kininogen before and after the treatment or over the course of the treatment. For example, a decrease of the cleaved kininogen percentage after the treatment or over the course of the treatment indicates that the treatment is effective on the subject. In some embodiments, the treatment comprises administering to the subject an effective amount of a pKal inhibitor, e.g., DX-88, EPIKAL-2 or DX-2930.

In any of the evaluation methods described herein, the levels of the cleaved kininogen and intact kininogen can be measured by a detection agent (e.g., an antibody), which specifically binds cleaved kininogen as compared to intact kininogen, or specifically binds intact kininogen as compared to cleaved kininogen. In some examples, the detection reagent is an antibody that specifically binds cleaved kininogen as compared to intact kininogen. In other examples, the detection agent is an antibody that binds to the C-terminus of the light chain of cleaved kininogen. In any of the methods described herein, the levels of the intact kininogen and cleaved kininogen can be measured by Western blot assay.

In some embodiments, the pKal-mediated disorder is hereditary angioedema (HAE), rheumatoid arthritis, ulcerative colitis, or Crohn's disease.

Further, the present disclosure provides a method for determining a value of cleaved kininogen, a value of intact kininogen, or both, in a sample, comprising (a) contacting a sample (e.g., a blood sample or a plasma sample) containing intact and cleaved kininogen with a detection reagent under conditions allowing for interaction between the detection agent and the intact and cleaved kininogen, wherein the detection agent specifically binds cleaved kininogen as compared to intact kininogen, or specifically binds intact kininogen as compared to cleaved kininogen; (b) measuring the level of cleaved kininogen and/or intact kininogen in the sample based on their interaction with the detection reagent; and (c) determining a value (e.g., percentage) of the cleaved kininogen, a value (e.g., percentage) of intact kininogen, or both, in the sample based on the levels of the cleaved kininogen and intact kininogen. In some embodiments, the detection reagent is an antibody, such as antibody specifically binding to cleaved kininogen as compared to intact kininogen, or an antibody that binds to the C-terminus of the light chain of cleaved kininogen. In some embodiments, the amounts of the intact kininogen and cleaved kininogen are measured by Western blot assay.

Also within the scope of the present disclosure are (i) a method for treating a pKal-mediated disease, comprising administering to a subject in need thereof an effective amount of a pKal inhibitor as described herein, wherein the subject has a value (e.g., percentage) of cleaved kininogen, a value (e.g., percentage) of intact kininogen, or both, that deviates from a reference value, (ii) a pharmaceutical composition for use in treating a pKal-mediated disease of a subject, wherein the composition comprises a pKal inhibitor and a pharmaceutically acceptable carrier and wherein the subject has a deviated value of cleaved kininogen and/or intact kininogen, as compared to a reference value, and (iii) use of the pharmaceutical composition for manufacturing a medicament for use in treating a pKal-mediated disease, e.g., HAE. In some embodiments, the value of cleaved and/or intact kininogen is the percentage of cleaved and/or intact kininogen in the sample.

The following embodiments are also within the scope of the present disclosure:

Provided herein are methods of evaluating a subject, e.g., a subject at risk for or suffering from a pKal-mediated or bradykinin-mediated disorder. Provided methods permit analysis of patients with plasma kallikrein-mediated angioedema (KMA), or other diseases mediated by pKal useful in the evaluation and treatment.

Embodiments of the present disclosure provide a biomarker and use thereof in the identification and treatment of patients, e.g., patients suffering from edema caused by bradykinin that is generated by plasma kallikrein. Methods, compositions and devices disclosed herein are useful in a number of ways. For example, levels of a pKal marker can be used to identify disorders associated with elevated contact system activation. Initial screening can be followed up with in vitro or in vivo testing with plasma kallikrein inhibitors (e.g. DX-88, EPIKAL2, or DX-2930), e.g., in preclinical models of disease. A marker disclosed herein can also be used as a pharmacodynamic biomarker or to otherwise monitor the response of a subject to a kallikrein inhibitor. A marker disclosed herein can be used in a companion diagnostic to enable treatment of diseases mediated by plasma kallikrein, manage dosing during prophylactic therapy of a pKal-mediated or bradykinin-mediated disorder, e.g., HAE, non-histamine-dependent idiopathic angioedema, rheumatoid arthritis, Crohn's disease, ulcerative colitis, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

The present disclosure provides a method of evaluating or treating a subject, e.g., distinguishing a pKal-mediated disorder, e.g., bradykinin-mediated angioedema, from a histamine-mediated disorder, or predicting a future attack of a pKal-mediated disorder, comprising acquiring, e.g., determining, the level of one or more marker correlated with pKal activation (a pKal marker), disclosed herein, e.g., intact kininogen, and cleaved kininogen, thereby evaluating or treating said subject. In some embodiments, the method comprises acquiring, e.g., detecting, the level of one or more marker correlated with a histamine-mediated inflammatory response (a H-marker), e.g., tryptase.

In some embodiments, said pKal-mediated disorder is HAE, IAE, IBD, or IBS. In some embodiments, said pKal-mediated disorder is selected from non-histamine-dependent idiopathic angioedema, rheumatoid arthritis, Crohn's disease, ulcerative colitis, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

The present disclosure also provides a method of evaluating or treating a subject, said subject having a symptom consistent with both a pKal-mediated disorder, e.g., bradykinin-mediated angioedema, and a histamine related disorder, comprising a) optionally, determining that said subject has a symptom, e.g., edema or abdominal discomfort, consistent with one or both a pKal-mediated disorder and a histamine related disorder; b) if said subject has not been treated with an anti-histamine therapy for said symptom, then treating said subject with an anti-histamine therapy; c) acquiring, e.g., detecting, the level of one or more marker correlated with pKal activation (a pKal marker), e.g., intact kininogen, and cleaved kininogen; d) if said level meets a predetermined criterion, e.g., if it is at or above a reference level: selecting the subject for kallikrein inhibitor therapy; or administering a kallikrein inhibitor to said subject, thereby evaluating or treating said subject. In some embodiments, the method comprises selecting the subject for kallikrein inhibitor therapy. In certain embodiments, the method comprises administering a kallikrein inhibitor to said subject. In particular embodiments, the selecting of subjects for kallikrein inhibitor therapy; or administering a kallikrein inhibitor to said subject, occurs prior to a determination that the subject is nonresponsive to said anti-histamine therapy, e.g., occurs within 1, 2, 3, 4, 5, 6, 7, 8, 9, or 10 hours of said treatment with an anti-histamine therapy. In some embodiments, a determination that said subject has a symptom consistent with both a pKal-mediated disorder and a histamine related disorder and acquisition of a sample from said patient for determining the level of a pKal marker occur: within 30 minutes, 1, 2 or 3 hours of one another; or in the same visit to a healthcare provider.

In some embodiments, the said pKal inhibitor is selected from DX-88, DX-2930, or EpiKal-2.

In some embodiments, the method comprises acquiring, e.g., determining, the level of one or more marker correlated with a histamine-mediated inflammatory response (a H-marker). In certain embodiments, said subject is evaluated for susceptibility to a pKal-mediated disorder. In certain embodiments, said subject has a symptom of, e.g., consistent with, a pKal-mediated disorder, e.g., edema, e.g., HAE. In certain embodiments, said subject has a symptom of a disorder characterized by unwanted pKal activation and said subject has been administered an anti-histamine therapy. In particular embodiments, said anti-histamine therapy is administered within 1, 2, 3, 4, 5, 6, 7, 8, 8 or 10 hours before or after a determining step as disclosed herein. In particular embodiments, the method further comprises administering an anti-histamine therapy to said subject, e.g., before, after, or during the evaluation or determinations as disclosed herein.

In some embodiments, responsive to said determination or evaluation, administering a kallikrein inhibitor to said subject. In certain embodiments, said subject has one or more or all of the following symptoms or properties: recurrent attacks of swelling; swelling wherein said swelling is completely or predominantly peripheral, e.g., the subject has no significant abdominal or airway swelling; hives; redness, pain, and swelling in the absence of evidence of infection; fails to respond to antihistamine or corticosteroid therapy; or has non-histamine-mediated edema. In certain embodiments, said subject has persistent or recurring edema and is non-responsive to one or both of anti-histamine and steroid therapy. In certain embodiments, the subject has a no history of a pKal-mediated disorder, e.g., HAE, IAE, IBD, or IBS; the subject has a history of a pKal-mediated disorder, e.g., HAE, IAE, IBD, or IBS, the subject has no history of HAE; the subject has a history of HAE; the subject has no history of IAE; the subject has a history of IAE; the subject has no history of IBD or IBS; the subject has a history of IBD or IBS; the subject has a no history of a histamine mediated disorder, e.g., a food allergy; the subject has a history of a histamine mediated disorder, e.g., a food allergy; the subject has a no history of a pKal-mediated disorder, e.g., HAE, IAE, IBD, or IBS, and has no history of a histamine-mediated disorder, e.g., a food allergy; or the subject has no history of a pKal-mediated disorder, e.g., HAE, IAE, IBD, or IBS, and has a history of a histamine-mediated disorder, e.g., a food allergy: the subject has a history of a pKal-mediated disorder, e.g., HAE, IAE, IBD, or IBS, and has no history of a histamine-mediated disorder, a food allergy; or the subject has a history of a pKal-mediated disorder, e.g., HAE, IAE, IBD, or IBS, and has a history of a histamine-mediated disorder, e.g., a food allergy.

In some embodiments, the subject has been treated with a kallikrein inhibitor, e.g., in prophylactic therapy, e.g., for HAE, and the subject's response to the kallikrein inhibitor is evaluated or monitored, and optionally, responsive to said monitoring, a therapy is selected or administered, e.g., responsive to the determination, the dosage of the kallikrein inhibitor is adjusted. In some embodiments, a determination of a pKal marker is performed in the context of a companion diagnostic, and optionally, administration of a therapeutic is given or withheld on the basis of the determination. In certain embodiments, responsive to said treatment is relied on to identify an impending acute attack, e.g. an HAE or IEA attack. In particular embodiments, said subject is evaluated for susceptibility to idiopathic angioedema. In particular embodiments, said evaluation comprises determining if said subject is suffering from a pKal-mediated disorder, e.g., a bradykinin-mediated disorder, e.g., a pKal-mediated angioedema, or from a histamine-mediated disorder, e.g., an allergic food reaction.

In some embodiments, the subject has no history of a pKal-mediated disorder, e.g., HAE or IAE. In some embodiments, the subject has a history of a pKal-mediated disorder, e.g., HAE or IAE. In some embodiments, the subject has a no history of a pKal-mediated disorder, e.g., HAE, IAE, IBD or IBS; the subject has a history of a pKal-mediated disorder, e.g., HAE, IAE, IBD, or IBS, the subject has no history of HAE; the subject has a history of HAE; the subject has no history of IAE; the subject has a history of IAE; the subject has no history of IBD or IBS; the subject has a history of IBD or IBS; the subject has a no history of a histamine mediated disorder, e.g., a food allergy; the subject has a history of a histamine mediated disorder, e.g., a food allergy; the subject has a no history of a pKal-mediated disorder, e.g., HAE, IAE, IBD, or IBS, and has no history of a histamine-mediated disorder, e.g., a food allergy; or the subject has no history of a pKal-mediated disorder, e.g., HAE, IAE, IBD, or IBS, and has a history of a histamine-mediated disorder, e.g., a food allergy: the subject has a history of a pKal-mediated disorder, e.g., HAE, IAE, IBD, or IBS, and has no history of a histamine-mediated disorder, a food allergy; or the subject has a history of a pKal-mediated disorder, e.g., HAE, IAE, IBD, or IBS, and has a history of a histamine-mediated disorder, e.g., a food allergy.

In some embodiments, a pka marker, e.g., a pKal marker disclosed herein, is detected with an antibody-based reagent. In certain embodiments, a pKal marker is detected with sandwich immune-assay. In certain embodiments, the method comprises acquiring, e.g., detecting, the level kininogen, e.g., one or both of intact or cleaved kininogen, e.g., by an electrophorietic separation assay, e.g., a Western blot. In some embodiments, a pKal marker, e.g., kininogen, is detected in an assay which relies on separation, e.g., electrophoretic separation, e.g., by Western blot, of the analyte from other products.

In some embodiments, a pKal marker is detected with sandwich immune-assay and a second pKal marker, e.g., kininogen, is detected in an assay which relies on separation, e.g., electrophoretic separation, e.g., by Western blot, of the analyte from other products. In certain embodiments, detection of a pKal marker is qualitative. In certain embodiments, detection of a pKal marker is quantitative. In particular embodiments, a level of intact kininogen and cleaved kininogen is each detected.

In some embodiments, the method comprises comparing the level of a pKal marker, e.g., intact kininogen or cleaved kininogen, with a reference value. In certain embodiments, said reference value is a function of the level of said pKal marker in an HAE, e.g., in one or more HAE subjects. In certain embodiments, said reference value is a function of the level of said pKal marker in an HAE during an attack, e.g., in one or more HAE subjects during an acute attack. In certain embodiments, said reference value is a function of the level of a pKal marker in an IAE, e.g., in one or more IAE subjects. In certain embodiments, said reference value is a function of the level of a pKal marker in an IAE during an acute attack, e.g., in one or more IAE subjects during an acute attack. In certain embodiments, said reference value is a function of the level of a pKal marker in the absence of HAE or IAE, e.g., in one or more subjects having no history of HAE or IAE.

In particular embodiments, the method comprises e.g., responsive to a comparison, classifying the subject, e.g., classifying the subject for risk for a pKal-mediated disorder, or administering or withholding a therapy from said subject. In certain embodiments, the method comprises, e.g., responsive to a comparison, selecting a treatment for said subject. In some embodiments, the method comprises, e.g., responsive to a comparison, administering or withholding a therapy from said subject, e.g., a kallikrein binding agent; a bradykinin B2 receptor antagonist; or a C1-INH replacement agent. In particular embodiments, said treatment is the administration of a pKal inhibitor, e.g., a pKal inhibitor selected from DX-88; EpiKal-2, and DX-2930.

In some embodiments, a sample from said subject is contacted with a substrate comprising a capture agent for two or more markers, e.g., from: a pKal marker or a H marker, e.g., an anti-H marker antibody; optionally, wherein at least one capture agent is a capture agent for a pKal marker.

In some embodiments, the method comprises acquiring a sample, e.g., a blood or plasma sample from said subject.

In some embodiments, a first capture agent (for a first marker) and a second capture agent (for a second marker) are disposed on a substrate such that a signal for the presence of the first marker can be distinguished from a signal for the presence of the second marker. In certain embodiments, said first capture agent (for a first marker) is located at a first location or address and said second capture agent (for a second marker) is located at a second location or address. In particular embodiments, said first location or address and said second location or address do not overlap on said substrate. In certain embodiments, said first capture agent is for a first pKal marker. In certain embodiments, said first capture agent is for a first pKal marker and said second capture agent is for a second pKal marker. In certain embodiments, said first capture agent is for a pKal marker and said second capture agent is for an H-marker.

In certain embodiments, the method comprises contacting a substrate with a detectable, e.g., antibody, to determine the presence or amount of a pKal marker. In certain embodiments, said antibodies are labeled with a moiety that produces a colored product, emits a photon, absorbs a photon, alters a substrate, or alters the conductivity of the substrate. In certain embodiments, said antibodies are labeled with a moiety that utilizes electrochemiluminescence. In certain embodiments, said antibodies are labeled with resinium. In particular embodiments, said substrate in provided in a meso scale discovery device. In particular embodiments, said substrate in provided as a dip-stick device, suitable for use with one or both of blood and plasma. In particular embodiments, said first capture agent and said second capture agent are disposed in a common or fluidically connected chamber, e.g., a chamber, e.g., a well or depression, in a multi chamber device, e.g., a multi-well plate. In particular embodiments, said first capture agent and said second capture agent are printed onto a substrate.

In some embodiments, said capture agent for a first pKal marker is at a first location on said substrate and said capture agent for a second pKal marker is at a second location on said substrate, and said first and second locations are disposed on said substrate such that a signal for the presence of the first pKal marker can be distinguished from a signal from a second pKal marker. In certain embodiments, said substrate comprises a capture agent for a third marker at a third location, and the third location is disposed on said substrate such that a signal for the presence of the third marker can be distinguished from a signal from said first and second marker.

In some embodiments, a determination of the level of a pKal marker in a sample can be made within 1, 2, 3, 4, or 5 hours of contact of the substrate with said sample. In some embodiments, a determination of the level of two pKal markers in a sample can be made within 1, 2, 3, 4, or 5 hours of contact of the substrate with said sample. In some embodiments, a determination of the level of two pKal markers in made in simultaneously performed assays, e.g., the incubation or other intervals for the tests overlap with one another.

In another aspect, the present invention provides a substrate comprising capture agents for a plurality of pKal markers, e.g., as described herein.

In a further aspect, the present invention provides a method of determining if a disorder is susceptible to treatment with a pKal inhibitor comprising: evaluating the levels one or a plurality of pKal markers, e.g., as described herein, in e.g., a subject suffering from said disorder, or an animal model for said disorder; comparing the determined level with a reference, wherein a level that meets a predetermined criterion, e.g., if it is at or above a reference level, is indicative of a disorder susceptible to treatment with a pKal inhibitor. In some embodiments, the method comprises evaluating the effect of a kallikrein inhibitor, in vitro or in vivo, or in an animal model of said disorder.

In another aspect, the present invention provides a method of treating subject having a pKal mediated disorder, e.g., a bradykinin mediated disorder, comprising evaluating the level of a pKal marker described herein, e.g., by a method described herein, determining, and responsive to said evaluating, selecting a treatment, e.g., selecting one or both of a dosage amount or dosing frequency, of a kallikrein inhibitor. In some embodiments, the method comprises administering a kallikrein inhibitor to said subject. In some embodiments, said patient has been administered a kallikrein inhibitor prior to said evaluation. In certain embodiments, the method comprises administering a kallikrein inhibitor at said selected dosage or frequency.

In a further aspect, the present invention provides a method of determining if a disorder is susceptible to treatment with a pKal inhibitor comprising: evaluating the levels one or a plurality of pKal markers, e.g., as described herein, in e.g., a subject suffering from said disorder, or an animal model for said disorder; comparing the determined level with a reference, wherein a level that meets a predetermined criterion, e.g., if it is at or above a reference level, is indicative of a disorder susceptible to treatment with a pKal inhibitor. In some embodiments, the method comprises evaluating the effect of a kallikrein inhibitor, in vitro or in vivo, or in an animal model of said disorder.

In another aspect the invention features, methods and devices for collection of a sample, e.g., blood, with minimum contact activation. In an embodiment, the invention features a container, having disposed therein a capture reagent described herein, e.g., a kallikrein inhibitor, e.g., a polypeptide that is similar in sequence to DX-88, e.g., one that differs from DX-88 by no more than 1, 2, or 5 amino acid residues, e.g., EPIKAL-2. The container is configured, e.g., with an aperture, opening, septum, etc., so as to allow collection of a sample, e.g., blood, from a subject and binding of a pKal-related marker in the sample, e.g., pKal, with the capture reagent, in the same container. Measurement of bound species, e.g., pKal, can be carried out in the same container or in embodiments, the substrate is removed from the prior container to measurement, e.g., measurement can be in or on another device. In embodiments the volume of the container is 0.5-100, 0.5-50, 0.5-10, 1-100, 1-50, is 1-25 mls. In an embodiment the capture reagent, e.g., a pKal capture reagent, is disposed on the inner surface of the container. The capture reagent can be coupled to the surface with a first specific binding partner bound to the surface and a second specific binding partner coupled to the capture reagent. Examples of specific binding partners are biotin and avidin. In an embodiment biotinylaed capture reagent, e.g., a pKal capture reagent, e.g., a kallikrein inhibitor, e.g., a polypeptide that is similar in sequence to DX-88, e.g., one that differs from DX-88 by no more than 1, 2, or 5 amino acid residues, e.g., Epikal-2 is disposed on a surface of the container that is coated with avidin.

The present disclosure provides biomarkers capable of identifying patients with plasma kallikrein-mediated angioedema (KMA), or other diseases mediated by pKal useful in the evaluation and treatment.

Patients shown to exhibit pKal activation via a biomarker are candidates for treatment with a pKal inhibitor, such as DX-88, a small protein inhibitor of pKal approved for the treatment of the acute edematous attacks associated HAE. Other pKal inhibitors include DX-2930, which is a fully human antibody inhibitor. In some embodiments, patients shown to exhibit pKal activation via a biomarker are candidates for treatment with a bradykinin B2 receptor antagonist, e.g., Incatibant (Firazyr®). In some embodiments, patients shown to exhibit pKal activation via a biomarker are candidates for treatment with a C1-INH replacement agent, e.g., a purified human pasteurized nanofiltered C1-INH concentrate (Berinert®).

Embodiments of the invention provide a biomarker and use thereof in the identification and treatment of patients, e.g., patients suffering from edema caused by bradykinin that is generated by plasma kallikrein. Methods, compositions and devices disclosed herein are useful in a number of ways. For example, levels of a pKal marker can be used to identify disorders associated with elevated contact system activation. Initial screening can be followed up with in vitro or in vivo testing with plasma kallikrein inhibitors (e.g. DX-88, EPIKAL-2, or DX-2930), e.g., in preclinical models of disease. A marker disclosed herein can also be used as a pharmacodynamic biomarker or to otherwise monitor the response of a subject to a kallikrein inhibitor. A marker disclosed herein can be used in a companion diagnostic to enable treatment of diseases mediated by plasma kallikrein, manage dosing during prophylactic therapy of HAE, or identify an impending acute HAE attack.

The contents of all cited references including literature references, issued patents, published or non-published patent applications cited throughout this application as well as those listed below are hereby expressly incorporated by reference in their entireties for the purposes or subject matter referenced herein.

BRIEF DESCRIPTION OF DRAWINGS

FIG. 4A shows a schematic of the domain structure of 1-Chain HMWK and 2-Chain HMWK following cleavage by pKal.

FIG. 4B shows a Western blot detecting chain-1 and chain-2 of HMWK using an antibody that binds to the light chain of cleaved kininogen. C1=1-chain HMWK, C2=2-chain HMWK, G=glass, P=plastic.

FIG. 5A shows LICOR detection of purified HMWK as a semi-quantitative assay. Purified human HMWK and cleaved HMWK were titrated from 90 µg/mL to 5.6 µg/mL in HMWK-deficient human plasma. Samples were diluted 1:20 into TBS and sample loading buffer (with DTT).

FIG. 5B shows a Western blot using LICOR to detect purified HMWK. The diluted samples of FIG. 5A were run on a 4-12% bis-tris gel and, following electrophoresis, transferred to a nitrocellulose membrane. After blocking, the blot was visualized using a mouse anti-human HMWK antibody (clone #11H05), which is specific to the light chain of HMWK, and a goat anti-mouse IR Dye 680. The gels were scanned using the LI-COR Odyssey IR Scanner, which is able to detect the excitation signal of the IR Dye 680.

FIG. 6A shows a Western blot and LICOR analysis of HAE patient sample, which demonstrate that HAE patient samples display higher endogenous levels of cleaved HMWK.

FIG. 6B shows a graph quantifying the Western blot analysis of FIG. 6A. Both basal and attack HAE patient plasma had higher percent-cleaved HMWK when compared to non-disease state plasma by Licor analysis. The plasma samples analyzed were collected in an anti-protease solution, which, when compared to sodium citrated plasma samples from the same patients at the same collection time, protected HAE patient plasma from further contact activation. Error bars in the graph represent standard deviation.

DETAILED DESCRIPTION

Definitions

Figure 1:
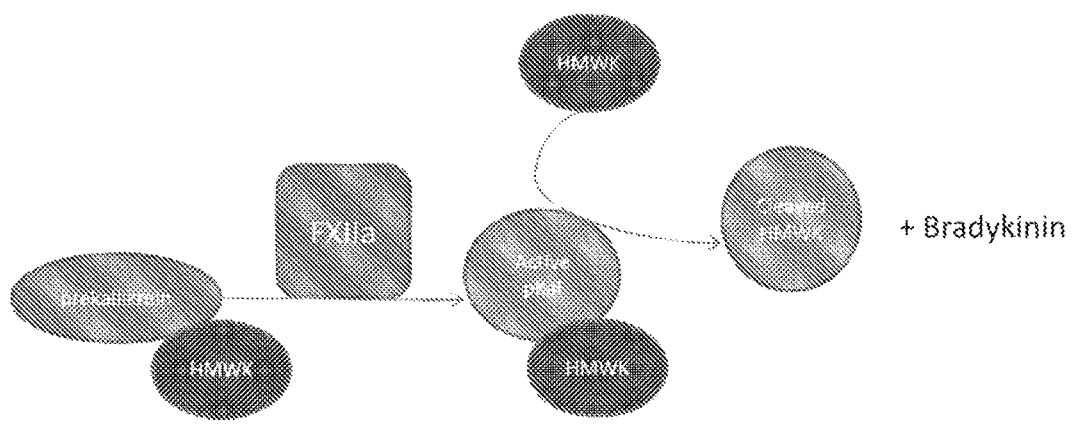
FIG. 1 is a depiction of elements involved in the contact system activation of plasma kallikrein.

For convenience, before further description of the present invention, certain terms employed in the specification, examples and appended claims are defined here. Other terms are defined as they appear in the specification.

The singular forms "a", "an", and "the" include plural references unless the context clearly dictates otherwise.

As used herein, "acquire" or "acquiring" refers to obtaining possession of a physical entity, or a value, e.g., a numerical value, by "directly acquiring" or "indirectly acquiring" the physical entity or the value. "Directly acquiring" means performing a process (e.g., performing an assay or test on a sample or "analyzing a sample" as that term is defined herein) to obtain the physical entity or value. "Indirectly acquiring" refers to receiving the physical entity or value from another party or source (e.g., a third party laboratory that directly acquired the physical entity or value). Directly acquiring a physical entity includes performing a process, e.g., analyzing a sample, that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

As used herein, "analyzing" a sample includes performing a process that involves a physical change in a sample or another substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Analyzing a sample can include performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

The term "agonist," as used herein, is meant to refer to an agent that mimics or up-regulates (e.g., potentiates or supplements) the bioactivity of a protein. An agonist can be a wild-type protein or derivative thereof having at least one bioactivity of the wild-type protein. An agonist can also be a compound which increases at least one bioactivity of a protein. An agonist can also be a compound which increases the interaction of a polypeptide with another molecule, e.g., a target peptide or nucleic acid.

The term "antagonist" as used herein is meant to refer to an agent that downregulates (e.g., suppresses or inhibits) at least one bioactivity of a protein. An antagonist can be a compound which inhibits or decreases the interaction between a protein and another molecule, e.g., a target peptide or enzyme substrate. An antagonist can also be a compound which reduces or inhibits the amount of expressed protein present. Typically, inhibiting a protein or a gene refers to reducing expression or a relevant activity of the protein or gene by at least 10% or more, for example, 20%, 30%, 40%, or 50%, 60%, 70%, 80%, 90% or more, or a decrease in expression or the relevant activity of greater than 1-fold, 2-fold, 3-fold, 4-fold, 5-fold, 10-fold, 50-fold, 100-fold or more as measured by one or more methods described herein or recognized in the art.

As used herein, "binding affinity" refers to the apparent association constant or $K_a$. The $K_a$ is the reciprocal of the dissociation constant ($K_d$). A binding protein may, for example, have a binding affinity of at least $10^5$, $10^6$, $10^7$, $10^8$, $10^9$, $10^{10}$ and $10^{11}$ $M^{-1}$ for a particular target molecule. Higher affinity binding of a binding protein to a first target relative to a second target can be indicated by a higher $K_a$ (or a smaller numerical value $K_d$) for binding the first target than the $K_a$ (or numerical value $K_d$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in TRIS-buffer (50 mM TRIS, 150 mM NaCl, 5 mM $CaCl_2$ at pH7.5). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[Bound]=N \cdot [Free]/((1/Ka)+[Free]).$$

It is not always necessary to make an exact determination of $K_a$, though, since sometimes it is sufficient to obtain a quantitative measurement of affinity, e.g., determined using a method such as ELISA or FACS analysis, is proportional to $K_a$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term "binding protein" refers to a protein that can interact with a target molecule. This term is used interchangeably with "ligand." A "plasma kallikrein binding protein" refers to a protein that can interact with (e.g., bind) plasma kallikrein, and includes, in particular, proteins that preferentially or specifically interact with and/or inhibit plasma kallikrein. A protein inhibits plasma kallikrein if it causes a decrease in the activity of plasma kallikrein as compared to the activity of plasma kallikrein in the absence of the protein and under the same conditions. In some embodiments, the plasma kallikrein binding protein is an antibody.

The term "capture reagent" refers to a moiety that binds specifically to its ligand.

As used herein, the terms "complex" or "complex formation" refer to a complex between members having a specific affinity for one another.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Motif sequences for biopolymers can include positions which can be varied amino acids. For example, the symbol "X" in such a context generally refers to any amino acid (e.g., any of the twenty natural amino acids) unless otherwise specified, e.g., to refer to any non-cysteine amino acid. Other allowed amino acids can also be indicated for example, using parentheses and slashes. For example, "(A/W/F/N/Q)" means that alanine, tryptophan, phenylalanine, asparagine, and glutamine are allowed at that particular position.

As used herein, a "detection reagent" refers to a moiety that binds to the moiety to be detected. Typically it generates a signal, e.g., fluorescence, or produces of a measurable compound.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

A first binding protein (e.g., antibody) "binds to the same epitope" as a second binding protein (e.g., antibody) if the first binding protein binds to the same site on a target compound that the second binding protein binds, or binds to a site that overlaps (e.g., 50%, 60%, 70%, 80%, 90%, or 100% overlap, e.g., in terms of amino acid sequence or other molecular feature (e.g., glycosyl group, phosphate group, or sulfate group)) with the site that the second binding protein binds.

A first binding protein (e.g., antibody) "competes for binding" with a second binding protein (e.g., antibody) if the binding of the first binding protein to its epitope decreases (e.g., by 10%, 20%, 30%, 40%, 50%, 60%, 70%, 80%, 90%, 100%, or more) the amount of the second binding protein that binds to its epitope. The competition can be direct (e.g., the first binding protein binds to an epitope that is the same as, or overlaps with, the epitope bound by the second binding protein), or indirect (e.g., the binding of the first binding protein to its epitope causes a steric change in the target compound that decreases the ability of the second binding protein to bind to its epitope).

As used herein, a "functional" biological molecule is a biological molecule in a form in which it exhibits a property and/or activity by which it is characterized.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The disclosure includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence described herein.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interest is at least 5, 10, 25, 50, 75, 80, 90, 92, 95, 98, or 99% pure on a weight-weight basis.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism such as a human or non-human animal.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

An "isolated" protein refers to a protein that is removed from at least 90% of at least one component of a natural sample from which the isolated protein can be obtained. Proteins can be "of at least" a certain degree of purity if the species or population of species of interest is at least 5, 10, 25, 50, 75, 80, 90, 92, 95, 98, or 99% pure on a weight-weight basis.

The term "kallikrein" (e.g., plasma kallikrein) refers to peptidases (enzymes that cleave peptide bonds in proteins), a subgroup of the serine protease family. Plasma kallikrein cleaves kininogen to generate kinins, potent pro-inflammatory peptides.

The term "kallikrein inhibitor" refers to any agent or molecule that inhibits kallikrein. For example, DX-88 (also referred to herein as "PEP-1") is a potent (Ki<1 nM) and specific inhibitor of plasma kallikrein (NP_000883). (See also, e.g., WO 95/21601 or WO 2003/103475).

As used herein the term "DX-2922" as used interchangeably with the term "X101-A01". Other variants of this antibody are described below.

| Antibody Identification | Description |
| --- | --- |
| X63-G06 | Non-germlined Fab discovered using ROLIC, same HC but different LC as M160-G12 |
| X81-B01 | Germlined IgG produced in HEK 293T cells |
| X101-A01 | Germlined IgG produced in CHO cells, same HC and LC sequence as X81-B01 |
| DX-2922 | Alternate nomenclature for X101-A01 |

As used herein the term "DX-2930" as used interchangeably with the term "X124-G01". Other variants of this antibody are described below.

| Antibody Identification | Description |
| --- | --- |
| M162-A04 | Non-germlined Fab discovered using phage display |
| M199-A08 | Heavy chain CDR3 varied Fab derived by affinity maturation of M162-A04 |
| X115-F02 | Germlined Fab produced in 293T cells, same variable heavy chain as X124-G01 |
| X124-G01 or DX-2930 | Germlined IgG produced in CHO cells, LC and HC sequence as X115-F02 except that the C-terminal Lys of the HC is removed in X124-G01 (also known as DX-2930). |

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as inhibitors or activators (directly or indirectly) of a functional property, biological activity or process, or combination of them, (e.g., agonist, partial antagonist, partial agonist, inverse agonist, antagonist, anti-microbial agents, inhibitors of microbial infection or proliferation, and the like) by inclusion in assays. In such assays, many modulators may be screened at one time. The activity of a modulator may be known, unknown or partially known.

A "non-essential" amino acid residue is a residue that can be altered from the wild-type sequence of the binding agent, e.g., the antibody, without abolishing or more preferably, without substantially altering a biological activity, whereas changing an "essential" amino acid residue results in a substantial loss of activity.

A "patient," "subject" or "host" (these terms are used interchangeably) to be treated by the subject method may mean either a human or non-human animal. In some embodiments, a subject is suspected of or is at risk for or suffers from a kallikrein-mediated disorder, e.g., a bradykinin-mediated disorder, e.g., hereditary angioedema (HAE). In some embodiments, a subject is at risk for or suffers from non-histamine-dependent idiopathic angioedema, rheumatoid arthritis, Crohn's disease, ulcerative colitis, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

The terms "prekallikrein" and "preplasma kallikrein" are used interchangeably herein and refer to the zymogen form of active plasma kallikrein, which is also known as prekallikrein.

The term "preventing" or to "prevent" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having)

similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher.

In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

Motif sequences for biopolymers can include positions which can be varied amino acids. For example, the symbol "X" in such a context generally refers to any amino acid (e.g., any of the twenty natural amino acids) unless otherwise specified, e.g., to refer to any non-cysteine amino acid. Other allowed amino acids can also be indicated for example, using parentheses and slashes. For example, "(A/W/F/N/Q)" means that alanine, tryptophan, phenylalanine, asparagine, and glutamine are allowed at that particular position.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. The terms "induce", "inhibit", "potentiate", "elevate", "increase", "decrease" or the like, e.g., which denote distinguishable qualitative or quantitative differences between two states, may refer to a difference, e.g., a statistically significant difference, between the two states.

As used herein, a "sample", refers to a composition that comprises tissue, e.g., blood, plasma or protein, from a subject. A sample includes both an initial unprocessed sample taken from a subject as well as subsequently processed, e.g., partially purified or preserved forms. Exemplary samples include blood, plasma, tears, or mucus. In some embodiments, the sample is a blood or plasma sample.

A "therapeutically effective dosage" preferably modulates a measurable parameter, e.g., plasma kallikrein activity, by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions. Alternatively, this property of a composition can be evaluated by examining the ability of the compound to modulate a parameter in vitro.

"Treating" a disease (or condition) in a subject or "treating" a subject having a disease refers to subjecting the subject to a pharmaceutical treatment, e.g., the administration of a drug, such that at least one symptom of the disease is cured, alleviated or decreased.

The term "preventing" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition.

"Preventing" a disease may also be referred to as "prophylaxis" or "prophylactic treatment."

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Headings, including alphabetical or numerical headings, are merely for ease of understanding and reading and, absent express indication to the contrary, do not impose temporal order or a hierarchy of preferences.

Detection of Cleaved and Intact HMWK

Plasma kallikrein circulates as an inactive zymogen called prekallikrein that is mostly bound to its substrate, high molecular weight kininogen (HMWK). In response to a stimulus, FXII is activated to FXIIa. FXIIa cleaves prekallikrein to form active plasma kallikrein (FIG. 1). Approximately 75-90% of circulating prekallikrein is bound to HMWK through a non-active site interaction with domain 6 of HMWK. Free and HMWK-bound active pKal generate cleaved HMWK and bradykinin. Biomarkers of plasma kallikrein activation are shown in Table 2. The suitability of a biomarker can be demonstrated by following its levels in the presence and absence of an acute attack of HAE. Levels of these biomarkers could also be altered during an attack of bradykinin mediated edema or other disease mediated by pKal activity. See Table 2.

TABLE 2

| | | Biomarkers associated with KMA | | |
|---|---|---|---|---|
| Biomarker | Assay | Basal Level in HAE patient relative to normal | Δ due to contact activation | Comments |
| Intact HMWK | ELISA, Western blot | Unchanged | decrease | Test are available to measure intact kininogen using APTT with kininogen deficient plasma or immunoassays: www.diapharma.com/downloads/68201025811.pdf |
| Cleaved HMWK | ELISA, Western blot | Increased | Increased | Cleaved kininogen can increase to ~47% total kininogen during an HAE attack. -Cleaved kininogen is also elevated during sepsis, cirrhosis. Assays can use either a) an antibody that is specific for cleaved kininogen as opposed to intact kininogen; or b) an assay format capable of separating and quantifying cleaved and intact kininogen (e.g. Western blot). This assay would not be sensitive to circulating anti-pKal antibody and is not dependent on whether cell surface bound active pKal is the main culprit in localized bradykinin-mediated angioedema. |

Table 2 provides markers that can be evaluated by the methods described in Table 2 and elsewhere herein to evaluate subjects for pKal or bradykinin mediated disorders. Table 2 indicates the direction in change in the level of marker associated with a pKal or bradykinin mediated disorders.

The present disclosure is based on, at least in part, the discovery that a value of a specific form of NMWK (e.g., the percentage of cleaved HMWK) in a patient sample correlates with certain pKal-mediated diseases (e.g., HAE) and autoimmune diseases (e.g., RA, UC, and Crohn's disease). Thus, a value (e.g., percentage) of cleaved HMWK, intact HMWK, or both, can be used as a biomarker for identifying subjects having or at risk for such diseases, for identifying a disorder that is likely to be susceptible to treatment with a pKal inhibitor, and for evaluating the effectiveness of a disease treatment involving one or more pKal inhibitors.

Detection Reagent

In some embodiments, a detection reagent (e.g., an antibody) that specifically (preferentially) bind to one form of HMWK as compared to the other form of HMWK can be used in the assay methods described herein for determining the level of cleaved HMWK in a sample, which can be a biological sample (e.g., a blood sample or a plasma sample) from a candidate patient. In one example, the detection reagent is an antibody specifically binding to cleaved HMWK as compared to intact HMWK. In another example, the detection reagent is an antibody specifically binding to intact HMWK as compared to the cleaved form. Alternatively or in addition, the antibody specifically binds the C-terminus of the light chain of cleaved HMWK. Such an antibody could be used to distinguish HMWK from LMWK because LMWK does not contain the C-terminal fragment of the light chain of cleaved HMWK due to alternative splicing.

A detection reagent that "specifically binds" to an antigen or an epitope is a term well understood in the art, and methods to determine such specific binding are also well known in the art. A detection reagent such as an antibody is said to exhibit "specific binding" if it reacts or associates more frequently, more rapidly, with greater duration and/or with greater affinity with a particular target antigen than it does with alternative targets. A detection reagent "specifically binds" to a target antigen (e.g., cleaved HMWK) or epitope thereof if it binds with greater affinity, avidity, more readily, and/or with greater duration than it binds to other substances (e.g., intact HMWK). For example, an antibody that specifically (or preferentially) binds to an antigen (e.g., cleaved HMWK or the C-terminus of the light chain of cleaved HMWK) or an antigenic epitope therein is an antibody that binds this target antigen with greater affinity, avidity, more readily, and/or with greater duration than it binds to other antigens (e.g., intact HMWK) or other epitopes in the same antigen. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding. In some examples, an antibody that "specifically binds" to a target antigen or an epitope thereof may not bind to other antigens or other epitopes in the same antigen.

In some embodiments, an antibody for use in the assay methods described herein has a suitable binding affinity for a target antigen or antigenic epitope (e.g., cleaved kininogen, intact HMWK, or the C-terminus of the light chain of cleaved kininogen). As used herein, "binding affinity" refers to the apparent association constant or $K_A$. The $K_A$ is the reciprocal of the dissociation constant ($K_D$). The antibody described herein may have a binding affinity ($K_D$) of at least $10^{-5}$, $10^{-6}$, $10^{-7}$, $10^{-8}$, $10^{-9}$, $10^{-10}$ M, or lower. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen relative to the second antigen. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J Immunol. 1996; 26(3):629-39.)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, see also www.hgmp.mrc.ac.uk). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, e.g., have a sequence of a framework of an antibody produced by a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH—-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242: 423-426; and Huston et al. (1988) Proc. Natl. Acad. Sci. USA 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

As used herein, a "humanized" immunoglobulin variable region refers to an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762.

The inhibition constant (Ki) provides a measure of inhibitor potency; it is the concentration of inhibitor required to reduce enzyme activity by half and is not dependent on enzyme or substrate concentrations. The apparent Ki ($K_{i,app}$) is obtained at different substrate concentrations by measuring the inhibitory effect of different concentrations of inhibitor (e.g., inhibitory binding protein) on the extent of the reaction (e.g., enzyme activity); fitting the change in pseudo-first order rate constant as a function of inhibitor concentration to the Morrison equation (Equation 1) yields an estimate of the apparent Ki value. The Ki is obtained from the y-intercept extracted from a linear regression analysis of a plot of Ki,app versus substrate concentration.

$$v = v_o - v_o\left(\frac{(K_{i,app} + I + E) - \sqrt{(K_{i,app} + I + E)^2 - 4 \cdot I \cdot E}}{2 \cdot E}\right) \quad \text{Equation 1}$$

Where v=measured velocity; $v_o$=velocity in the absence of inhibitor; $K_{i,app}$=apparent inhibition constant; I=total inhibitor concentration; and E=total enzyme concentration.

In some embodiments, the detection reagent as described herein can be conjugated to a detectable label and the binding of the detection reagent to the antigen of interest (e.g., cleaved HMWK and intact HMWK) can be determined based on the intensity of the signal released from the detectable label. Alternatively, a a secondary antibody specific to the detection reagent can be used. One or more antibodies may be coupled to a detectable label. Any suitable label known in the art can be used in the assay methods described herein. In some embodiments, a detectable label comprises a fluorophore. As used herein, the term "fluorophore" (also referred to as "fluorescent label" or "fluorescent dye") refers to moieties that absorb light energy at a defined excitation wavelength and emit light energy at a different wavelength. In some embodiments, a detection moiety is or comprises an enzyme. In some embodiments, an enzyme is one (e.g., β-galactosidase) that produces a colored product from a colorless substrate.

High Molecular-Weight Kininogen

High molecular-weight kininogen (HMWK) exists in the plasma as a single polypeptide (1-chain) multi-domain (domains 1-6) protein with a molecular weight of approximately 110 kDa (FIG. 4A). HMWK is cleaved by pKal within domain 4 to release the 9 amino acid, pro-inflammatory peptide bradykinin and a 2-chain form of HMWK (cleaved kininogen). The 2 chains of HMWK are the heavy chain, which contains the domains 1-3 of HMWK, and the light chain, which contains the domains 5 and 6 of HMWK. The heavy and light chains have a molecular weight of approximately 56 and 46 kiloDaltons, respectively. FIGS. 4A and 4B.

Intact HMWK

Intact high molecular weight kininogen (HMWK), also referred to herein as "intact kininogen," can be assayed, for example, using coagulant or immunological methods, e.g., radioimmunoassay (see, e.g., Kerbiriou-Nabias, D. M., Br J Haematol, 1984, 56(2):2734-86). A monoclonal antibody to the light chain of human HMWK is known. See, e.g., Reddigari, S. R. & Kaplan, A. P., Blood, 1999, 74:695-702. An assay for HMWK that relies on a chromogenic substrate can also be used. See, e.g., Scott, C. F. et al. Thromb Res, 1987, 48(6):685-700; Gallimore, M. J. et al. Thromb Res, 2004, 114(2):91-96.

The human gene encoding HMWK is kininogen 1 (KNG1). KNG1 is transcribed and alternatively spliced to form mRNAs that encode either HMWK or low molecular weight kininogen (LMWK). An exemplary protein sequence of HMWK is provided below:

>gi|156231037|ref|NP_001095886.1| kininogen-1
isoform 1 precursor [Homo sapiens]
(SEQ ID NO: 1)
MKLITILFLCSRLLLSLTQESQSEEIDCNDKDLFKAVDAALKKYNSQNQS

NNQFVLYRITEATKTVGSDTFYSFKYEIKEGDCPVQSGKTWQDCEYKDAA

KAATGECTATVGKRSSTKFSVATQTCQITPAEGPVVTAQYDCLGCVHPIS

TQSPDLEPILRHGIQYFNNNTQHSSLFMLNEVKRAQRQVVAGLNFRITYS

IVQTNCSKENFLFLTPDCKSLWNGDTGECTDNAYIDIQLRIASFSQNCDI

YPGKDFVQPPTKICVGCPRDIPTNSPELEETLTHTITKLNAENNATFYFK

IDNVKKARVQVVAGKKYFIDFVARETTCSKESNEELTESCETKKLGQSLD

CNAEVYVVPWEKKIYPTVNCQPLGMISLMKRPPGFSPFRSSRIGEIKEET

TVSPPHTSMAPAQDEERDSGKEQGHTRRHDWGHEKQRKHNLGHGHKHERD

QGHGHQRGHGLGHGHEQQHGLGHGHKFKLDDDLEHQGGHVLDHGHKHKHG

HGHGKHKNKGKKNGKHNGWKTEHLASSSEDSTTPSAQTQEKTEGPTPIPS

LAKPGVTVTFSDFQDSDLIATMMPPISPAPIQSDDDWIPDIQIDPNGLSF

NPISDFPDTTSPKCPGRPWKSVSEINPTTQMKESYYFDLTDGLS

Cleaved HMWK

Cleaved high molecular weight kininogen (HMWK), also referred to herein as "cleaved kininogen," can be assessed, for example, using methods described in Examples 1, and 3 to 7, e.g., Western blot. In some embodiments, the light chain of cleaved HMWK can be assessed. Antibodies that bind cleaved HMWK, such as antibodies that bind to the light chain of cleaved HMWK (e.g., an epitope comprising C-terminus residues) can be used. One example is the mouse mAb clone 11H05. Additionally, cleaved HMWK may be assessed using mass spectrometry. Immunoblotting techniques for assessing levels of cleaved HMWK are known in the art. See, e.g., Buhler R. et al. Blood Coagul Fibrinolysis, 1995, 6(3):223-232.

Exemplary sequences of the heavy and light chains of cleaved kininogen are provided below.

>cleaved kininogen-1 heavy chain
(SEQ ID NO: 2)
QESQSEEIDCNDKDLFKAVDAALKKYNSQNQSNNQFVLYRITEATKTVGS

DTFYSFKYEIKEGDCPVQSGKTWQDCEYKDAAKAATGECTATVGKRSSTK

FSVATQTCQITPAEGPVVTAQYDCLGCVHPISTQSPDLEPILRHGIQYFN

NNTQHSSLFMLNEVKRAQRQVVAGLNFRITYSIVQTNCSKENFLFLTPDC

KSLWNGDTGECTDNAYIDIQLRIASFSQNCDIYPGKDFVQPPTKICVGCP

-continued

RDIPTNSPELEETLTHTITKLNAENNATFYFKIDNVKKARVQVVAGKKYF

IDFVARETTCSKESNEELTESCETKKLGQSLDCNAEVYVVPWEKKIYPTV

NCQPLGMISLMK

>cleaved kininogen-1 light chain
(SEQ ID NO: 3)
SSRIGEIKEETTVSPPHTSMAPAQDEERDSGKEQGHTRRHDWGHEKQRKH

NLGHGHKHERDQGHGHQRGHGLGHGHEQQHGLGHGHKFKLDDDLEHQGGH

VLDHGHKHKHGHGHGKHKNKGKKNGKHNGWKTEHLASSSEDSTTPSAQTQ

EKTEGPTPIPSLAKPGVTVTFSDFQDSDLIATMMPPISPAPIQSDDDWIP

DIQIDPNGLSFNPISDFPDTTSPKCPGRPWKSVSEINPTTQMKESYYFDL

TDGLS

Assay Format

Values (e.g., the absolute amounts or levels or the relative amounts or levels such as percentages) of biomarkers disclosed herein, or changes in values of biomarkers disclosed herein, can be assessed using assays described herein and/or assays known in the art. In some embodiments, the percentage of cleaved kininogen in a sample from a subject is used in any of the methods described herein.

Assays that can be used for assessing levels of biomarkers include, e.g., immunoassays, e.g., Western blots, enzyme linked immunosorbent assays (ELISAs) (e.g., sandwich ELISAs), radioimmunoassays, electrochemiluminescence-based detection assays, and related techniques. Mass spectrometry based approaches can also be used. Assays that rely on a chromogenic substrate can also be employed. Assays, e.g., Western blot assays, may further involve use of a quantitative imaging system, e.g., LICOR imaging technology, which is commercially available (see, e.g., the Odyssey® CLx infrared imaging system from LI-COR Biosciences). In some embodiments, an electrochemiluminescence detection assay or an assay relying on a combination of electrochemiluminescence and patterned array technology is used (e.g., an ECL or MULTI-ARRAY technology assay from Meso Scale Discovery (MSD)).

As used herein, the terms "measuring" or "measurement," or alternatively "detecting" or "detection," means assessing the presence, absence, quantity or amount (which can be an effective amount) of a substance within a sample, including the derivation of qualitative or quantitative concentration levels of such substances, or otherwise evaluating the values or categorization of a subject's.

In some embodiments, provided assays can be carried out on high throughput platforms. In some embodiments, multi-well plates, e.g., 24-, 48-, 96-, 384- or greater well plates, may be used for high throughput assays. Individual assays can be carried out in each well in parallel. Therefore, it is generally desirable to use a plate reader to measure multiple wells in parallel to increase assay throughput. In some embodiments, plate readers that are capable of imaging multi-wells (e.g., 4, 16, 24, 48, 96, 384, or greater wells) in parallel can be used for this platform. For example, a commercially available plate reader (e.g., the plate::vision system available from Perkin Elmer, Waltham, Mass.) may be used. This plate reader is capable of kinetic-based fluorescence analysis. The plate::vision system has high collection efficiency optics and has special optics designed for the analysis of 96 wells in parallel. Additional suitable parallel plate readers include but are not limited to the SAFIRE (Tecan, San Jose, Calif.), the FLIPRTETRA® (Molecular Devices, Union City, Calif.), the FDSS7000 (Hamamatsu, Bridgewater, N.J.), and the CellLux (Perkin Elmer, Waltham, Mass.). In some embodiments, high throughput screening assays of the invention are automated (e.g., adapted to robotic assays).

Kits

The present disclosure also provides kits for use in evaluating cleaved and/or intact kininogen in samples containing such, e.g., biological samples from human patients. Such kits can comprise a detection reagent specifically bind to either the cleaved kininogen or the intact kininogen as compared to the other form, and optionally, cleaved kininogen and/or intact kininogen as controls. In some embodiments, the kits further comprise secondary antibodies and/or reagents for detecting binding of the detection reagent to the cleaved and/or intact kininogen.

In some embodiments, the kit can comprise instructions for use in accordance with any of the methods described herein. The included instructions can comprise a description of how to use the components contained in the kit for measuring the level of cleaved and/or intact kininogen in a sample, which can be a biological sample collected from a human patient.

The instructions relating to the use of the kit generally include information as to the amount of each component and suitable conditions for performing the assay methods described herein. The components in the kits may be in unit doses, bulk packages (e.g., multi-dose packages), or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the kit is used for evaluating the level of cleaved and/or intact kininogen. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the present disclosure provides articles of manufacture comprising contents of the kits described above.

Application of Assay Methods in Disease Diagnosis and Prognosis

The assay methods and kits described herein can be applied for evaluation of disease, e.g., diagnosis or prognosis of a disease. Evaluation may include identifying a subject as being at risk for or having a disease as described herein, e.g., a pKal-mediated disorder such as HAE and an autoimmune disease such as RA, UC, and Crohn's disease. Evaluation may also include monitoring treatment of a disease, such as evaluating the effectiveness of a treatment for a PKal-mediated disorder such as HAE. Further, evaluation may include identifying a disease that can be treated by a pKal inhibitor.

A. Diagnosis

In some embodiments, the assay methods and kits are performed to determine the level of cleaved kininogen and/or intact kininogen in a biological sample (e.g., a blood sample or a plasma sample) collected from a candidate subject (e.g., a human patient suspected of having a PKal-mediated disorder such as HAE or an autoimmune disease such as RA, UC, and Crohn's disease). The level of cleaved kininogen can then be compared with either the intact kininogen or the total amount of kininogen in the sample to determine a value (e.g., percentage) of cleaved kininogen, a value of intact kininogen, or both, in the sample. The value of cleaved kininogen and/or intact kininogen can be compared to a reference value to determine whether the subject has or is at risk for the PKal-mediated disorder, e.g., HAE or an autoimmune disease, such as RA, UC, and Crohn's disease. For example, if the percentage of cleaved kininogen is at or higher than a reference number, the subject can be identified as having or at risk for a pKal-mediated disorder such as HAE, RA, UC, and Crohn's disease. Alternatively, if the percentage of intact kininogen is at or lower than a reference number, the subject can be identified as having or at risk for a pKal-mediated disorder such as HAE, RA, UC, and Crohn's disease.

The reference value can be a control level of cleaved kininogen percentage. In some embodiments, the control level is the percentage of cleaved kininogen in a control sample, such as a sample (e.g., blood or plasma sample) obtained from a healthy subject or population of healthy subjects, which preferably are of the same species as the candidate subject. As used herein, a healthy subject is a subject that is apparently free of the target disease (e.g., a PKal-mediated disorder such as HAE or autoimmune diseases such as RA, US, and Crohn's disease) at the time the level of cleaved and/or intact kininogen is measured or has no history of the disease.

The control level can also be a predetermined level. Such a predetermined level can represent the percentage of cleaved kininogen in a population of subjects that do not have or are not at risk for the target disease. It can also represent the percentage of cleaved kininogen in a population of subjects that have the target disease.

The predetermined level can take a variety of forms. For example, it can be single cut-off value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the percentages of cleaved kininogen in a control population within a predetermined percentile.

The control level as described herein can be determined by routine technology. In some examples, the control level can be obtained by performing a conventional method (e.g., the same assay for obtaining the level of cleaved and/or intact kininogen in a test sample as described herein) on a control sample as also described herein. In other examples, levels of cleaved and/or intact kininogen can be obtained from members of a control population and the results can be analyzed by, e.g., a computational program, to obtain the control level (a predetermined level) that represents the level of cleaved and/or intact kininogen in the control population.

By comparing the percentage of cleaved kininogen in a sample obtained from a candidate subject to the reference value as described herein, it can be determined as to whether the candidate subject has or is at risk for the PKal-mediated disease (e.g., HAE or an autoimmune disease such as RA, UC, and Crohn's disease). For example, if the percentage of cleaved kininogen in a sample of the candidate subject deviates from the reference value (e.g., increased as compared to the reference value), the candidate subject might be identified as having or at risk for the disease. When the reference value represents represent the percentage range of cleaved kininogen in a population of subjects that have the target disease, the percentage of cleaved kininogen in a sample of a candidate falling in the range indicates that the candidate subject has or is at risk for the target disease.

As used herein, "an elevated level or a level above a reference value" means that the level/percentage of cleaved kininogen is higher than a reference value, such as a pre-determined threshold of a level/percentage of cleaved kininogen in a control sample. Control levels are described in detail herein. An elevated percentage of cleaved kininogen includes a cleaved kininogen percentage that is, for example, 1%, 5%, 10%, 20%, 30%, 40%, 50%, 60%, 70%, 80%, 90%, 100%, 150%, 200%, 300%, 400%, 500% or more above a reference value. An elevated percentage of cleaved kininogen also includes increasing a phenomenon from a zero state (e.g., no or undetectable cleaved kininogen and/or intact kininogen that binds to a capture reagent in a sample) to a non-zero state (e.g., some or detectable cleaved kininogen and/or intact kininogen).

As used herein, "a decreased percentage/level or a percentage/level below a reference value" means that the percentage/level of cleaved is lower than a reference value, such as a pre-determined threshold of cleaved kininogen in a control sample. Control levels are described in detail herein. An decreased level of cleaved kininogen includes a cleaved kininogen that is, for example, 1%, 5%, 10%, 20%, 30%, 40%, 50%, 60%, 70%, 80%, 90%, 100%, 150%, 200%, 300%, 400%, 500% or more lower than a reference value. A decreased level of cleaved kininogen that binds to a capture reagent also includes decreasing a phenomenon from a non-zero state (e.g., some or detectable cleaved kininogen in a sample) to a zero state (e.g., no or undetectable cleaved kininogen in a sample).

In some embodiments, the candidate subject is a human patient having a symptom of a pKal-mediated disorder, e.g., such as HAE or an autoimmune disease such as RA, UC, and Crohn's disease. For example, the subject has edema, swelling wherein said swelling is completely or predominantly peripheral; hives; redness, pain, and swelling in the absence of evidence of infection; non-histamine-mediated edema, recurrent attacks of swelling, or a combination thereof. In other embodiments, the subject has no symptom of a pKal-mediated disorder at the time the sample is collected, has no history of a symptom of a pKal-mediated disorder, or no history of a pKal-mediated disorder such as HAE. In yet other embodiments, the subject is resistant to an antihistamine therapy, a corticosteroid therapy, or both.

(i) HAE

In some embodiments, the disease or condition that involves plasma kallikrein activity is hereditary angioedema (HAE). Hereditary angioedema (HAE) is also known as "Quincke edema," C1 esterase inhibitor deficiency, C1 inhibitor deficiency, and hereditary angioneurotic edema (HANE). HAE is characterized by recurrent episodes of severe swelling (angioedema), which can affect, e.g., the limbs, face, genitals, gastrointestinal tract, and airway. Symptoms of HAE include, e.g., swelling in the arms, legs, lips, eyes, tongue, and/or throat; airway blockage that can involve throat swelling and sudden hoarseness; repeat episodes of abdominal cramping without obvious cause; and/or swelling of the intestines, which can be severe and can lead to abdominal cramping, vomiting, dehydration, diarrhea, pain, and/or shock. About one-third of individuals with this HAE develop a non-itchy rash called *erythema marginatum* during an attack.

Swelling of the airway can be life threatening and causes death in some patients. Mortality rates are estimated at 15-33%. HAE leads to about 15,000-30,000 emergency department visits per year.

Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm.nih.gov/condition/hereditary-angioedema). The frequency and duration of attacks vary greatly among people with hereditary angioedema, even among people in the same family.

There are three types of HAE, known as types I, II, and III. It is estimated that HAE affects 1 in 50,000 people, that type I accounts for about 85 percent of cases, type II accounts for about 15 percent of cases, and type III is very rare. Type III is the most newly described form and was originally thought to occur only in women, but families with affected males have been identified.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Without the proper levels of functional C1 inhibitor, excessive amounts of bradykinin are generated. Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III. The F12 gene provides instructions for making coagulation factor XII. In addition to playing a critical role in blood clotting (coagulation), factor XII is also an important stimulator of inflammation and is involved in the production of bradykinin. Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When hereditary angioedema is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. Patient. 2012; 5(2):113-26.

(ii) Rheumatoid Arthritis

Rheumatoid arthritis (RA) is an autoimmune, chronic inflammatory disease that causes joint swelling and pain and normally results in joint destruction. RA generally follows a relapsing/remitting course, with "flares" of disease activity interspersed with remissions of disease symptoms. RA is associated with a number of additional inflammatory disorders, including Sjogren's syndrome (dry eyes and mouth caused by inflammation of tear and saliva glands), pleuritis (inflammation of the pleura that causes pain upon deep breath and coughing), rheumatoid nodules (nodular sites of inflammation that develop within the lungs), pericarditis (inflammation of the pericardium that causes pain when lying down or leaning forward), Felty syndrome (splenomegaly and leucopenia observed in conjunction with RA, making the subject prone to infection), and vasculitis (an inflammation of the blood vessels which can block blood flow). Plasma kallikrein has been implicated in rheumatoid arthritis.

Symptoms of active RA include fatigue, lack of appetite, low grade fever, muscle and joint aches, and stiffness. Muscle and joint stiffness are usually most notable in the morning and after periods of inactivity. During flares, joints frequently become red, swollen, painful, and tender, generally as a consequence of synovitis.

Treatment for rheumatoid arthritis involves a combination of medications, rest, joint strengthening exercises, and joint protection. Two classes of medications are used in treating rheumatoid arthritis: anti-inflammatory "first-line drugs," and "Disease-Modifying Antirheumatic Drugs" (DMARDs). The first-line drugs include NSAIDS (e.g., aspirin, naproxen, ibuprofen, and etodolac) and cortisone (corticosteroids). DMARDs, such as gold (e.g., gold salts, gold thioglucose, gold thiomalate, oral gold), methotrexate, sulfasalazine, D-penicillamine, azathioprine, cyclophosphamide, chlorambucil, and cyclosporine, leflunomide, etanercept, infliximab, anakinra, and adalimumab, and hydroxychloroquine, promote disease remission and prevent progressive joint destruction, but they are not anti-inflammatory agents.

Scales useful for assessing RA and symptoms of RA include, e.g., the Rheumatoid Arthritis Severity Scale (RASS; Bardwell et al., (2002) *Rheumatology* 41(1):38-45), SF-36 Arthritis Specific Health Index (ASHI; Ware et al., (1999) *Med. Care.* 37(5 Suppl):MS40-50), Arthritis Impact Measurement Scales or Arthritis Impact Measurement Scales 2 (AIMS or AIMS2; Meenan et al. (1992) *Arthritis Rheum.* 35(1):1-10); the Stanford Health Assessment Questionnaire (HAQ), HAQII, or modified HAQ (see, e.g., Pincus et al. (1983) *Arthritis Rheum.* 26(11):1346-53).

(iii) Intestinal Bowel Disease (IBD)—Crohn's disease and ulcerative colitis Inflammatory bowel disease (IBD) is a group of inflammatory conditions of the large intestine and, in some cases, the small intestine. The main forms of IBD are Crohn's disease and ulcerative colitis (UC). Accounting for far fewer cases are other forms of IBD: collagenous colitis, lymphocytic colitis, ischaemic colitis, diversion colitis, Behçet's syndrome, infective colitis, and indeterminate colitis. The main difference between Crohn's disease and UC is the location and nature of the inflammatory changes. Crohn's can affect any part of the gastrointestinal tract, from mouth to anus (skip lesions), although a majority of the cases start in the terminal ileum. Ulcerative colitis, in contrast, is restricted to the colon and the rectum. Microscopically, ulcerative colitis is restricted to the mucosa (epithelial lining of the gut), while Crohn's disease affects the whole bowel wall. Finally, Crohn's disease and ulcerative colitis present with extra-intestinal manifestations (such as liver problems, arthritis, skin manifestations and eye problems) in different proportions.

Symptoms of IBD include abdominal pain, vomiting, diarrhea, hematochezia, weight loss, weight gain and various associated complaints or diseases (arthritis, pyoderma gangrenosum, primary sclerosing cholangitis). Diagnosis is generally by colonoscopy with biopsy of pathological lesions.

Treatment for IBD, depending on the level of severity, may require immunosuppression to control the symptoms. Immunosuppresives such as azathioprine, methotrexate, or 6-mercaptopurine can be used. More commonly, treatment of IBD requires a form of mesalamine. Often, steroids are used to control disease flares and were once acceptable as a maintenance drug. Biologicals, such as infliximab, have been used to treat patients with Crohn's disease or Ulcerative Colitis. Severe cases may require surgery, such as bowel resection, strictureplasty or a temporary or permanent colostomy or ileostomy. Alternative medicine treatments for IBD exist in various forms however such methods concentrate on controlling underlying pathology in order to avoid prolonged steroidal exposure or surgical excision. Usually the treatment is started by administering drugs, such as prednisone, with high anti-inflammatory affects. Once the inflammation is successfully controlled, the patient is usually switched to a lighter drug, such as asacol—a mesalamine—to keep the disease in remission. If unsuccessful, a combination of the aforementioned immunosuppressant drugs with a mesalamine (which may also have an anti-inflammatory effect) may or may not be administered, depending on the patient.

(iv) Other pKal-Mediated or Bradykinin-Mediated Disorders

Other exemplary diseases or conditions associated with plasma kallikrein activity include non-histamine-dependent idiopathic angioedema, rheumatoid arthritis, Crohn's disease, ulcerative colitis, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

A subject who is identified as having or at risk for a PKal-mediated disorder as described herein can be subjected to a suitable treatment such as those described herein.

B. Evaluate Treatment Effectiveness

The assay methods described herein can also be applied to evaluate the effectiveness of a treatment for a PKal-mediated disorder (e.g., HAE). For examples, multiple biological samples (e.g., blood or plasma samples) can be collected from a subject to whom a treatment is performed either before and after the treatment or during the course of the treatment. The levels of cleaved and/or intact kininogen can be measured by any of the assay methods as described herein and values (e.g., percentages) of cleaved and/or intact kininogen can be determined accordingly. If the percentage of the cleaved kininogen decreases after the treatment or over the course of the treatment (the cleaved kininogen percentage in a later collected sample as compared to that in an earlier collected sample) or the percentage of intact kininogen increases after the treatment or over the course of the treatment, it indicates that the treatment is effective. In some examples, the treatment involves a therapeutic agent, such as a kallikrein binding agent as described herein, a bradykinin B2 receptor antagonist as described herein, or a C1-INH replacement agent as described herein. Examples of the therapeutic agents include, but not limited to, DX-2930 or DX88.

If the subject is identified as not responsive to the treatment, a higher dose and/or frequency of dosage of the therapeutic agent are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

Identification of Disorders Susceptible to Treatment with pKal Inhibitors

The values of cleaved kininogen and/or intact kininogen can also be relied on to identify a disorder that may be treatable by a pKal inhibitor. To practice this method, the level of cleaved kiniogen and/or the level of intact kininogen in a sample collected from a subject (e.g., a blood sample or a plasma sample) having a target disease can be measured by a suitable assay, e.g., those described herein such as a Western blot assay. Values such as percentages of the cleaved and/or intact kininogen can be determined as described herein. The values of cleaved kininogen and/or intact kininogen can be compared with a reference value as described herein. If the value of cleaved kininogen/intact kininogen deviates from the reference value (e.g., elevated or decreased), it indicates that a pKal inhibitor may be effective in treating the disease. For example, if the percentages of cleaved kininogen are decreasing after the treatment or over the course of the treatment, the treatment can be identified as being effective. Alternatively, if the percentages of intact kininogen are increasing after the treatment or over the course of the treatment, the treatment is identified as being effective.

In some embodiments, the level of cleaved and/or intact kininogen can be measured using a detection reagent (e.g., an antibody) specifically binds to either cleaved kininogen or intact kininogen as compared to the other form of kininogen. In some examples, the antibody specifically binds cleaved kininogen as compared to intact kininogen. In other examples, the antibody specifically binds the C-terminus of the light chain of cleaved kininogen.

If the disease is identified as being susceptible (can be treated by) to a pKal inhibitor, the method can further comprise administering to the subject having the disease an effective amount of a pKal inhibitor, e.g., DX-88, EPIKAL-2, or DX-2930.

Treatment

A subject at risk for or suffering from (e.g., having) a pKal-mediated or bradykinin-mediated disorder, as identified by any of the methods described herein, may be treated with any appropriate therapeutic agent. In some embodiments, provided methods include selecting a treatment for a subject based on the output of a provided assay, e.g., biomarker detection.

In some embodiments, the method comprises one or both of selecting or administering a therapeutic agent, e.g., a kallikrein binding agent as described herein, e.g., a bradykinin B2 receptor antagonist as described herein, e.g., a C1-INH replacement agent as described herein, for administration to the subject based on the output of the assay, e.g., biomarker detection.

In some embodiments a plasma kallikrein binding protein or polypeptide is administered to a subject. In some embodiments, the kallikrein binding agent is a kallikrein inhibitor, e.g., peptide, a small molecule inhibitor, a kallikrein antibody, or a fragment thereof. In some embodiments, an antagonist of bradykinin B2 receptor is administered to a subject. In some embodiments, a C1-INH replacement therapeutic agent is administered to a subject.

The therapeutic agent, e.g., kallikrein inhibitor, e.g., bradykinin B2 receptor antagonist, e.g., C1-INH replacement agent, may be administered along with another therapy as part of a combination therapy for treatment of the disease or condition that involves plasma kallikrein and/or bradykinin activity. Combination therapy, e.g., with one or more of a kallikrein inhibitor, bradykinin B2 receptor antagonist, or C1-INH replacement agent, e.g., with one or more of a kallikrein inhibitor, bradykinin B2 receptor antagonist or C1-INH replacement agent and another therapy, may be provided in multiple different configurations. The first agent may be administered before or after the administration of the other therapy. In some situations, the first agent and another therapy (e.g., a therapeutic agent) are administered concurrently, or in close temporal proximity (e.g., a short time interval between the injections, such as during the same treatment session). The first agent and the other therapy may also be administered at greater temporal intervals.

Plasma Kallikrein Binding Agents

Plasma kallikrein binding agents (e.g., binding proteins, e.g., polypeptides, e.g., inhibitory polypeptides, e.g., antibodies, e.g., inhibitory antibodies, or other binding agents, e.g., small molecules) are useful therapeutic agents for a variety of diseases and conditions, e.g., diseases and conditions that involve plasma kallikrein activity. For example, in some embodiments, the disease or condition that involves plasma kallikrein activity is hereditary angioedema (HAE). In some embodiments a plasma kallikrein binding protein or polypeptide is administered to a subject at risk or suffering from a pKal-mediated or bradykinin-mediated disorder.

A number of useful protein inhibitors of kallikrein, either tissue and/or plasma kallikrein, include a Kunitz domain. As used herein, a "Kunitz domain" is a polypeptide domain having at least 51 amino acids and containing at least two, and preferably three, disulfides. The domain is folded such that the first and sixth cysteines, the second and fourth, and the third and fifth cysteines form disulfide bonds (e.g., in a Kunitz domain having 58 amino acids, cysteines can be present at positions corresponding to amino acids 5, 14, 30, 38, 51, and 55, according to the number of the BPTI homologous sequences provided below, and disulfides can form between the cysteines at position 5 and 55, 14 and 38, and 30 and 51), or, if two disulfides are present, they can form between a corresponding subset of cysteines thereof. The spacing between respective cysteines can be within 7, 5, 4, 3, 2, 1 or 0 amino acids of the following spacing between positions corresponding to: 5 to 55, 14 to 38, and 30 to 51, according to the numbering of the BPTI sequence provided below. The BPTI sequence can be used as a reference to refer to specific positions in any generic Kunitz domain. Comparison of a Kunitz domain of interest to BPTI can be performed by identifying the best fit alignment in which the number of aligned cysteines in maximized.

The 3D structure (at high resolution) of the Kunitz domain of BPTI is known. One of the X-ray structures is deposited in the Brookhaven Protein Data Bank as "6PTI". The 3D structure of some BPTI homologues (Eigenbrot et al., (1990) Protein Engineering, 3(7):591-598; Hynes et al., (1990) Biochemistry, 29:10018-10022) are known. At least eighty one Kunitz domain sequences are known. Known human homologues include three Kunitz domains of LACI also known as tissue factor pathway inhibitor (TFPI) (Wun et al., (1988) J. Biol. Chem. 263(13):6001-6004; Girard et al., (1989) Nature, 338:518-20; Novotny et al, (1989) J. Biol. Chem., 264(31):18832-18837) two Kunitz domains of Inter-α-Trypsin Inhibitor, APP-I (Kido et al., (1988) J. Biol. Chem., 263(34):18104-18107), a Kunitz domain from collagen, three Kunitz domains of TFPI-2 (Sprecher et al., (1994) PNAS USA, 91:3353-3357), the Kunitz domains of hepatocyte growth factor activator inhibitor type 1, the Kunitz domains of Hepatocyte growth factor activator inhibitor type 2, the Kunitz domains described in U.S. Patent Publication No.: 2004-0152633. LACI is a human serum phosphoglycoprotein with a molecular weight of 39 kDa (amino acid sequence in Table 1) containing three Kunitz domains.

TABLE 1

Exemplary Natural Kunitz Domains

```
LACI:
(SEQ ID    1 MIYTMKKVHA LWASVCLLLN LAPAPLNAds eedeehtiit dtelpplklM
NO. 4)    51 HSFCAFKADD GPCKAIMKRF FFNIFTRQCE EFIYGGCEGN QNRFESLEEC
         101 KKMCTRDnan riikttlqqe kpdfCfleed pqiCrqyitr yfynnqtkqC
         151 erfkyqgClq nmnnfetlee CkniCedqpn gfqvdnygtq lnavnnsltp
         201 qstkvpslfe fhgpswCltp adrglCrane nrfyynsvig kCrpfkysgC
         251 ggnennftsk geClraCkkg figriskggl iktkrkrkkq rvkiayeeif
         301 vknm
The signal sequence (1-28) is uppercase and underscored
LACI-K1 (50-107) is uppercase
LACI-K2 (121-178) is underscored
LACI-K3 (211-270) is bold BPTI             1          2          3          4          5
(SEQ ID   12345678901234567890123456789012345678901234567890123456780
NO: 5)    RPDFCLEPPYTGPCKARIIRYFYNAKAGLCQTFVYGGCRAKRNNFKSAEDCMRTCGGA
```

The Kunitz domains above are referred to as LACI-K1 (residues 50 to 107), LACI-K2 (residues 121 to 178), and LACI-K3 (213 to 270). The cDNA sequence of LACI is reported in Wun et al. (J. Biol. Chem., 1988, 263(13):6001-6004). Girard et al. (Nature, 1989, 338:518-20) reports mutational studies in which the P1 residues of each of the three Kunitz domains were altered. LACI-K1 inhibits Factor VIIa (F.VIIa) when F.VIIa is complexed to tissue factor and LACI-K2 inhibits Factor Xa.

Proteins containing exemplary Kunitz domains include the following, with SWISS-PROT Accession Numbers in parentheses:

| A4_HUMAN | (P05067), | A4_MACFA | (P53601), | A4_MACMU | (P29216), |
|---|---|---|---|---|---|
| A4_MOUSE | (P12023), | A4_RAT | (P08592), | A4_SAISC | (Q95241), |
| AMBP_PLEPL | (P36992), | APP2_HUMAN | (Q06481), | APP2_RAT | (P15943), |
| AXP1_ANTAF | (P81547), | AXP2_ANTAF | (P81548), | BPT1_BOVIN | (P00974), |
| BPT2_BOVIN | (P04815), | CA17_HUMAN | (Q02388), | CA36_CHICK | (P15989), |
| CA36_HUMAN | (P12111), | CRPT_BOOMI | (P81162), | ELAC_MACEU | (O62845), |
| ELAC_TRIVU | (Q29143), | EPPI_HUMAN | (O95925), | EPPI_MOUSE | (Q9DA01), |
| HTIB_MANSE | (P26227), | IBP_CARCR | (P00993), | IBPC_BOVIN | (P00976), |
| IBPI_TACTR | (P16044), | IBPS_BOVIN | (P00975), | ICS3_BOMMO | (P07481), |
| IMAP_DROFU | (P11424), | IP52_ANESU | (P10280), | ISC1_BOMMO | (P10831), |
| ISC2_BOMMO | (P10832), | ISH1_STOHE | (P31713), | ISH2_STOHE | (P81129), |
| ISIK_HELPO | (P00994), | ISP2_GALME | (P81906), | IVB1_BUNFA | (P25660), |

-continued

| | | | | | |
|---|---|---|---|---|---|
| IVB1_BUNMU | (P00987), | IVB1_VIPAA | (P00991), | IVB2_BUNMU | (P00989), |
| IVB2_DABRU | (P00990), | IVB2_HEMHA | (P00985), | IVB2_NAJNI | (P00986), |
| IVB3_VIPAA | (P00992), | IVBB_DENPO | (P00983), | IVBC_NAJNA | (P19859), |
| IVBC_OPHHA | (P82966), | IVBE_DENPO | (P00984), | IVBI_DENAN | (P00980), |
| IVBI_DENPO | (P00979), | IVBK_DENAN | (P00982), | IVBK_DENPO | (P00981), |
| IVBT_ERIMA | (P24541), | IVBT_NAJNA | (P20229), | MCPI_MELCP | (P82968), |
| SBPI_SARBU | (P26228), | SPT3_HUMAN | (P49223), | TKD1_BOVIN | (Q28201), |
| TKD1_SHEEP | (Q29428), | TXCA_DENAN | (P81658), | UPTI_PIG | (Q29100), |
| AMBP_BOVIN | (P00978), | AMBP_HUMAN | (P02760), | AMBP_MERUN | (Q62577), |
| AMBP_MESAU | (Q60559), | AMBP_MOUSE | (Q07456), | AMBP_PIG | (P04366), |
| AMBP_RAT | (Q64240), | IATR_HORSE | (P04365), | IATR_SHEEP | (P13371), |
| SPT1_HUMAN | (O43278), | SPT1_MOUSE | (Q9R097), | SPT2_HUMAN | (O43291), |
| SPT2_MOUSE | (Q9WU03), | TFP2_HUMAN | (P48307), | TFP2_MOUSE | (O35536), |
| TFPI_HUMAN | (P10646), | TFPI_MACMU | (Q28864), | TFPI_MOUSE | (O54819), |
| TFPI_RABIT | (P19761), | TFPI_RAT | (Q02445), | YN81_CAEEL | (Q03610) |

A variety of methods can be used to identify a Kunitz domain from a sequence database. For example, a known amino acid sequence of a Kunitz domain, a consensus sequence, or a motif (e.g., the ProSite Motif) can be searched against the GenBank sequence databases (National Center for Biotechnology Information, National Institutes of Health, Bethesda Md.), e.g., using BLAST; against Pfam database of HMMs (Hidden Markov Models) (e.g., using default parameters for Pfam searching; against the SMART database; or against the ProDom database. For example, the Pfam Accession Number PF00014 of Pfam Release 9 provides numerous Kunitz domains and an HMM for identify Kunitz domains. A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314. The SMART database (Simple Modular Architecture Research Tool, EMBL, Heidelberg, DE) of HMMs as described in Schultz et al. (1998), *Proc. Natl. Acad. Sci. USA* 95:5857 and Schultz et al. (2000) *Nucl. Acids Res* 28:231. The SMART database contains domains identified by profiling with the hidden Markov models of the HMMer2 search program (R. Durbin et al. (1998) *Biological sequence analysis: probabilistic models of proteins and nucleic acids.* Cambridge University Press). The database also is annotated and monitored. The ProDom protein domain database consists of an automatic compilation of homologous domains (Corpet et al. (1999), *Nucl. Acids Res.* 27:263-267). Current versions of ProDom are built using recursive PSI-BLAST searches (Altschul et al. (1997) *Nucleic Acids Res.* 25:3389-3402; Gouzy et al. (1999) *Computers and Chemistry* 23:333-340.) of the SWISS-PROT 38 and TREMBL protein databases. The database automatically generates a consensus sequence for each domain. Prosite lists the Kunitz domain as a motif and identifies proteins that include a Kunitz domain. See, e.g., Falquet et al. *Nucleic Acids Res.* 30:235-238 (2002).

Kunitz domains interact with target protease using, primarily, amino acids in two loop regions ("binding loops"). The first loop region is between about residues corresponding to amino acids 13-20 of BPTI. The second loop region is between about residues corresponding to amino acids 31-39 of BPTI. An exemplary library of Kunitz domains varies one or more amino acid positions in the first and/or second loop regions. Particularly useful positions to vary, when screening for Kunitz domains that interact with kallikrein or when selecting for improved affinity variants, include: positions 13, 15, 16, 17, 18, 19, 31, 32, 34, and 39 with respect to the sequence of BPTI. At least some of these positions are expected to be in close contact with the target protease. It is also useful to vary other positions, e.g., positions that are adjacent to the aforementioned positions in the three-dimensional structure.

The "framework region" of a Kunitz domain is defined as those residues that are a part of the Kunitz domain, but specifically excluding residues in the first and second binding loops regions, i.e., about residues corresponding to amino acids 13-20 of BPTI and 31-39 of BPTI. Conversely, residues that are not in the binding loop may tolerate a wider range of amino acid substitution (e.g., conservative and/or non-conservative substitutions).

In one embodiment, these Kunitz domains are variant forms of the looped structure including Kunitz domain 1 of human lipoprotein-associated coagulation inhibitor (LACI) protein. LACI contains three internal, well-defined, peptide loop structures that are paradigm Kunitz domains (Girard, T. et al., 1989. Nature, 338:518-520). Variants of Kunitz domain 1 of LACI described herein have been screened, isolated and bind kallikrein with enhanced affinity and specificity (see, for example, U.S. Pat. Nos. 5,795,865 and 6,057,287). These methods can also be applied to other Kunitz domain frameworks to obtain other Kunitz domains that interact with kallikrein, e.g., plasma kallikrein. Useful modulators of kallikrein function typically bind and/or inhibit kallikrein, as determined using kallikrein binding and inhibition assays.

In some aspects, a kallikrein binding agent (e.g., binding protein, e.g., polypeptide, e.g., inhibitory polypeptides, e.g., antibody, e.g., inhibitory antibody, or other binding agent, e.g., small molecule) binds to the active form of plasma kallikrein. In some embodiments, the kallikrein binding agent, binds to and inhibits plasma kallikrein, e.g., human plasma kallikrein and/or murine kallikrein.

Plasma kallikrein binding proteins can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')2 or scFv fragment). The binding protein can include two heavy chain immunoglobulins and two light chain immunoglobulins, or can be a single chain antibody. Plasma kallikrein binding proteins can be recombinant proteins such as humanized, CDR grafted, chimeric, deimmunized, or in vitro generated antibodies, and may optionally include constant regions derived from human germline immunoglobulin sequences. In one embodiment, the plasma kallikrein binding protein is a monoclonal antibody.

In some embodiments, the kallikrein binding protein binds to and inhibits plasma kallikrein, e.g., human plasma kallikrein and/or murine kallikrein. Exemplary plasma kallikrein binding proteins are disclosed in U.S. Publication No. 20120201756, the entire contents of which are incorporated herein by reference. In some embodiments, the kallikrein binding protein is an antibody (e.g., a human antibody) having the light and/or heavy chains of antibodies selected from the group consisting of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04. In some embodiments, the plasma kallikrein binding protein competes with or binds the same epitope as M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04. In some embodiments, the plasma kallikrein binding protein is DX-2930.

The heavy chain and light chain variable region sequences of DX-2930 are provided below.

```
DX-2930 Heavy chain variable region:
                                       (SEQ ID NO: 6)
EVQLLESGGGLVQPGGSLRLSCAASGFTFSHYIMMWVRQAPGKGLEWVSG

IYSSGGITVYADSVKGRFTISRDNSKNTLYLQMNSLRAEDTAVYYCAYRR

IGVPRRDEFDIWGQGTMVTVSS

DX-2930 Light chain variable region:
                                       (SEQ ID NO: 7)
DIQMTQSPSTLSASVGDRVTITCRASQSISSWLAWYQQKPGKAPKLLIYK

ASTLESGVPSRFSGSGSGTEFTLTISSLQPDDFATYYCQQYNTYWTFGQG

TKVEI
```

In some aspects, a kallikrein binding polypeptide (e.g., inhibitory polypeptide) that binds to the active form of plasma kallikrein. Exemplary polypeptide plasma kallikrein agents are disclosed in U.S. Pat. Nos. 5,795,865, 5,994,125, 6,057,287, 6,333,402, 7,628,983, and 8,283,321, 7,064,107, 7,276,480, 7,851,442, 8,124,586, 7,811,991, and U.S. Publication No. 20110086801, the entire contents of each of which is incorporated herein by reference. In some embodiments, the kallikrein binding polypeptide is DX-88 (a non-naturally occurring kallikrein inhibitor, also known as KALBITOR® (ecallantide), SEQ ID NO:8). In some embodiments, the kallikrein inhibitor comprises or consists of an about 58-amino acid sequence of amino acids 3-60 of SEQ ID NO:8 or the DX-88 polypeptide having the 60-amino acid sequence of SEQ ID NO:8.

```
                                       (SEQ ID NO: 8)
Glu Ala Met His Ser Phe Cys Ala Phe Lys Ala Asp

Asp Gly Pro Cys Arg Ala Ala His Pro Arg Trp Phe

Phe Asn Ile Phe Thr Arg Gln Cys Glu Glu Phe Ile

Tyr Gly Gly Cys Glu Gly Asn Gln Asn Arg Phe Glu

Ser Leu Glu Glu Cys Lys Lys Met Cys Thr Arg Asp
```

In some embodiments, the plasma kallikrein binding protein is EPIKAL-2 (SEQ ID NO:9), which is non-naturally occurring kallikrein inhibitor having a 58 residue amino acid sequence (corresponding to residues 3-60 of SEQ ID NO:8) and having amino acid substitutions of ILe to Ser at residue 34 and Glu to Gly at residue 39. The sequence of EPIKAL-2 is shown below:

```
                                       (SEQ ID NO: 9)
EpiKal2: Met His Ser Phe Cys Ala Phe Lys Ala Asp

Asp Gly Pro Cys Arg Ala Ala His Pro Arg Trp Phe

Phe Asn Ile Phe Thr Arg Gln Cys Glu Glu Phe Ser

Tyr Gly Gly Cys Gly Gly Asn Gln Asn Arg Phe Glu

Ser Leu Glu Glu Cys Lys Lys Met Cys Thr Arg Asp
```

In some embodiments, a plasma kallikrein binding protein can have about 85%, 90%, 91%, 92%, 93%, 94%, 95%, 96%, 97%, 98%, 99% or higher sequence identity to a binding protein described herein. In some embodiments, a plasma kallikrein binding protein can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to a binding protein described herein. In some embodiments, a plasma kallikrein binding protein can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to a binding protein described herein. In some embodiments, a plasma kallikrein binding protein can have about 85%, 90%, 91%, 92%, 93%, 94%, 95%, 96%, 97%, 98%, 99% or higher sequence identity in the constant region (e.g., CH1, CH2, CH3, and/or CL1) to a binding protein described herein.

In some aspects, a small molecule binds to the active form of plasma kallikrein.

Bradykinin B2 Receptor Antagonists

In some embodiments, a bradykinin B2 receptor antagonist is administered to a subject. Exemplary bradykinin B2 receptor antagonists include Incatibant (Firazyr®), which is a peptidomimetic drug containing 10 amino acids which block binding of native bradykinin to the bradykinin B2 receptor.

C1-INH Replacement Agents

In some embodiment, a replacement C1-INH agent is administered to a subject. Exemplary C1-INH replacement agents are publicly available and include, for example, Berinert®, which is a purified human pasteurized nanofiltered C1-INH concentrate.

EXAMPLES

Example 1: Cleaved Kininogen

Based on analysis of the contact system, cleaved kininogen is a suitable biomarker for measuring contact system activation. Cleaved kininogen has been previously shown to be elevated during HAE attacks, in cirrhosis), and as a consequence of contact system activation during sepsis. Antibody phage display libraries were panned against cleaved kininogen in combination with depletion on intact kininogen. In parallel mice were immunized with cleaved kininogen and monoclonal antibodies obtained from hybridoma cell lines. Both efforts provided a number of different monoclonal antibodies that bound both cleaved and intact kininogen but no antibody that only bound cleaved kininogen.

Figure 2:
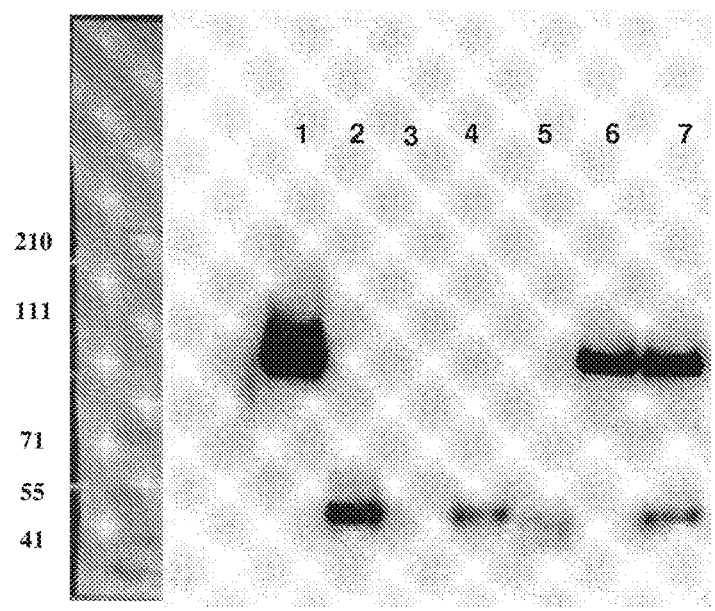
FIG. 2 shows cleaved kininogen detection by Western blot analysis. Samples were analyzed using SDS-PAGE (3-8% Tris-Acetate) under reducing conditions followed by transfer to PVDF membrane and immunoblotting. Lane1—50 nM Intact Kininogen; Lane 2—50 nM Cleaved Kininogen; Lane 3—50 nM Low Molecular Weight Kininogen; Lane 4—1:20 Sodium Citrated Human Plasma (Glass Collection Tube); Lane 5—1:20 Sodium Citrated Human Plasma (Plastic) Kallikrein Treated; Lane 6—1:20 Sodium Citrated Human Plasma (Plastic); Lane 7—1:20 Sodium Citrated Human Plasma (Plastic) 20 nM 2 Chain Kininogen Added.

A number of the antibodies were screened for suitability in a Western blot assay and several identified that work well including the mouse mAb (clone 11H05) shown in FIG. 2. It is evident that this assay is capable of detecting cleaved kininogen in human plasma samples. Furthermore, the data in FIG. 2 confirms that plasma collection in glass is sufficient to prevent contact activation and kininogen cleavage.

Mass spectrometry based approach can also be used detect cleaved kininogen in patient plasma. In this approach, one immune adsorbs kininogen from the patient sample, proteolytically digests the eluted kininogen and analyzes peptide fragments by LC-MC.

Example 2: Intact and Cleaved Kininogen

Figure 3:
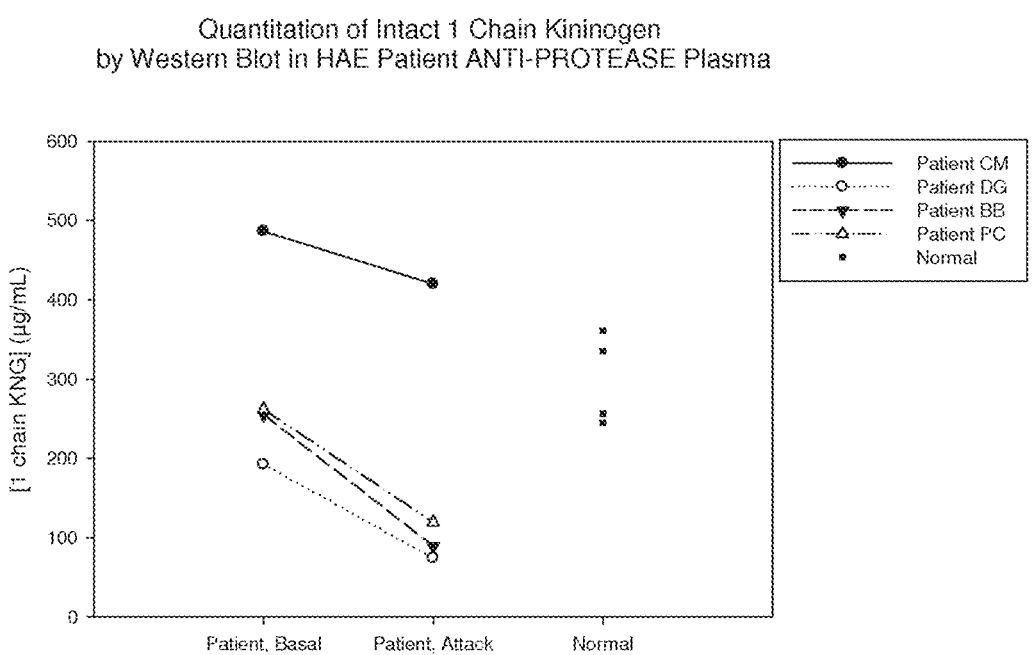
FIG. 3 shows detection of intact kininogen (i.e., 1-chain) in a patient sample obtained during an attack. Patient plasma sample was collected in citrated plasma tubes containing an anti-protease cocktail.

Western blot was used to show that plasma from a patient obtained during an attack and collected in citrated plasma tubes containing an anti-protease cocktail exhibits a decrease in amount of intact kininogen (i.e., 1-chain) (FIG. 3). An increase in cleaved kininogen (i.e., 2-chain) was observed.

Example 3: Assay for Measuring Levels of Cleaved Kininogen

A Western blot assay for the detection of intact (1-chain) and cleaved (2-chain) high molecular weight kininogen (HMWK) was further optimized using Licor detection. This assay described herein uses a mouse monoclonal antibody (clone 11H05) that was generated by hybridoma technology by immunizing animals with 2-chain HMWK and screening hybidoma fusions against both 1-chain and 2-chain HMWK by ELISA. The 11H05 mAb was selected based on its performance in a Western blot assay and its ability to specifically bind the light chain and not bind the heavy chain of HMWK. Light chain binders were preferred because the light chain is not present in the other plasma kininogen (low molecular weight kininogen, LMWK), which is not a pKal substrate. The assay was also used to demonstrate the importance of collecting plasma in plastic tubes as collection in glass tubes resulted in contact system activation (FIG. 4B).

In some examples, the following materials and conditions were used in the Western blot assay described herein:
Materials
  XCell SureLock® Mini-Cell, Life Technologies (Invitrogen), Cat. #EI0001
  Gel Box Power Supply
  iBlot® Western Blotting Transfer Device, Life Technologies (Invitrogen), Cat. #IB1001
  iBlot® Transfer Stack, nitrocellulose, mini, Life Technologies (Invitrogen), Cat. #IB301001
  Matrix Laboratories Impact 2 Multichannel Pipettor, or equivalent
  Rainin Pipetman, assorted volume ranges, Rainin, Cat #: P-10, P-20, P-100, P-200, and P-1000, or equivalent
  −80° C. Freezer with Chart Recorder
  −20° C. Freezer with Chart Recorder
  2-8° C. Refrigerator with Chart Recorder
  0.22 μm Polyethersulfone (PES) Filter Systems, Corning, Cat #431096 or equivalent
  Deionized and purified water (DI water), Ricca Chemical, Cat #9150-5, or equivalent
  NuPAGE 7% Tris-Acetate Gels, 15-well, Life Technologies (Invitrogen), Cat. #EA03555Box
  Tris-Acetate SDS Running Buffer (20×), Life Technologies (Invitrogen), Cat. #LA0041
  NuPAGE Sample Reducing Agent (10×), Life Technologies (Invitrogen), Cat. #NP0009
  NuPAGE Sample Buffer (4×), Life Technologies (Invitrogen), Cat. #NP0007
  NuPAGE 4-12% Bis-Tris Gels, 15-well, Life Technologies (Invitrogen), Cat. #NP0336BOX
  MES SDS Running Buffer (20×), Life Technologies (Invitrogen), Cat. #NP0002
  Odyssey Blocking Buffer, LI-COR, Cat. #927-40000
  Tween20, Sigma, Cat. #P1379
  Phosphate buffered saline pH 7.4, Sigma, Cat #P-3813 or equivalent
  Tris, Fisher Scientific, Cat. #T393-5000
  Sodium Chloride, JT Baker, Cat. #3624-19
  6N Hydrochloric Acid, EMD, Cat. #HX0603M-6
  3M Sodium Acetate Buffer pH 5.2, Teknova, Cat. #S0296
  Bovine Serum Albumin (BSA), IgG and Protease Free, Jackson ImmunoResearch, Cat. #001-000-162
  Mouse monoclonal anti-LC HMWK antibody clone, Clone 11H05 (#16), 1.4 mg/mL, Dyax
  Goat anti-Mouse IRDye 680RD, LI-COR, Cat. #926-68070
  Odyssey One-Color Molecular Weight Markers, LI-COR, Cat. #928-40000
  Anti-Protease Inhibitor Cocktail (10×), Provided by Dyax
  Factor XIIa, 1.47 mg/mL (21.6 μM), Enzyme Research Labs, Provided by Dyax
  Kinninogen Deficient Plasma, Hyphen-Biomed, Provided by Dyax
  Single-Chain HMWK, 1.61 mg/mL, Enzyme Research Labs, Cat. #HK 2700
  Two-Chain HMWK, 2.01 mg/mL, Enzyme Research Labs, Cat. #HK 2362
  Normal Human Plasma Samples, HAE Patient Samples, and Bioreclamation Samples
  Provided by Dyax
  DX2930, Dyax, Lot #PURDX1-L01, 32.1 mg/mL
  DX88, Dyax, Lot #B2007-029, 10.1 mg/mL
Protocol Outline:

| | |
|---|---|
| Non-Reduced Test Sample Preparation | Non-reduced test samples are prepared by adding 5 μL of 4X sample buffer to 15 μL of ~5% test samples. The samples are heated to 95° C. for 5 minutes. The samples are briefly centrifuged to remove any condensation from the test sample microcentrifuge tube lid. |
| Gel Loading and Running | Reduced samples are run using 4-12% Bis-Tris gels and non-reduced samples are run using 7% Tris-Acetate gels. A one-color protein marker is loaded into lane 1 of each gel. A QC sample is loaded into lane 2 of each gel. Reduced and non-reduced test samples are loaded into lanes 3-15 of the appropriate gel type. The gels are run at 125 V for ~75 minutes. |

| | -continued |
|---|---|
| Gel Transfer | Each gel is transferred to a nitrocellulose membrane using the iBlot transfer stacks, mini and the iBlot. After adding the gel and transfer stack to the iBlot, program P0 is selected and runs for ~7 minutes. After the transfer is complete, the membrane is transferred to a plastic tray containing 20 mL of Odyssey blocking buffer. |
| Membrane Blocking | Membranes are blocked with 20 mL of Odyssey blocking buffer. Membranes are incubated with blocking buffer on a plate shaker for 1 hour. |
| Mouse anti-HMWK LC mAb Preparation and Addition | Mouse anti-HMWK LC mAb is diluted to 1 µg/mL in Odyssey blocking buffer containing 0.2% Tween-20. The blocking buffer is discarded from each membrane. A volume of 20 mL of the 1 µg/mL primary antibody solution is added to each membrane and the membranes are incubated on a plate shaker for 1 hour at room temperature. |
| Goat anti-Mouse IRDye680 Preparation and Addition | Goat anti-mouse IRDye680 is prepared at a 1:15,000 dilution. The goat anti-mouse IRDye680 is initially prepared at a 1:10 dilution followed by a 1:1,500 for a final dilution of 1:15,000. The goat anti-mouse IRDye680 is prepared in Odyssey blocking buffer containing 0.2% Tween-20. The secondary antibody solution is added to each membrane and the membranes are incubated on a plate shaker for 1 hour at room temperature. |
| Membrane Reading | After a rinse with PBS, the membranes are placed on the Li-Cor Odyssey and the membranes are read. |
| Membrane Washing | The membranes are washed with PBS containing 0.1% Tween-20 for 5 minutes per wash for a total of four washes after the primary antibody incubation and the secondary antibody incubation. |

To assess the ability of mAb 11H05 to detect 1-chain and 2-chain HMWK, the purified proteins were spiked into HMWK-deficient plasma at concentrations that include levels observed in normal plasma (FIGS. 5A and 5B). It was evident that under reducing conditions, 11H05 detects 1-chain with higher sensitivity than 2-chain HMWK. By accounting for the differential sensitivity of the mAb for the two forms of HMWK, this assay could be used to accurately quantify the concentration of 1-chain and 2-chain HMWK in patient plasma. Alternatively, the percent 2-chain signal can be determined in plasma samples suspected of involving contact activation and compared to that of plasma from normal healthy individuals. Using this latter approach, the assay could be used to screen samples from different diseases and identify diseases associated with contact system activation.

Inter and intra-assay precision and accuracy tests were also performed. Under both non-reducing and reducing conditions, the assay performed acceptably producing percent CV values of <25% across all parameters tested.

Freeze-thaw stability tests were also performed on normal human plasma. It was determined that HMWK did not appear to degrade between 0 and 3 freeze-thaw cycles.

The Western blot assay was validated using plasma samples from patients with hereditary angioedema (HAE), a disease known to be caused by excess contact system activation and pKal activity. As shown in FIG. 6B, the percentage of cleaved HMWK in HAE plasma is approximately 20%, which is significantly higher than that of normal plasma. During an HAE attack, the percent cleaved HMWK detected using this assay is further elevated. This data clearly demonstrates increased cleaved HMWK in HAE plasma during quiescent (basal) disease status. The assay could therefore be used to monitor the effectiveness of therapeutic pKal inhibitors via an assessment of the degree to which they restore normal levels of cleaved kininogen.

Figure 7A:
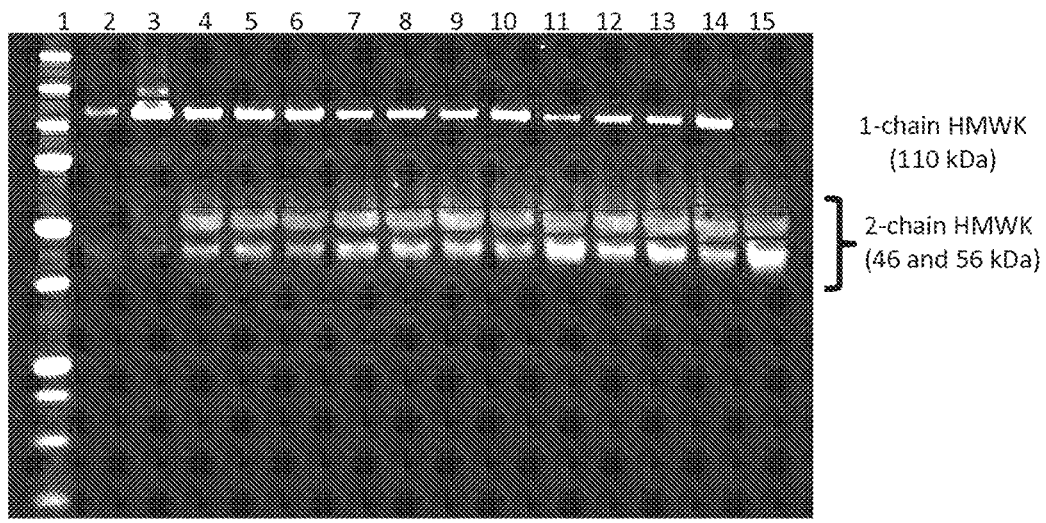
FIG. 7A shows a Western blot depicting evaluation of FXIIa activation conditions. Licor detection was used to detect normal human plasma activated with different concentrations of FXIIa at different temperatures (ice vs 37° C.) and incubation times (10 vs 30 minutes). Lane 1: molecular weight markers; Lane 2: purified 1-chain and 2-chain HMWK; Lane 3: normal human plasma; Lane 4: normal human plasma+2.5 nM FXIIa for 10 minutes at 37 C; Lane 5: normal human plasma+2.5 nM FXIIa for 30 minutes at 37 C; Lane 6: normal human plasma+2.5 nM FXIIa for 10 minutes on ice; Lane 7: normal human plasma+2.5 nM FXIIa for 30 minutes on ice; Lane 8: normal human plasma+5 nM FXIIa for 10 minutes at 37 C; Lane 9: normal human plasma+5 nM FXIIa for 30 minutes at 37 C; Lane 10: normal human plasma+5 nM FXIIa for 10 minutes on ice; Lane 11: normal human plasma+5 nM FXIIa for 30 minutes on ice; Lane 12: normal human plasma+7.5 nM FXIIa for 10 minutes at 37 C; Lane 13: normal human plasma+7.5 nM FXIIa for 30 minutes at 37 C; Lane 14: normal human plasma+7.5 nM FXIIa for 10 minutes on ice; Lane 15: normal human plasma+7.5 nM FXIIa for 30 minutes on ice.
Figure 7B:
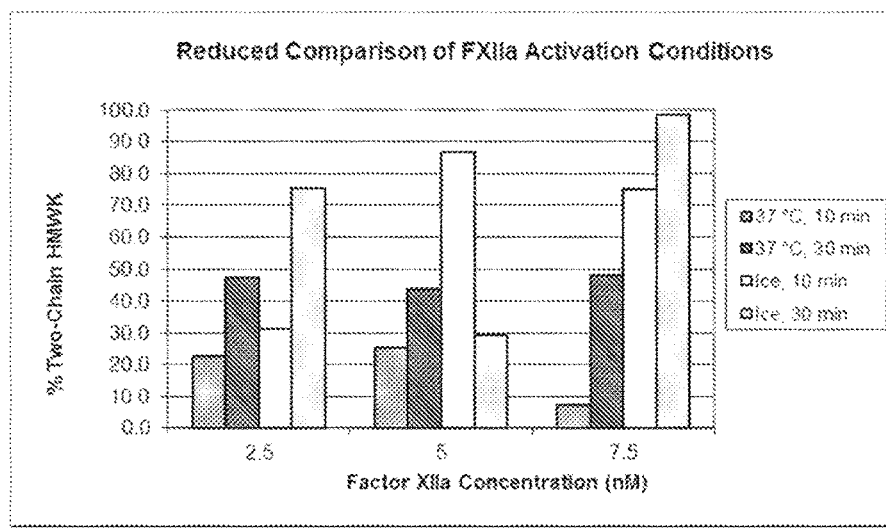
FIG. 7B shows a graph depicting evaluation of FXIIa activation conditions. Percent of two-chain HMWK in each lane determined using Licor signal intensities [%2-chain HMWK=(46 kDa signal+56 kDa signal)/(46 kDa signal+56 kDa signal+110 kDa signal)].

It is known that negatively charged surfaces or particles such as phospholipids or polyphosphates are effective activators of the contact system, which leads to formation of active pKal and the generation of the bradykinin from the proteolysis of 1-chain HMWK. The identity of the physiologic surface that leads to contact system activation in HAE attacks is not known. However, HAE attacks are associated with the generation of FXIIa. The use of FXIIa as a contact system initiator, rather than charged substances such as dextran sulfate or kaolin, enables more reproducible contact system activation and optimized assay performance. The concentration of FXIIa and reaction conditions were determined to approximate the percent cleaved kininogen that is observed in HAE patients (~20-50%) (FIG. 7B, Table 1).

TABLE 1

Licor Signal Intensities of FXIIa Treated Human Plasma Samples*
Reduced Comparison of Factor XIIa Activation Conditions

| FXIIa Conc. (nM) | Incubation Temp. | Incubation Time (min) | Single-Chain | Two-Chain (56 kDa) | Two-Chain (46 kDa) | Total Signal | % Two-Chain in Lane | % Two-Chain from Untreated Signal |
|---|---|---|---|---|---|---|---|---|
| 0 | N/A | N/A | 29500 | 202 | 300 | 30002 | 1.7% | N/A |
| 2.5 | 37° C. | 10 | 21900 | 4010 | 2370 | 28280 | 22.6% | 25.8% |
| 2.5 | 37° C. | 30 | 19500 | 4240 | 2370 | 26110 | 25.3% | 33.9% |
| 2.5 | Ice | 10 | 20900 | 447 | 1220 | 22567 | 7.4% | 29.2% |
| 2.5 | Ice | 30 | 8160 | 3380 | 3950 | 15490 | 47.3% | 72.3% |
| 5 | 37° C. | 10 | 9020 | 4070 | 2950 | 16040 | 43.8% | 69.4% |
| 5 | 37° C. | 30 | 8480 | 4070 | 3770 | 16320 | 48.0% | 71.3% |
| 5 | Ice | 10 | 13300 | 3270 | 2780 | 19350 | 31.3% | 54.9% |
| 5 | Ice | 30 | 2220 | 5220 | 9420 | 16860 | 86.8% | 92.5% |

TABLE 1-continued

Licor Signal Intensities of FXIIa Treated Human Plasma Samples*
Reduced Comparison of Factor XIIa Activation Conditions

| FXIIa Conc. (nM) | Incubation Temp. | Incubation Time (min) | Single-Chain | Two-Chain (56 kDa) | Two-Chain (46 kDa) | Total Signal | % Two-Chain in Lane | % Two-Chain from Untreated Signal |
|---|---|---|---|---|---|---|---|---|
| 7.5 | 37° C. | 10 | 4200 | 5610 | 6920 | 16730 | 74.9% | 85.8% |
| 7.5 | 37° C. | 30 | 4530 | 6310 | 7560 | 18400 | 75.4% | 84.6% |
| 7.5 | Ice | 10 | 12100 | 2510 | 2520 | 17130 | 29.4% | 59.0% |
| 7.5 | Ice | 30 | 260 | 4340 | 12300 | 16900 | 98.5% | 99.1% |

% Two-Chain in Lane: Sum of Two-Chain Signal/Sum of Total Lane Signal
% Two-Chain from Untreated Signal: 1 − (Treated Single-Chain Signal/Untreated Single-Chain Signal)
*Signal analysis of samples from Western Blot in FIG. 5A.

Figure 8A:
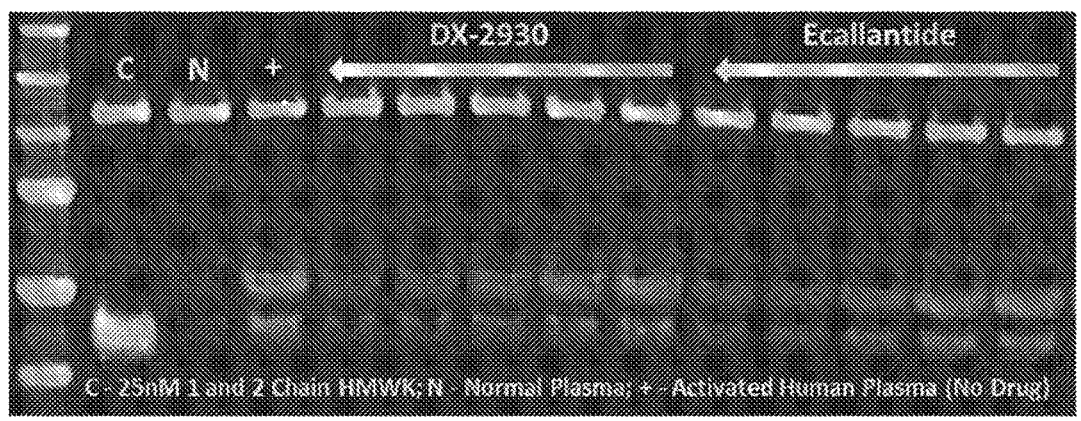
FIG. 8A shows a Western blot depicting the inhibitory effects of DX-88 and DX-2930 on FXIIa activation of pKal activity. Ecallantide and DX-2930 inhibit cleavage of HMWK by pKAL when added to human plasma ex vivo.
Figure 8B:
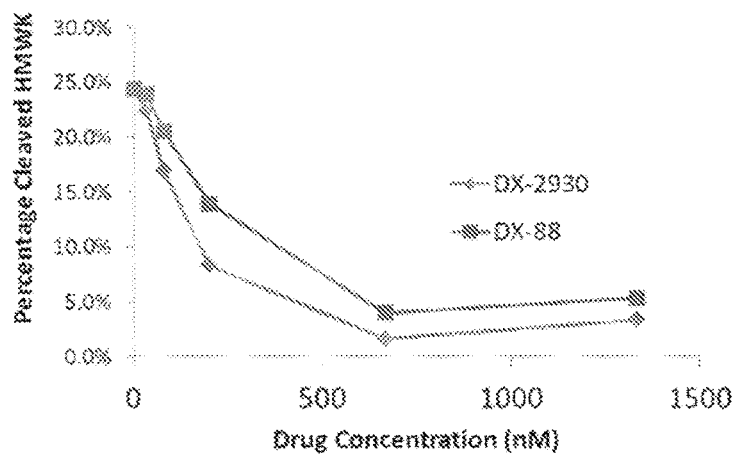
FIG. 8B shows a chart showing the effects of DX-88 and DX-2930 on the production of cleaved HMWK in the presence of FXIIa. Pooled sodium citrated human plasma was pretreated with either DX-2930 or ecallantide at concentrations ranging from 1370 to 34.3 nM. All samples (including an untreated sample) were activated by the addition of 2.5 nM FXIIa. The enzymes were then inhibited by the addition of a protease inhibitor cocktail. Equal molar concentrations of ecallantide and DX-2930 reduce the amount of cleaved HMWK equivalently in pooled human plasma when compared to the untreated plasma sample. C=25 nM 1 and 2 Chain HMWK; N=Normal plasma; +=Activated human plasma (no drug).

Using a FXIIa concentration of 2.5 nM and optimized reaction conditions, normal human plasma from 15 males and 15 females were examined in the presence or absence of 10 μg/mL DX-2930 (a potent antibody inhibitor of pKal activity) and the percent 2-chain HMWK determined (Table 2). It is evident that the assay is capable of detecting plasma kallikrein inhibition of HMWK proteolysis in plasma. DX-2930 was shown to exhibit an approximately equivalent potency in this assay to ecallantide, an approved pKal inhibitor for the treatment of HAE attacks (FIGS. 8A and 8B). Equal potency to ecallantide in this in vitro assay suggests that equivalent drug levels may be equally effective in HAE.

TABLE 2

Average Percent of Two-Chain in Lane, Reduced and Non-Reduced Values*
Average Percent of Two-Chain in Lane

| Sample | XIIa (nM) | DX2930 (μg/mL) | Reduced | Non-Reduced |
|---|---|---|---|---|
| Male Average | 0 | 0 | 16.1% | 32.0% |
|  | 2.5 | 0 | 42.0% | 61.2% |
|  | 2.5 | 10 | 29.5% | 43.6% |
| Female Average | 0 | 0 | 9.6% | 21.5% |
|  | 2.5 | 0 | 43.8% | 50.2% |
|  | 2.5 | 10 | 26.4% | 30.3% |

*Average of plasma from 15 males and 15 females.

Figure 9:
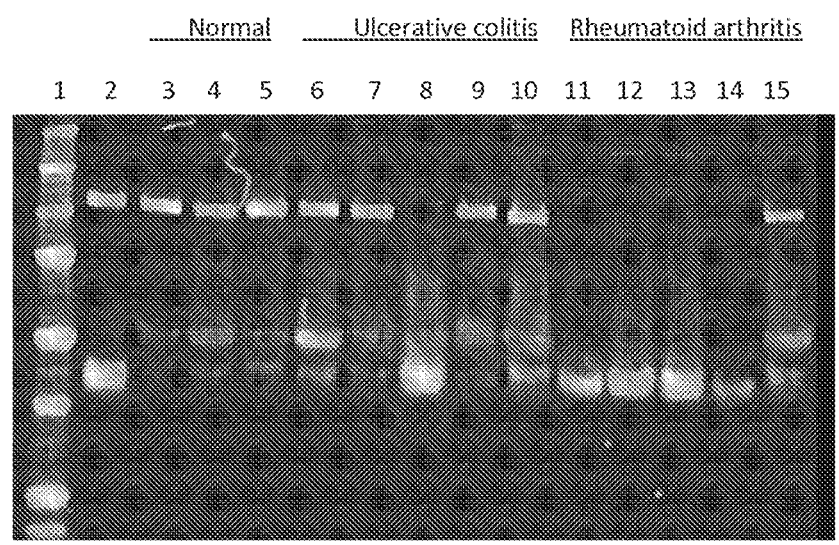
FIG. 9 shows a Western blot analysis of contact system activation in patients with ulcerative colitis (UC) and rheumatoid arthritis (RA). Lane 1: molecular weight markers; Lane 2: purified 1-chain and 2-chain HMWK; Lanes 3 to 5: normal human plasma; Lanes 6 to 10: plasma from UC patients; Lanes 11 to 15: plasma from RA patients. Further details regarding the samples in each lane are provided in Table 3.

Samples from patients with ulcerative colitis (UC) and rheumatoid arthritis (RA) were also tested using this western blot assay. Patient plasma samples were obtained from Bioreclamation and collected in anticoagulant in plastic tubes. The percent of cleaved kininogen was found to be elevated in both UC and RA patients compared to normal control patients (FIG. 9, Table 3).

TABLE 3

Summary of Western Blot Analysis of Ulcerative Colitis and Rheumatoid Arthritis Samples Reduced Diseased State Samples in K2EDTA and Sodium Citrate, Ulcerative Collitis and Rheumatoid Arthritis

| | | | | HMWK Signal | | | | |
|---|---|---|---|---|---|---|---|---|
| Lane | Sample | anti-Coagulant | Disease | Single-Chain (110 kDa) | Two-Chain (56 kDa) | Two-Chain (46 kDa) | Total Signal | % Two-Chain in Lane |
| 1 | Molecular Weight Stds | n/a | n/a | n/a | n/a | n/a | n/a | n/a |
| 2 | 1-chain and 2-chain Stds | n/a | n/a | n/a | n/a | n/a | n/a | n/a |
| 3 | A3005, N17 | anti-protease | Normal | 20500 | 775 | 366 | 21641 | 5.3% |
| 4 | BRH745075 | Sodium Citrate | Normal | 18700 | 1340 | 802 | 20842 | 10.3% |
| 5 | BRH745056 | Sodium Citrate | Normal | 24200 | 893 | 782 | 25875 | 6.5% |
| 6 | BRH715036 | K2EDTA | Ulcerative Collitis | 17400 | 3030 | 1340 | 21770 | 20.1% |
| 7 | BRH715037 | Sodium Citrate | Ulcerative Collitis | 17400 | 1220 | 694 | 19314 | 9.9% |
| 8 | BRH715038 | Sodium Citrate | Ulcerative Collitis | N/A | 2140 | 10300 | 12440 | 100.0% |
| 9 | BRH715039 | Sodium Citrate | Ulcerative Collitis | 14100 | 1700 | 596 | 16396 | 14.0% |
| 10 | BRH715040 | Sodium Citrate | Ulcerative Collitis | 13300 | 1170 | 2070 | 16540 | 19.6% |
| 11 | BRH715041 | K2EDTA | Rheumatoid Arthritis | N/A | N/A | 4950 | 4950 | 100.0% |
| 12 | BRH715042 | K2EDTA | Rheumatoid Arthritis | 88 | N/A | 9250 | 9338 | 99.1% |
| 13 | BRH715043 | K2EDTA | Rheumatoid Arthritis | N/A | N/A | 6900 | 6900 | 100.0% |
| 14 | BRH715044 | Sodium Citrate | Rheumatoid Arthritis | N/A | N/A | 2850 | 2850 | 100.0% |
| 15 | BRH715045 | Sodium Citrate | Rheumatoid Arthritis | 6600 | 1860 | 1520 | 9980 | 33.9% |

Figure 10:
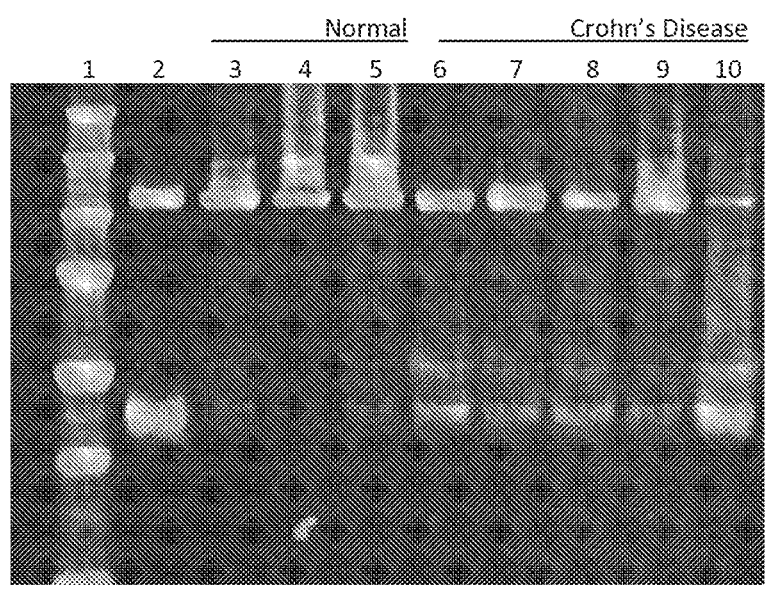
FIG. 10 shows a Western blot analysis of contact system activation in patients with Crohn's Disease (CD). Lane 1: molecular weight markers; Lane 2: purified 1-chain and 2-chain HMWK; Lanes 3 to 5: normal human plasma; Lanes 6 to 10: plasma from CD patients. Further details regarding the samples in each lane are provided in Table 4.

Samples from patients with Crohn's disease (CD) were also tested using the western blot assay. Patient plasma samples were obtained from Bioreclamation and collected in anticoagulant in plastic tubes. The percent of cleaved kininogen was found to be elevated in CD patients compared to normal control patients (FIG. 10, Table 4).

TABLE 4

Summary of Western Blot Analysis of Crohn's Disease Samples

| | | | | HMWK Signal | | | | |
|---|---|---|---|---|---|---|---|---|
| Lane | Sample | anti-Coagulant | Disease | Single-Chain (150 kDa) | Single-Chain (110 kDa) | Two-Chain (56 kDa) | Two-Chain (46 kDa) | Total Signal | % Two-Chain in Lane |
| 1 | Molecular Weight Stds | n/a | n/a | n/a | n/a | n/a | n/a | n/a | n/a |
| 2 | 1-chain and 2-chain Stds | n/a | n/a | n/a | n/a | n/a | n/a | n/a | n/a |
| 3 | A2992, N14 | Sodium Citrate | Normal | 704 | 12900 | 384 | 576 | 14564 | 6.6% |
| 4 | BRH745047 | Sodium Citrate | Normal | 1560 | 5820 | | 192 | 7572 | 2.5% |
| 5 | BRH745076 | Sodium Citrate | Normal | 5720 | 12300 | 382 | 480 | 18882 | 4.6% |
| 6 | BRH715026 | K2EDTA | Crohn's Disease | N/A | 12100 | 1230 | 1950 | 15280 | 20.8% |
| 7 | BRH715027 | K2EDTA | Crohn's Disease | N/A | 16300 | 668 | 1550 | 18518 | 12.0% |
| 8 | BRH715028 | K2EDTA | Crohn's Disease | N/A | 6650 | 504 | 2250 | 9404 | 29.3% |
| 9 | BRH715029 | K2EDTA | Crohn's Disease | 1900 | 14100 | N/A | 680 | 16680 | 4.1% |
| 10 | BRH715030 | K2EDTA | Crohn's Disease | N/A | 1320 | 3230 | 6020 | 10570 | 87.5% |

Example 4: Effects of FXIIa and DX2930 on Normal Human Plasma (NHP) Samples

Purpose:

The purpose of this experiment was to determine the effects of DX-2930 on FXIIa contact system activation. DX2930 can inhibit plasma kallikrein, reducing the measured two-chain to one-chain ratio in response to treatment with FXIIa. Sodium citrated NHP samples from five males and five females were tested untreated, after FXIIa activation, and after FXIIa activation when samples were pretreated with 10 µg/mL of DX-2930. Each sample set was assayed under non-reduced and reduced conditions.

Procedure:

Sample Preparation

1. NHP samples were removed from frozen storage and allowed to equilibrate to room temperature. The following male NHP samples were tested: BRH745050, BRH745051, BRH745052, BRH745053, and BRH745054. The following female samples were tested: BRH745065, BRH745066, BRH745067, BRH745068, and BRH745069.
2. DX2930 was prepared at 215 µg/mL by adding 3.35 µL of the DX2930 stock (Lot #PURDX1-L01, 32.1 mg/mL) to 496.65 µL of 1×TBS.
3. A 1:10 intermediate of the FXIIa solution was prepared by adding 5 µL of the FXIIa stock solution (25,300 nM) to 45 µL of TBS. A 56.25 nM FXIIa solution was prepared by adding 4.45 µL of the 1:10 intermediate to 195.55 µL of TBS.
4. Each NHP sample was prepared with 10 µg/mL of DX2930 by adding 2 µL of the 215 µg/mL DX2930 solution to 41 µL of NHP.
5. Each NHP sample was prepared with 2.5 nM of FXIIa by adding 2 µL of the 56.25 nM FXIIa solution to 43 µL of each NHP sample, with and without DX2930.
6. The samples were incubated with FXIIa at 37° C. for 10 minutes. The reaction was stopped by adding 5 µL of 10× anti-protease inhibitors.
7. Each NHP sample, with FXIIa, with DX2930 and FXIIa, and untreated sample was diluted to 5% plasma by adding 5 µL of the sample to 95 µL TBS.
8. The non-reduced samples were prepared by adding 5 µL of 4× sample buffer to 15 µL of sample.
9. The reduced samples were prepared by adding 5 µL of the 4× sample buffer and 2 µL of 10× reducing agent to 13 µL of sample.
10. All of the samples at were heated at 95° C. for 5 minutes using a heat block.

Gel Loading, Running, and Transfer

1. A volume of 1 L of 1× Tris-Acetate SDS running buffer was prepared by adding 50 mL of 20× Tris-Acetate SDS running buffer to 950 mL of DI water.
2. A volume of 1 L of 1×MES running buffer was prepared by adding 50 mL of 20×MES SDS running buffer to 950 mL of DI water.
3. Assay buffer (Odyssey Blocking buffer with 0.2% Tween) was prepared by adding 1 mL of Tween-20 to 499 mL of Odyssey blocking buffer.
4. Wash buffer (PBS with 0.1% Tween) was prepared by adding 1 packet of PBS and 1 mL of Tween-20 to 900 mL of DI water. The solution was mixed well and QS'd to 1 L using DI water. The final solution was filtered through a 0.22 µM PES filtration system.
5. A volume of 4 µL of one-color protein marker was added to lane 1 of two gels.
6. Volumes of 13 µl of the non-reduced samples were added to the appropriate lanes of a 7% Tris-Acetate gel.
7. Volumes of 13 µL of the reduced samples were added to the appropriate lanes of a 4-12% Bis-Tris gel.
8. The gels were run at 125 volts for ~75 minutes.
9. Each gel was individually transferred to a membrane using the iBlot mini-transfer stacks and Program P0 of the iBlot transfer system.
10. Each membrane was transferred to a plastic tray containing 20 mL of Odyssey blocking buffer. The membranes were incubated in Odyssey blocking buffer on a plate shaker at room temperature for 1 hour.
11. A 1 µg/mL primary antibody solution was prepared by adding 28.58 µL of the mouse anti-HMWK mAb, clone #11H05, 1.4 mg/mL to 29,971.42 µL of assay buffer.
12. The blocking buffer was removed from the plastic trays. A volume of 20 mL of the primary antibody solution was added to each tray and the membranes were incubated on a plate shaker at room temperature for 1 hour.
13. A 1:10 intermediate of goat anti-mouse IgG IRDye680 was prepared by adding 5 μL of the goat anti-mouse IgG IRDye680 to 45 μL of assay buffer. The secondary antibody solution was prepared at a 1:15,000 dilution by adding 26.66 μL of the 1:10 goat anti-mouse IgG IRDye680 intermediate to 39,973.34 μL of assay buffer.
14. The primary antibody solution was removed from the trays.
15. Each membrane was washed for five minutes with 20 mL of wash buffer and then the wash solution discarded. The wash was repeated for a total of 4 washes.
16. A volume of 20 mL of the secondary antibody solution was added to each tray and the membranes were incubated on a plate shaker at room temperature for 1 hour.
17. The secondary antibody solution was removed from the trays.
18. Each membrane was washed for five minutes with 20 mL of wash buffer and then the wash solution discarded. The wash was repeated for a total of 4 washes.
19. Each membrane was rinsed with PBS for 5 minutes.
20. The membranes were scanned using the LiCor Odyssey CLx.

Results:

Tables 5 and 6 contain the non-reduced sample data. Tables 7 and 8 contain the reduced sample data. The percent of cleaved HMWK was calculated using two methods. The percent of two-chain in lane was determined using the following equation: Sum of Two-Chain Signal/Sum of the Total Signal. The percent of two-chain from the untreated signal was determined using the following formula: 1—(Treated Single-Chain Signal/Untreated Single-Chain Signal). The treated and untreated samples were prepared slightly differently with the untreated samples having a slightly higher percentage of plasma in the sample preparation. Therefore the untreated samples produced slightly higher overall signals than the treated samples. The percent of two-chain in lane value was used to determine the percent cleaved HWMK because of the slightly different sample preparation between treated and untreated samples.

Table 16 contains a summary of the activation and inhibition results. Under reduced conditions, untreated male and female NHP samples contained an average of 16.1% and 9.6% cleaved HMWK respectively. Male and female NHP samples treated with FXIIa contained an average of 42.0% and 43.8% of cleaved HMWK respectively. Male and female NHP samples pre-treated with DX-2930 followed by treatment with FXIIa contained an average of 29.5% and 26.4% cleaved HMWK respectively.

Under non-reduced conditions, untreated male and female NHP samples contained an average of 32.0% and 21.5% cleaved HMWK respectively. Male and female NHP samples treated with FXIIa contained an average of 61.2% and 50.2% of cleaved HMWK respectively. Male and female NHP samples pre-treated with DX-2930 followed by treatment with FXIIa contained an average of 43.6% and 30.3% cleaved HMWK respectively.

Conclusion:

Treatment of NHP samples with FXIIa increased the percent cleaved HMWK compared to untreated samples. NHP samples pre-treated with DX-2930, followed by FXIIa activation, produced less cleaved HMWK than samples treated with only FXIIa but slightly higher percent cleaved HMWK compared to untreated samples. The reduced untreated NHP samples contained less cleaved HMWK than the non-reduced untreated NHP samples. It was also found that NHP samples untreated, treated with FXIIa, and pre-treated with DX2930 followed by treatment with FXIIa produced reproducible results.

TABLE 5

Non-Reduced DX2930 Inhibition of FXIIa Activation, Male Samples, Single/Two-Chain HMWK Signals, Total Signal, Percent of Two-Chain HMWK
Non-Reduced Activation of Male NHP with Factor XIIa, Inhibition of Factor XIIa with DX2930

| Male NHP Sample | FXIIa (nM) | DX2930 (μg/mL) | HMWK Signal | | | Total Signal | % Two-Chain in Lane | % Two-Chain from Untreated Signal |
| --- | --- | --- | --- | --- | --- | --- | --- | --- |
| | | | Single-Chain (120 kDa) | Two-Chain (100 kDa) | Two-Chain (90 kDa) | | | |
| BRH745050 | 0 | 0 | 17900 | 4670 | 0 | 22570 | 20.7% | N/A |
| BRH745050 | 2.5 | 0 | 8160 | 7750 | 1770 | 17680 | 53.8% | 54.4% |
| BRH745050 | 2.5 | 10 | 12600 | 6620 | 812 | 20032 | 37.1% | 29.6% |
| BRH745051 | 0 | 0 | 19600 | 3450 | 0 | 23050 | 15.0% | N/A |
| BRH745051 | 2.5 | 0 | 10000 | 9430 | 2140 | 21570 | 53.6% | 49.0% |
| BRH745051 | 2.5 | 10 | 15300 | 6480 | 915 | 22695 | 32.6% | 21.9% |
| BRH745052 | 0 | 0 | 22500 | 8570 | 1100 | 32170 | 30.1% | N/A |
| BRH745052 | 2.5 | 0 | 11000 | 10700 | 3050 | 24750 | 55.6% | 51.1% |
| BRH745052 | 2.5 | 10 | 16500 | 8500 | 1500 | 26500 | 37.7% | 26.7% |
| BRH745053 | 0 | 0 | 6370 | 13100 | 7390 | 26860 | 76.3% | N/A |
| BRH745053 | 2.5 | 0 | 1710 | 8310 | 10500 | 20520 | 91.7% | 73.2% |
| BRH745053 | 2.5 | 10 | 4360 | 9310 | 6490 | 20160 | 78.4% | 31.6% |
| BRH745054 | 0 | 0 | 27100 | 5900 | 0 | 33000 | 17.9% | N/A |
| BRH745054 | 2.5 | 0 | 11500 | 9880 | 2270 | 23650 | 51.4% | 57.6% |
| BRH745054 | 2.5 | 10 | 15100 | 6280 | 814 | 22194 | 32.0% | 44.3% |

% Two-Chain in Lane: Sum of Two-Chain Signal/Sum of Total Lane Signal
% Two-Chain from Untreated Signal: 1 − (Treated Single-Chain Signal/Untreated Single-Chain Signal)

TABLE 6

Non-Reduced DX2930 Inhibition of FXIIa Activation, Female Samples,
Single/Two-Chain HMWK Signals, Total Signal, Percent of Two-Chain HMWK
Non-Reduced Activation of Female NHP with Factor XIIa, Inhibition of Factor XIIa with DX2930

| Female NHP Sample | FXIIa (nM) | DX2930 (µg/mL) | HMWK Signal | | | Total Signal | % Two-Chain in Lane | % Two-Chain from Untreated Signal |
|---|---|---|---|---|---|---|---|---|
| | | | Single-Chain (120 kDa) | Two-Chain (100 kDa) | Two-Chain (90 kDa) | | | |
| BRH745065 | 0 | 0 | 14700 | 2500 | 161 | 17361 | 15.3% | N/A |
| BRH745065 | 2.5 | 0 | 4750 | 5550 | 3160 | 13460 | 64.7% | 67.7% |
| BRH745065 | 2.5 | 10 | 10500 | 3270 | 453 | 14223 | 26.2% | 28.6% |
| BRH745066 | 0 | 0 | 23200 | 4460 | 17.4 | 27677 | 16.2% | N/A |
| BRH745066 | 2.5 | 0 | 14200 | 10600 | 1780 | 26580 | 46.6% | 38.8% |
| BRH745066 | 2.5 | 10 | 15100 | 5920 | 205 | 21225 | 28.9% | 34.9% |
| BRH745067 | 0 | 0 | 26000 | 8610 | 300 | 34910 | 25.5% | N/A |
| BRH745067 | 2.5 | 0 | 13700 | 9470 | 1410 | 24580 | 44.3% | 47.3% |
| BRH745067 | 2.5 | 10 | 19800 | 8880 | 795 | 29475 | 32.8% | 23.8% |
| BRH745068 | 0 | 0 | 25400 | 9180 | 211 | 34791 | 27.0% | N/A |
| BRH745068 | 2.5 | 0 | 14200 | 12500 | 2610 | 29310 | 51.6% | 44.1% |
| BRH745068 | 2.5 | 10 | 15800 | 7350 | 708 | 23858 | 33.8% | 37.8% |
| BRH745069 | 0 | 0 | 20900 | 6470 | 0 | 27370 | 23.6% | N/A |
| BRH745069 | 2.5 | 0 | 17000 | 11500 | 1820 | 30320 | 43.9% | 18.7% |
| BRH745069 | 2.5 | 10 | 21600 | 8960 | 198 | 30758 | 29.8% | −3.3% |

% Two-Chain in Lane: Sum of Two-Chain Signal/Sum of Total Lane Signal
% Two-Chain from Untreated Signal: 1 − (Treated Single-Chain Signal/Untreated Single-Chain Signal)

TABLE 7

Reduced DX2930 Inhibition of FXIIa Activation, Male Samples,
Single/Two-Chain HMWK Signals, Total Signal, Percent of Two-Chain HMWK
Reduced Activation of Male NHP with Factor XIIa, Inhibition of Factor XIIa with DX2930

| Male NHP Sample | FXIIa (nM) | DX2930 (µg/mL) | HMWK Signal | | | Total Signal | % Two-Chain in Lane | % Two-Chain from Untreated Signal |
|---|---|---|---|---|---|---|---|---|
| | | | Single-Chain | Two-Chain (56 kDa) | Two-Chain (46 kDa) | | | |
| BRH745050 | 0 | 0 | 28300 | 0 | 0 | 28300 | 0.0% | N/A |
| BRH745050 | 2.5 | 0 | 14400 | 3360 | 2620 | 20380 | 29.3% | 49.1% |
| BRH745050 | 2.5 | 10 | 19200 | 2560 | 1430 | 23190 | 17.2% | 32.2% |
| BRH745051 | 0 | 0 | 26800 | 0 | 0 | 26800 | 0.0% | N/A |
| BRH745051 | 2.5 | 0 | 12800 | 2950 | 2580 | 18330 | 30.2% | 52.2% |
| BRH745051 | 2.5 | 10 | 13900 | 2100 | 1210 | 17210 | 19.2% | 48.1% |
| BRH745052 | 0 | 0 | 17800 | 853 | 1500 | 20153 | 11.7% | N/A |
| BRH745052 | 2.5 | 0 | 12100 | 2980 | 3250 | 18330 | 34.0% | 32.0% |
| BRH745052 | 2.5 | 10 | 16900 | 2790 | 2190 | 21880 | 22.8% | 5.1% |
| BRH745053 | 0 | 0 | 7280 | 4340 | 8430 | 20050 | 63.7% | N/A |
| BRH745053 | 2.5 | 0 | 3180 | 5620 | 9240 | 18040 | 82.4% | 56.3% |
| BRH745053 | 2.5 | 10 | 6420 | 5470 | 6660 | 18550 | 65.4% | 11.8% |
| BRH745054 | 0 | 0 | 22100 | 625 | 586 | 23311 | 5.2% | N/A |
| BRH745054 | 2.5 | 0 | 9610 | 2660 | 2020 | 14290 | 32.8% | 56.5% |
| BRH745054 | 2.5 | 10 | 12500 | 2010 | 1300 | 15810 | 20.9% | 43.4% |

% Two-Chain in Lane: Sum of Two-Chain Signal/Sum of Total Lane Signal
% Two-Chain from Untreated Signal: 1 − (Treated Single-Chain Signal/Untreated Single-Chain Signal)

TABLE 8

Reduced DX2930 Inhibition of FXIIa Activation, Female Samples,
Single/Two-Chain HMWK Signals, Total Signal, Percent of Two-Chain HMWK
Reduced Activation of Female NHP with Factor XIIa, Inhibition of Factor XIIa with DX2930

| Female NHP Sample | FXIIa (nM) | DX2930 (µg/mL) | HMWK Signal | | | Total Signal | % Two-Chain in Lane | % Two-Chain from Untreated Signal |
|---|---|---|---|---|---|---|---|---|
| | | | Single-Chain | Two-Chain (56 kDa) | Two-Chain (46 kDa) | | | |
| BRH745065 | 0 | 0 | 17300 | 2080 | 1240 | 20620 | 16.1% | N/A |
| BRH745065 | 2.5 | 0 | 4100 | 4880 | 3450 | 12430 | 67.0% | 76.3% |
| BRH745065 | 2.5 | 10 | 9770 | 3740 | 1960 | 15470 | 36.8% | 43.5% |

TABLE 8-continued

Reduced DX2930 Inhibition of FXIIa Activation, Female Samples,
Single/Two-Chain HMWK Signals, Total Signal, Percent of Two-Chain HMWK
Reduced Activation of Female NHP with Factor XIIa, Inhibition of Factor XIIa with DX2930

| Female NHP Sample | FXIIa (nM) | DX2930 (µg/mL) | HMWK Signal | | | Total Signal | % Two-Chain in Lane | % Two-Chain from Untreated Signal |
|---|---|---|---|---|---|---|---|---|
| | | | Single-Chain | Two-Chain (56 kDa) | Two-Chain (46 kDa) | | | |
| BRH745066 | 0 | 0 | 21300 | 1770 | 753 | 23823 | 10.6% | N/A |
| BRH745066 | 2.5 | 0 | 9710 | 4280 | 2760 | 16750 | 42.0% | 54.4% |
| BRH745066 | 2.5 | 10 | 13600 | 3990 | 1780 | 19370 | 29.8% | 36.2% |
| BRH745067 | 0 | 0 | 21900 | 375 | 1850 | 24125 | 9.2% | N/A |
| BRH745067 | 2.5 | 0 | 11900 | 5120 | 3430 | 20450 | 41.8% | 45.7% |
| BRH745067 | 2.5 | 10 | 19000 | 3610 | 2440 | 25050 | 24.2% | 13.2% |
| BRH745068 | 0 | 0 | 29400 | 525 | 966 | 30891 | 4.8% | N/A |
| BRH745068 | 2.5 | 0 | 19600 | 5660 | 5130 | 30390 | 35.5% | 33.3% |
| BRH745068 | 2.5 | 10 | 25100 | 4050 | 3260 | 32410 | 22.6% | 14.6% |
| BRH745069 | 0 | 0 | 19900 | 500 | 688 | 21088 | 5.6% | N/A |
| BRH745069 | 2.5 | 0 | 12000 | 2910 | 2560 | 17470 | 31.3% | 39.7% |
| BRH745069 | 2.5 | 10 | 15000 | 1790 | 1350 | 18140 | 17.3% | 24.6% |

% Two-Chain in Lane: Sum of Two-Chain Signal/Sum of Total Lane Signal
% Two-Chain from Untreated Signal: 1 − (Treated Single-Chain Signal/Untreated Single-Chain Signal)

TABLE 9

Average Percent of Two-Chain in Lane,
Reduced and Non-Reduced Values
Average Percent of Two-Chain in Lane

| Sample | XIIa (nM) | DX2930 (µg/mL) | Reduced | Non-Reduced |
|---|---|---|---|---|
| Male Average | 0 | 0 | 16.1% | 32.0% |
| | 2.5 | 0 | 42.0% | 61.2% |
| | 2.5 | 10 | 29.5% | 43.6% |
| Female Average | 0 | 0 | 9.6% | 21.5% |
| | 2.5 | 0 | 43.8% | 50.2% |
| | 2.5 | 10 | 26.4% | 30.3% |

Example 6. Inhibition of FXIIa Activation Using DX-2930 and DX-88

Purpose:

The purpose of this experiment was to determine the effectiveness of DX-2930 and DX-88 on inhibiting the FXIIa activation. DX-2930 was tested at 5 concentrations: 200, 100, 30, 12, and 5 µg/mL. DX-88 was tested at 5 concentrations: 9.4, 4.7, 1.4, 0.56, and 0.24 µg/mL. Samples pre-treated with DX-2930 and DX-88 were treated with FXIIa. In addition to the pre-treated samples, one untreated sample, and two samples treated with only FXIIa were tested. The samples were tested under reduced conditions.

Procedure:

1. An NHP pool was prepared by adding 250 µL of each plasma sample, BRH745070, BRH745071, and BRH745048 to a 1.5 mL microcentrifuge tube and mixed well.
2. A 4500 µg/mL DX2930 solution was prepared by adding 4.21 µL of the DX2930 stock solution (32.1 mg/mL) to 25.79 µL of TBS. A 2250 µg/mL DX2930 solution was prepared by adding 15 µL of the 4500 µg/mL solution to 15 µL of TBS. A 675 µg/mL DX2930 solution was prepared by adding 6 µL of the 2250 µg/mL solution to 14 µL of TBS. A 270 µg/mL DX2930 solution was prepared by adding 8 µL of the 675 µg/mL solution to 12 µL of TBS. A 112.5 µg/mL DX2930 solution was prepared by adding 10 µl of the 270 µg/mL solution to 14 µL of TBS.
3. Five plasma samples pre-treated with DX-2930 were prepared by adding 2 µL of each DX2930 solution to 41 µL of the NHP pool.
4. A 211.5 µg/mL DX88 solution was prepared by adding 6.28 µL of the DX88 stock solution (10.1 mg/mL) to 293.72 µL of TBS. A 105.75 µg/mL DX88 solution was prepared by adding 15 µL of the 211.5 µg/mL solution to 15 µL of TBS. A 31.5 µg/mL DX88 solution was prepared by adding 8.94 µL of the 105.75 µg/mL solution to 21.06 µL of TBS. A 12.6 µg/mL DX88 solution was prepared by adding 12 µL of the 31.5 µg/mL solution to 18 µL of TBS. A 5.4 µg/mL DX88 solution was prepared by adding 12.86 µL of the 12.6 µg/mL to 17.14 µL of TBS.
5. Five plasma samples pre-treated with DX-88 were prepared by adding 2 µL of each DX-88 solution to 41 µL of the NHP pool.
6. A 1:10 intermediate of FXIIa was prepared by adding 5 µL of the stock solution (25,300 nM) to 45 µL of TBS. A 56.25 nM FXIIa solution was prepared by adding 4.45 µL of the 1:10 intermediate to 195.55 µL of TBS.
7. Each plasma sample pre-treated with DX2930 and DX88 was treated with 2.5 nM of FXIIa by adding 2 µL of the 56.25 nM FXIIa solution to each sample.
8. Two samples containing only FXIIa were prepared by adding 2 µL of TBS and 2 µL of the 56.25 nM FXIIa solution to 41 µL of the NHP pool.
9. One untreated sample was prepared by adding 4 µL of TBS to 41 µL of the NHP pool.
10. Incubated all of the samples containing FXIIa at 37° C. for 10 minutes.
11. A volume of 5 µL of anti-protease inhibitors was added to each sample including the untreated sample. The total sample volume for each replicate was 50 µL.
12. Each sample was diluted to ~5% plasma by adding 5 µL of the sample to 95 µL TBS.
13. The samples were prepared by adding 5 µL of the 4× sample buffer and 2 µL of 10×reducing agent to 13 µL of sample.
14. All of the samples were heated at 95° C. for 5 minutes using a heat block.
15. A volume of 1 L of 1×MES running buffer was prepared by adding 50 mL of 20×MES SDS running buffer to 950 mL of DI water.
16. Assay buffer (Odyssey Blocking buffer with 0.2% Tween) was prepared by adding 1 mL of Tween-20 to 499 mL of Odyssey blocking buffer.

17. Wash buffer (PBS with 0.1% Tween) was prepared by adding 1 packet of PBS and 1 mL of Tween-20 to 900 mL of DI water. The solution was mixed well and QS'd to 1 L using DI water. The final solution was filtered through a 0.22 μM PES filtration system.
18. A volume of 4 μL of one-color protein marker was added to lane 1 of two gels.
19. Volumes of 13 μL of the reduced samples were added to the appropriate lanes of a 4-12% Bis-Tris gel.
20. The gel was run at 125 volts for ~75 minutes.
21. The gel was transferred to a membrane using the iBlot mini-transfer stack and Program P0 on the iBlot transfer system.
22. The membrane was transferred to a plastic tray containing 20 mL of Odyssey blocking buffer. The membrane was incubated in Odyssey blocking buffer on a plate shaker at room temperature for 1 hour.
23. A 1 μg/mL primary antibody solution was prepared by adding 14.29 μL of the mouse anti-HMWK mAb, clone #11H05, 1.4 mg/mL to 19,985.7 μL of assay buffer.
24. The blocking buffer was removed from the plastic tray. A volume of 20 mL of the primary antibody solution was added to the membrane and incubated on a plate shaker at room temperature for 1 hour.
25. A 1:10 intermediate of goat anti-mouse IgG IRDye680 was prepared by adding 5 μL of the goat anti-mouse IgG IRDye680 to 45 μL of assay buffer. The secondary antibody solution was prepared at a 1:15,000 dilution by adding 13.33 μL of the 1:10 goat anti-mouse IgG IRDye680 intermediate to 19,986.7 μL of assay buffer.
26. The primary antibody solution was removed from the tray.
27. The membrane was washed for five minutes with 20 mL of wash buffer and then the wash solution discarded. The wash was repeated for a total of 4 washes.
28. A volume of 20 mL of the secondary antibody solution was added to the membrane and was incubated on a plate shaker at room temperature for 1 hour.
29. The secondary antibody solution was removed from the tray.
30. The membrane was washed for five minutes with 20 mL of wash buffer and then the wash solution discarded. The wash was repeated for a total of 4 washes.
31. The membrane was rinsed with PBS for 5 minutes.
32. The membrane was scanned using the LiCor Odyssey CLx.

Results:

Table 10 contains the results for the DX-2930 and DX-88 inhibition experiment. The percent of two-chain was calculated within each lane and calculated by comparing the treated signal to the untreated signal. For this comparison, the percent of two-chain in lane was used. The untreated NHP pool produced a percent of two-chain value of 3.8%. When the NHP pool was treated with only FXIIa, the two replicate samples produced percent of two-chain values of 24.4%. Samples pre-treated with DX-2930 produced slightly lower percent of two-chain values compared to samples prepared with DX-88. Samples pre-treated with 5 μg/mL of DX-2930 and 0.24 μg/mL of DX-88 produced percent of two-chain values of 22.3% and 23.9% respectively. These values are very close to the percent of two-chain value in sample treated only with FXIIa.

Conclusion:

Samples pre-treated with DX-2930 produced slightly lower percent of two-chain values than samples pre-treated with DX-88.

TABLE 10

Inhibition of FXIIa using DX-2930 and DX-88, HMWK Signals, Percent of Two-Chain HMWK Inhibition of FXIIa Contact Activation using DX-88 and DX-2930

| FXIIa (nM) | DX2930 (μg/mL) | DX88 (μg/mL) | HMWK Signal | | | | % Two-Chain in Lane | % Two-Chain from Untreated Signal |
|---|---|---|---|---|---|---|---|---|
| | | | Single-Chain (110 kDa) | Two-Chain (56 kDa) | Two-Chain (46 kDa) | Total Signal | | |
| 0.00 | 0.00 | 0.00 | 26600 | 413 | 643 | 27656 | 3.8% | N/A |
| 2.50 | 0.00 | 0.00 | 20500 | 3920 | 2690 | 27110 | 24.4% | 22.9% |
| 2.50 | 0.00 | 0.00 | 21200 | 4470 | 2390 | 28060 | 24.4% | 20.3% |
| 2.50 | 200.00 | 0.00 | 27200 | 376 | 576 | 28152 | 3.4% | −2.3% |
| 2.50 | 100.00 | 0.00 | 25300 | 206 | 212 | 25718 | 1.6% | 4.9% |
| 2.50 | 30.00 | 0.00 | 24700 | 784 | 1470 | 26954 | 8.4% | 7.1% |
| 2.50 | 12.00 | 0.00 | 23200 | 3170 | 1560 | 27930 | 16.9% | 12.8% |
| 2.50 | 5.00 | 0.00 | 20100 | 3630 | 2140 | 25870 | 22.3% | 24.4% |
| 2.50 | 0.00 | 9.40 | 22600 | 615 | 663 | 23878 | 5.4% | 15.0% |
| 2.50 | 0.00 | 4.70 | 22500 | 349 | 592 | 23441 | 4.0% | 15.4% |
| 2.50 | 0.00 | 1.40 | 21500 | 2210 | 1270 | 24980 | 13.9% | 19.2% |
| 2.50 | 0.00 | 0.56 | 20600 | 3340 | 1990 | 25930 | 20.6% | 22.6% |
| 2.50 | 0.00 | 0.24 | 19500 | 3910 | 2200 | 25610 | 23.9% | 26.7% |

% Two-Chain in Lane: Sum of Two-Chain Signal/Sum of Total Lane Signal
% Two-Chain from Untreated Signal: 1 − (Treated Single-Chain Signal/Untreated Single-Chain Signal)

Example 7. Determination of Levels of Cleaved Kininogen in HAE, RA, UC, and CD Patient Samples Purpose:

The purpose of this experiment was to evaluate antiprotease treated plasma samples from patients with hereditary angioedema (HAE). Two HAE samples were tested from each patient, one basal sample and one attack sample. The samples were tested under reduced and non-reduced conditions. In addition, samples from patients diagnosed with Crohn's disease, rheumatoid arthritis, and ulcerative colitis were tested. Normal human plasma samples were also tested. The additional samples were tested under only reduced conditions.

Procedure:
1. Six sets of HAE patient samples were tested. Each plasma sample was prepared by adding 5 µL of sample to 95 µL of TBS.
2. Five Crohn's disease plasma samples, five rheumatoid arthritis plasma samples, and five ulcerative colitis samples were tested. Each plasma sample was prepared by adding 5 µL of sample to 95 µL of TBS.
3. Seven normal human plasma samples were prepared as use for controls by adding 5 µL of sample to 95 µL of TBS.
4. Non-reduced samples were prepared by adding 5 µL of the 4× sample buffer to 15 µL of sample.
5. Reduced samples were prepared by adding 5 µL of the 4× sample buffer and 2 µL of 10×reducing agent to 13 µL of sample.
6. All of the samples were heated at 95° C. for 5 minutes using a heat block.
7. A volume of 1 L of 1× Tris-Acetate SDS running buffer was prepared by adding 50 mL of 20× Tris-Acetate SDS running buffer to 950 mL of DI water.
8. A volume of 2 L of 1×MES running buffer was prepared by adding 100 mL of 20×MES SDS running buffer to 1900 mL of DI water.
9. Assay buffer (Odyssey Blocking buffer with 0.2% Tween) was prepared by adding 2 mL of Tween-20 to 998 mL of Odyssey blocking buffer.
10. Wash buffer (PBS with 0.1% Tween) was prepared by adding 1 packet of PBS and 1 mL of Tween-20 to 900 mL of DI water. The solution was mixed well and QS'd to 1 L using DI water. The final solution was filtered through a 0.22 µM PES filtration system.
11. A volume of 4 µL of one-color protein marker was added to lane 1 of four gels.
12. Volumes of 13 µl of the non-reduced samples were added to the appropriate lanes of a 7% Tris-Acetate gel.
13. Volumes of 13 µL of the reduced samples were added to the appropriate lanes of 4-12% Bis-Tris gels.
14. The gels were run at 125 volts for ~75 minutes.
15. Each gel was individually transferred to a membrane using the iBlot mini-transfer stacks and Program P0 on the iBlot transfer system.
16. Each membrane was transferred to a plastic tray containing 20 mL of Odyssey blocking buffer. The membranes were incubated in Odyssey blocking buffer on a plate shaker at room temperature for 1 hour.
17. A 1 µg/mL primary antibody solution was prepared by adding 57.14 µL of the mouse anti-HMWK mAb, clone #11H05, 1.4 mg/mL to 79,942.86 µL of assay buffer.
18. The blocking buffer was removed from the plastic trays. A volume of 20 mL of the primary antibody solution was added to each tray and the membranes were incubated on a plate shaker at room temperature for 1 hour.
19. A 1:10 intermediate of goat anti-mouse IgG IRDye680 was prepared by adding 10 µL of the goat anti-mouse IgG IRDye680 to 90 µL of assay buffer. The secondary antibody solution was prepared at a 1:15,000 dilution by adding 53.33 µL of the 1:10 goat anti-mouse IgG IRDye680 intermediate to 79,946.67 µL of assay buffer.
20. The primary antibody solution was removed from the trays.
21. Each membrane was washed for five minutes with 20 mL of wash buffer and then the wash solution discarded. The wash was repeated for a total of 4 washes.
22. A volume of 20 mL of the secondary antibody solution was added to each tray and the membranes were incubated on a plate shaker at room temperature for 1 hour.
23. The secondary antibody solution was removed from the trays.
24. Each membrane was washed for five minutes with 20 mL of wash buffer and then the wash solution discarded. The wash was repeated for a total of 4 washes.
25. Each membrane was rinsed with PBS for 5 minutes.
26. The membranes were scanned using the LiCor Odyssey CLx.

Results:

As expected most patient samples exhibited an elevated level of two-chain HMWK in the attack samples as opposed to the basal samples. Tables 11 and 12 contain the HAE data for this experiment. Table 13 contains the data set for the ulcerative colitis and rheumatoid arthritis patient samples. Table 14 contains the data for the Crohn's disease patient samples.

TABLE 11

Non-Reduced HAE Patient Samples, Basal and Attack, HMWK Signals, Percent of Two-Chain in Lane
Non-Reduced anti-Protease HAE Patient Samples, Basal and Attack

| Patient ID | Patient Initials | HAE | HMWK Signal 120 kDa | 100 kDa | 90 kDa | Total Signal | % Two-Chain in Lane |
|---|---|---|---|---|---|---|---|
| A3009 | N18 | Normal | 15500 | 3750 | N/A | 19250 | 19.5% |
| A4970 | AC | Basal | 13000 | 4300 | 240 | 17540 | 25.9% |
| A4908 | AC | Attack | 9450 | 5910 | 1740 | 17100 | 44.7% |
| A5564 | BB | Basal | 15900 | 5650 | 585 | 22135 | 28.2% |
| A5353 | BB | Attack | 11600 | 10500 | 2340 | 24440 | 52.5% |
| A4607 | FF | Basal | 11400 | 4850 | N/A | 16250 | 29.8% |
| A4619 | FF | Attack | 6770 | 6750 | 2090 | 15610 | 56.6% |
| A5346 | DG | Basal | 10800 | 3850 | 102 | 14752 | 26.8% |
| A5422 | DG | Attack | 5650 | 2080 | 133 | 7863 | 28.1% |
| A4183 | PC | Basal | 9530 | 1190 | N/A | 10720 | 11.1% |
| A4671 | PC | Attack | 8840 | 1570 | N/A | 10410 | 15.1% |
| A5248 | GR | Basal | 14300 | 4270 | 44.1 | 18614.1 | 23.2% |
| A2315 | GR | Attack | 11600 | 4610 | 490 | 16700 | 30.5% |

% Two-Chain in Lane: Sum of Two-Chain Signal/Sum of Total Lane Signal

TABLE 12

Reduced HAE Patient Samples, Basal and Attack, HMWK Signals, Percent of Two-Chain in Lane
Reduced anti-Protease HAE Patient Samples, Basal and Attack

| Patient ID | Patient Initials | HAE | HMWK Signal 110 kDa | 56 kDa | 46 kDa | Total Signal | % Two-Chain in Lane |
|---|---|---|---|---|---|---|---|
| A3009 | N18 | Normal | 18700 | 802 | 926 | 20428 | 8.5% |
| A4970 | AC | Basal | 14500 | 2980 | 1480 | 18960 | 23.5% |
| A4908 | AC | Attack | 8500 | 3540 | 2670 | 14710 | 42.2% |
| A5564 | BB | Basal | 12400 | 3160 | 1380 | 16940 | 26.8% |
| A5353 | BB | Attack | 8980 | 3980 | 2620 | 15580 | 42.4% |
| A4607 | FF | Basal | 10900 | 2490 | 1620 | 15010 | 27.4% |
| A4619 | FF | Attack | 6130 | 3930 | 2520 | 12580 | 51.3% |
| A5346 | DG | Basal | 11200 | 2400 | 709 | 14309 | 21.7% |
| A5422 | DG | Attack | 7900 | 2640 | 749 | 11289 | 30.0% |
| A4183 | PC | Basal | 13900 | 1850 | 572 | 16322 | 14.8% |
| A4671 | PC | Attack | 13500 | 2120 | 572 | 16192 | 16.6% |
| A5248 | GR | Basal | 19000 | 2120 | 1160 | 22280 | 14.7% |
| A2315 | GR | Attack | 16400 | 3660 | 1580 | 21640 | 24.2% |

% Two-Chain in Lane: Sum of Two-Chain Signal/Sum of Total Lane Signal

TABLE 13

Plasma Samples from Individuals with Ulcerative Colitis and Rheumatoid Arthritis, HMWK Signals, Percent of Two-Chain in Lane
Reduced Diseased State Samples in K2EDTA and Sodium Citrate, Ulcerative Collitis and Rheumatoid Arthritis

| | | | HMWK Signal | | | | |
|---|---|---|---|---|---|---|---|
| Sample | anti-Coagulant | Disease | Single-Chain (110 kDa) | Two-Chain (56 kDa) | Two-Chain (46 kDa) | Total Signal | % Two-Chain in Lane |
| A3005, N17 | anti-protease | Normal | 20500 | 775 | 366 | 21641 | 5.3% |
| BRH745075 | Sodium Citrate | Normal | 18700 | 1340 | 802 | 20842 | 10.3% |
| BRH745056 | Sodium Citrate | Normal | 24200 | 893 | 782 | 25875 | 6.5% |
| BRH715036 | K2EDTA | Ulcerative Collitis | 17400 | 3030 | 1340 | 21770 | 20.1% |
| BRH715037 | Sodium Citrate | Ulcerative Collitis | 17400 | 1220 | 694 | 19314 | 9.9% |
| BRH715038 | Sodium Citrate | Ulcerative Collitis | N/A | 2140 | 10300 | 12440 | 100.0% |
| BRH715039 | Sodium Citrate | Ulcerative Collitis | 14100 | 1700 | 596 | 16396 | 14.0% |
| BRH715040 | Sodium Citrate | Ulcerative Collitis | 13300 | 1170 | 2070 | 16540 | 19.6% |
| BRH715041 | K2EDTA | Rheumatoid Arthritis | N/A | N/A | 4950 | 4950 | 100.0% |
| BRH715042 | K2EDTA | Rheumatoid Arthritis | 88 | N/A | 9250 | 9338 | 99.1% |
| BRH715043 | K2EDTA | Rheumatoid Arthritis | N/A | N/A | 6900 | 6900 | 100.0% |
| BRH715044 | Sodium Citrate | Rheumatoid Arthritis | N/A | N/A | 2850 | 2850 | 100.0% |
| BRH715045 | Sodium Citrate | Rheumatoid Arthritis | 6600 | 1860 | 1520 | 9980 | 33.9% |

% Two-Chain in Lane: Sum of Two-Chain Signal/Sum of Total Lane Signal

TABLE 14

Plasma Samples from Individuals with Crohn's Disease, HMWK Signals, Percent of Two-Chain in Lane
Reduced Diseased State Samples in K2EDTA and Sodium Citrate, Crohn's Disease and Psoriasis

| | | | HMWK Signal | | | | | |
|---|---|---|---|---|---|---|---|---|
| Sample | anti-Coagulant | Disease | Single-Chain (150 kDa) | Single-Chain (110 kDa) | Two-Chain (56 kDa) | Two-Chain (46 kDa) | Total Signal | % Two-Chain in Lane |
| A2992, N14 | Sodium Citrate | Normal | 704 | 12900 | 384 | 576 | 14564 | 6.6% |
| BRH745047 | Sodium Citrate | Normal | 1560 | 5820 | N/A | 192 | 7572 | 2.5% |
| BRH745076 | Sodium Citrate | Normal | 5720 | 12300 | 382 | 480 | 18882 | 4.6% |
| BRH715026 | K2EDTA | Crohn's Disease | N/A | 12100 | 1230 | 1950 | 15280 | 20.8% |
| BRH715027 | K2EDTA | Crohn's Disease | N/A | 16300 | 668 | 1550 | 18518 | 12.0% |
| BRH715028 | K2EDTA | Crohn's Disease | N/A | 6650 | 504 | 2250 | 9404 | 29.3% |
| BRH715029 | K2EDTA | Crohn's Disease | 1900 | 14100 | N/A | 680 | 16680 | 4.1% |
| BRH715030 | K2EDTA | Crohn's Disease | N/A | 1320 | 3230 | 6020 | 10570 | 87.5% |

% Two-Chain in Lane: Sum of Two-Chain Signal/Sum of Total Lane Signal

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

---

What is claimed is:

1. A method comprising:
   (a) contacting a sample suspected of containing intact and cleaved high molecular weight kininogen (HMWK) with at least one antibody under conditions allowing for binding between the antibody and the intact HMWK or between the antibody and the cleaved HMWK; and
   (b) measuring the level of cleaved HMWK or the level of intact HMWK in the sample based on detecting binding between the cleaved HMWK or the intact HMWK and the antibody;
   wherein the sample is obtained from a human patient at risk for or having a plasma kallikrein (pKal)-mediated disorder; and wherein the antibody specifically binds intact HMWK or cleaved HMWK.

2. The method of claim 1, wherein the method further comprises (c) determining the percentage of the cleaved HMWK or the percentage of the intact HMWK based on the levels of the cleaved HMWK and intact HMWK measured in step (b).

3. The method of claim 2, wherein the percentage of the cleaved HMWK is determined.

4. The method of claim 1, wherein the levels of the intact HMWK and cleaved HMWK are measured by Western blot assay.

5. The method of claim 1, wherein the sample is a blood sample or a plasma sample.

6. The method of claim 1, wherein the pKal-mediated disorder is hereditary angioedema (HAE), rheumatoid arthritis, ulcerative colitis, or Crohn's disease.

7. The method of claim 1, wherein the human patient has a symptom of the pKal-mediated disorder.

8. The method of claim 1, wherein the human patient has no symptom of the pKal-mediated disorder at the time the sample is collected, has no history of a symptom of the pKal-mediated disorder, or has no history of the pKal-mediated disorder.

9. A method for treating a plasma kallikrein (pKal)-mediated disorder, the method comprising:
  (a) contacting a sample of a human patient with at least one antibody under conditions allowing for binding between the antibody and intact high molecular weight kininogen (HMWK), between the antibody and cleaved HMWK, or both;
  (b) measuring the level of cleaved HMWK and the level of intact HMWK in the sample based on their interaction with the antibody;
  (c) determining a value of the cleaved HMWK, a value of the intact HMWK, or both, in the sample based on the amounts of the cleaved HMWK and intact HMWK measured in step (b),
  (d) identifying the human patient as at risk for or having the pKal-mediated disorder, if the value of the cleaved HMWK is at or above a reference value; and
  (e) administering an effective amount of a pKal inhibitor to the human patient, if the human patient is identified as being at risk for or having a pKal-mediated disorder in step (d);
  wherein the pKal-mediated disorder is hereditary angioedema (HAE), rheumatoid arthritis (RA), ulcerative colitis (UC), or Crohn's disease (CD).

10. The method of claim 9, wherein the pKal inhibitor is DX-88, EPIKAL-2 or DX-2930.

11. The method of claim 9, wherein the sample is a blood sample or a plasma sample.

12. A method for identifying a plasma kallikrein (pKal)-mediated disorder as being susceptible to treatment with a pKal inhibitor, the method comprising:
  (a) contacting a sample of a human patient at risk for or having a pKal-mediated disorder with at least one antibody under conditions allowing for binding between the antibody and intact high molecular weight kininogen (HMWK), between the antibody and cleaved HMWK, or both;
  (b) measuring the level of cleaved HMWK and the level of intact HMWK in the sample based on their interaction with the antibody; and
  (c) determining a value of the cleaved HMWK, a value of the intact HMWK, or both, in the sample based on the amounts of the cleaved HMWK and intact HMWK,
  (d) identifying the pKal-mediated disorder as being susceptible to treatment with a pKal inhibitor, if the value of the cleaved HMWK deviates a reference value; and
  (e) administering an effective amount of a pKal inhibitor to the human patient, if the pKal-mediated disorder is identified as being susceptible to treatment with the pKal inhibitor in step (d);
  wherein the pKal-mediated disorder is hereditary angioedema (HAE), rheumatoid arthritis (RA), ulcerative colitis (UC), or Crohn's disease (CD).

13. The method of claim 12, wherein the method further comprises identifying the treatment as being effective based on changes in the values of the cleaved HMWK and/or intact HMWK in the samples over the course of the treatment.

14. The method of claim 12, wherein the sample is a blood sample or a plasma sample.

15. The method of claim 12, wherein the pKal inhibitor is DX-88, EPIKAL-2 or DX-2930.

* * * * *